(12) United States Patent
Ricci

(10) Patent No.: US 10,762,553 B2
(45) Date of Patent: Sep. 1, 2020

(54) COLLECTING BATTERY PACK STATE INFORMATION

(71) Applicant: NIO USA, Inc., San Jose, CA (US)

(72) Inventor: Christopher P. Ricci, Saratoga, CA (US)

(73) Assignee: NIO USA, Inc., San Jose, CA (US)

( * ) Notice: Subject to any disclaimer, the term of this patent is extended or adjusted under 35 U.S.C. 154(b) by 297 days.

(21) Appl. No.: 15/339,540

(22) Filed: Oct. 31, 2016

(65) Prior Publication Data
US 2018/0009330 A1    Jan. 11, 2018

Related U.S. Application Data

(60) Provisional application No. 62/359,563, filed on Jul. 7, 2016, provisional application No. 62/378,348, filed on Aug. 23, 2016.

(51) Int. Cl.
*G01M 17/00* (2006.01)
*G06Q 30/06* (2012.01)
(Continued)

(52) U.S. Cl.
CPC ........ *G06Q 30/0635* (2013.01); *A61B 5/1171* (2016.02); *A61B 5/1172* (2013.01);
(Continued)

(58) Field of Classification Search
CPC ............ G01R 31/3651; G01R 31/3679; G01R 31/3624; G01R 31/025; G01R 31/3606; G01R 31/362; G01R 31/3662; G01R 31/3668; B60L 11/1892; B60L 2200/26; B60L 11/123; B60L 11/1881; B60L 11/1894; B60L 15/06; B60L 3/12; B60L 11/18; B60L 11/182; B60L 11/1857; B60L 11/1887; B60L 1/00; B60L 1/003; B60L 2200/36; B60L 2220/12; B60L 2220/14; B60L 2240/423; B60L 2240/70; B60L 2250/10; B60L 2250/16; B60L 5/005; B60L 7/14; B60L 9/00; Y02T 10/6217; Y02T 10/7005; Y02T 90/34; Y02T 10/644; Y02T 10/7077; Y02T 10/646; Y02T 10/705; Y02T 10/7072; Y02T 10/7291;
(Continued)

(56) References Cited

U.S. PATENT DOCUMENTS

| 7,106,174 B1 * | 9/2006 | Powell | ................. G06K 7/0008 340/10.1 |
| 8,820,626 B2 * | 9/2014 | Rich | ..................... H01M 10/48 235/375 |

(Continued)

OTHER PUBLICATIONS

"Multi-factor authentication," Wikipedia, retrieved from https://en.wikipedia.org/wiki/Multi-factor_authentication, retrieved on Dec. 9, 2016, 6 pages.

(Continued)

*Primary Examiner* — Khoi H Tran
*Assistant Examiner* — B M M Hannan
(74) *Attorney, Agent, or Firm* — Sheridan Ross P.C.

(57) ABSTRACT

Systems of an electrical vehicle and the operations thereof are provided that use identifiers and sensed power source parameters to determine whether a rule, such as a warranty or licensing requirement, has been violated.

20 Claims, 29 Drawing Sheets

Fig. 2

(51) Int. Cl.
| | |
|---|---|
| H04W 4/44 | (2018.01) |
| G01C 21/36 | (2006.01) |
| G08G 1/0962 | (2006.01) |
| G08G 1/0967 | (2006.01) |
| G08G 1/0968 | (2006.01) |
| H01Q 1/32 | (2006.01) |
| H04W 12/06 | (2009.01) |
| G06F 21/31 | (2013.01) |
| G06Q 20/10 | (2012.01) |
| G06Q 20/14 | (2012.01) |
| G06Q 20/32 | (2012.01) |
| G06Q 20/40 | (2012.01) |
| H04L 9/32 | (2006.01) |
| B60L 53/14 | (2019.01) |
| B60L 53/12 | (2019.01) |
| B60L 53/80 | (2019.01) |
| B60L 53/65 | (2019.01) |
| B60L 53/66 | (2019.01) |
| G06Q 10/00 | (2012.01) |
| G06Q 30/02 | (2012.01) |
| G07C 5/00 | (2006.01) |
| H04W 4/80 | (2018.01) |
| G06Q 30/00 | (2012.01) |
| G07C 5/08 | (2006.01) |
| A61B 5/1171 | (2016.01) |
| A61B 5/1172 | (2016.01) |
| G07C 5/02 | (2006.01) |
| G07C 9/00 | (2020.01) |
| G06F 3/01 | (2006.01) |
| G06K 9/00 | (2006.01) |
| H02J 7/00 | (2006.01) |
| H01Q 21/30 | (2006.01) |
| H04B 5/00 | (2006.01) |
| B60W 40/08 | (2012.01) |
| B60W 50/08 | (2020.01) |
| G08G 1/017 | (2006.01) |
| G08G 1/00 | (2006.01) |
| G07B 15/06 | (2011.01) |
| G06F 21/62 | (2013.01) |
| H04W 12/02 | (2009.01) |
| G05D 1/00 | (2006.01) |
| G06F 21/32 | (2013.01) |
| B60L 5/24 | (2006.01) |
| B60M 7/00 | (2006.01) |
| G08G 1/16 | (2006.01) |
| B60L 7/10 | (2006.01) |
| B60L 8/00 | (2006.01) |
| B60L 9/00 | (2019.01) |
| G01S 13/931 | (2020.01) |
| B60K 35/00 | (2006.01) |
| B60R 11/00 | (2006.01) |
| B60W 50/14 | (2020.01) |
| B60M 1/00 | (2006.01) |

(52) U.S. Cl.
CPC ............ *A61B 5/1176* (2013.01); *B60L 53/12* (2019.02); *B60L 53/14* (2019.02); *B60L 53/65* (2019.02); *B60L 53/665* (2019.02); *B60L 53/80* (2019.02); *B60W 40/08* (2013.01); *B60W 50/08* (2013.01); *G01C 21/36* (2013.01); *G01C 21/3617* (2013.01); *G01C 21/3697* (2013.01); *G05D 1/0011* (2013.01); *G05D 1/0088* (2013.01); *G06F 3/011* (2013.01); *G06F 21/31* (2013.01); *G06F 21/32* (2013.01); *G06F 21/6245* (2013.01); *G06K 9/00087* (2013.01); *G06K 9/00832* (2013.01); *G06K 9/00845* (2013.01); *G06Q 10/20* (2013.01); *G06Q 20/105* (2013.01); *G06Q 20/108* (2013.01); *G06Q 20/14* (2013.01); *G06Q 20/32* (2013.01); *G06Q 20/3224* (2013.01); *G06Q 20/401* (2013.01); *G06Q 20/405* (2013.01); *G06Q 20/4012* (2013.01); *G06Q 30/012* (2013.01); *G06Q 30/0206* (2013.01); *G06Q 30/0208* (2013.01); *G06Q 30/0601* (2013.01); *G06Q 30/0609* (2013.01); *G06Q 30/0613* (2013.01); *G06Q 30/0625* (2013.01); *G06Q 30/0637* (2013.01); *G07B 15/063* (2013.01); *G07C 5/008* (2013.01); *G07C 5/02* (2013.01); *G07C 5/0808* (2013.01); *G07C 5/0816* (2013.01); *G07C 5/0858* (2013.01); *G07C 9/00563* (2013.01); *G08G 1/017* (2013.01); *G08G 1/0962* (2013.01); *G08G 1/09626* (2013.01); *G08G 1/096775* (2013.01); *G08G 1/096827* (2013.01); *G08G 1/096838* (2013.01); *G08G 1/20* (2013.01); *H01Q 1/325* (2013.01); *H01Q 1/3266* (2013.01); *H01Q 1/3275* (2013.01); *H01Q 1/3283* (2013.01); *H01Q 1/3291* (2013.01); *H01Q 21/30* (2013.01); *H02J 7/0068* (2013.01); *H04B 5/0037* (2013.01); *H04L 9/321* (2013.01); *H04L 9/3226* (2013.01); *H04W 4/44* (2018.02); *H04W 4/80* (2018.02); *H04W 12/02* (2013.01); *H04W 12/06* (2013.01); *A61B 2503/22* (2013.01); *B60K 35/00* (2013.01); *B60K 2370/1537* (2019.05); *B60K 2370/334* (2019.05); *B60L 5/24* (2013.01); *B60L 7/10* (2013.01); *B60L 8/003* (2013.01); *B60L 8/006* (2013.01); *B60L 9/00* (2013.01); *B60L 2240/549* (2013.01); *B60L 2240/70* (2013.01); *B60L 2240/72* (2013.01); *B60L 2270/32* (2013.01); *B60M 1/00* (2013.01); *B60M 7/00* (2013.01); *B60R 2011/0003* (2013.01); *B60R 2011/004* (2013.01); *B60R 2300/30* (2013.01); *B60R 2300/804* (2013.01); *B60R 2325/105* (2013.01); *B60W 2040/0809* (2013.01); *B60W 2050/143* (2013.01); *B60W 2050/146* (2013.01); *B60W 2300/34* (2013.01); *B60W 2540/00* (2013.01); *B60W 2540/21* (2020.02); *B60W 2540/215* (2020.02); *B60Y 2200/91* (2013.01); *B60Y 2200/912* (2013.01); *B60Y 2200/92* (2013.01); *B60Y 2300/60* (2013.01); *B60Y 2302/07* (2013.01); *B60Y 2400/92* (2013.01); *G01S 2013/9316* (2020.01); *G06K 9/00288* (2013.01); *G06K 9/00885* (2013.01); *G08G 1/16* (2013.01); *H04L 2209/80* (2013.01); *H04L 2209/805* (2013.01); *H04L 2209/84* (2013.01); *Y02T 10/7005* (2013.01); *Y02T 10/7072* (2013.01); *Y02T 10/7083* (2013.01); *Y02T 10/7291* (2013.01); *Y02T 90/121* (2013.01); *Y02T 90/122* (2013.01); *Y02T 90/124* (2013.01); *Y02T 90/128* (2013.01); *Y02T 90/14* (2013.01); *Y02T 90/16* (2013.01); *Y02T 90/161* (2013.01); *Y02T 90/163* (2013.01); *Y02T 90/169* (2013.01); *Y04S 30/14* (2013.01)

(58) Field of Classification Search
CPC ....... Y02T 90/122; Y02T 90/14; Y02T 90/16; A62C 27/00; H01M 10/48; H01M 10/42; H01M 10/44; H01M 10/484; H01M 10/486; H01M 2010/4278; H01M 2220/30; H01M 2/1016; A01K 15/023; B28C 5/4206; B60K 1/02; B60K 1/04; B60K 6/46; B60K 7/0007; B60R 16/0315; B60W 10/08; B60W 20/00; B60Y 2200/14; B65F 3/043; B65F 3/045; G01M 17/00; G05B 13/028; G06F 17/40; G06F 21/44; G06F 21/602; G06F 2221/2129; G07C 5/008; G07C 5/08; G07C 5/085; G08G 1/20; H02J 1/14; H02J 2007/0001; H02J 2007/0098; H02J 3/38; H02J 7/0013; H02J 7/0027; H02J 7/0042; H02J 7/0054; H02J 7/0063; H02J 7/007; H02J 7/1461; H04L 2012/2841; H04L 43/16; H04L 51/12; H04L 51/24; H04L 67/141; H04L 9/0841; H04L 9/12; H04Q 2209/43; H04Q 2209/47; H04Q 2209/84; H04Q 9/00; Y02E 60/721; Y02W 30/10; Y04S 10/126; Y10T 307/25

USPC .................................................. 701/31.5

See application file for complete search history.

(56) References Cited

U.S. PATENT DOCUMENTS

| | | | | |
|---|---|---|---|---|
| 9,217,779 | B2* | 12/2015 | Xu | B60L 3/12 |
| 10,288,692 | B2* | 5/2019 | Laskowsky | G01R 31/367 |
| 2002/0109504 | A1* | 8/2002 | Champlin | G01R 31/3651 |
| | | | | 324/426 |
| 2007/0005202 | A1* | 1/2007 | Breed | B60W 50/0205 |
| | | | | 701/29.1 |
| 2009/0313098 | A1* | 12/2009 | Hafner | B60L 8/003 |
| | | | | 705/14.1 |
| 2011/0060538 | A1* | 3/2011 | Fahimi | G01R 31/3679 |
| | | | | 702/63 |
| 2013/0105264 | A1 | 5/2013 | Ruth et al. | |
| 2014/0046499 | A1* | 2/2014 | Raskar | B60L 53/68 |
| | | | | 700/297 |
| 2014/0350716 | A1* | 11/2014 | Fly | G06F 1/3212 |
| | | | | 700/215 |
| 2015/0372954 | A1* | 12/2015 | Dubman | H04L 51/12 |
| | | | | 709/206 |
| 2016/0093927 | A1* | 3/2016 | Marcicki | H01M 10/0525 |
| | | | | 429/50 |
| 2016/0282819 | A1* | 9/2016 | Zeier | G05B 13/028 |
| 2017/0028854 | A1* | 2/2017 | Lee | B60L 11/182 |

OTHER PUBLICATIONS

"Radio-frequency identification," Wikipedia, retrieved from https://en.wikipedia.org/wiki/Radio-frequency_identification, retrieved on Dec. 9, 2016, 23 pages.

"Product code," Wikipedia, retrieved from https://en.wikipedia.org/wiki/Product_code, retrieved on Dec. 9, 2016, 1 page.

"Electronic Product Code," Wikipedia, retrieved from https://en.wikipedia.org/wiki/Electronic_Product_Code, retrieved on Dec. 9, 2016, 4 page.

* cited by examiner

| Charging Type 310A | Compatible Vehicle Charging Panel Types 310B | Compatible Vehicle Storage Units 310C | Available Automation Level 310D | Charging Service Status 310E | Charge Rate 310F | Cost 310G | Other 310H | Shielding 310I |
|---|---|---|---|---|---|---|---|---|
| Station: manual | Roof, Side | x, z | Low | Up | Low | $100 | A, B, C | On |
| Station: manual | Roof, Side | x, z | Low | Up | Medium | $150 | A, C | On |
| Station: manual | Roof, Side | x, z | Low | Up | High | $400 | A, B, C | On |
| Station: robotic | Roof, Side | x, z | Medium | Down | Medium | $150 | A, B, D | On |
| Station: robotic | Roof, Side | x, z | High | Down | High | $500 | B, D | On |
| Station: robotic | Roof, Side | x, z | High | Down | High | $500 | B, C | On |
| Roadway | Side, Lower | x, z | Low | Up | Low | $50 | A, C, E | Off |
| Roadway | Side, Lower | x, z | Medium | Up | Low | $100 | A, C, E | Off |
| Roadway | Side, Lower | x, z | Medium | Up | Low | $100 | A, C, E | Off |
| Emergency: truck | Roof, Side, Lower | x, y | Low | Up | Low | $150 | A, B | Off |
| Emergency: truck | Roof, Side, Lower | x, y | Medium | Up | Medium | $200 | A, B | Off |
| Emergency: truck | Roof, Side, Lower | x, y | Medium | Up | High | $500 | A, D | Off |
| Emergency: UAV | Roof | x | Medium | Down | Medium | $500 | A, B, C | Off |
| Emergency: UAV | Roof | x | High | Down | High | $800 | B | Off |
| Emergency: UAV | Roof | x | High | Down | High | $800 | B | Off |
| Overhead | Roof | x, y | Low | Up | Low | $150 | B, D | Off |
| Overhead | Roof | x, y | Medium | Up | Low | $200 | B, C | Off |
| Overhead | Roof | x, y | Medium | Up | Low | $200 | B, C | Off |

*Fig. 3*

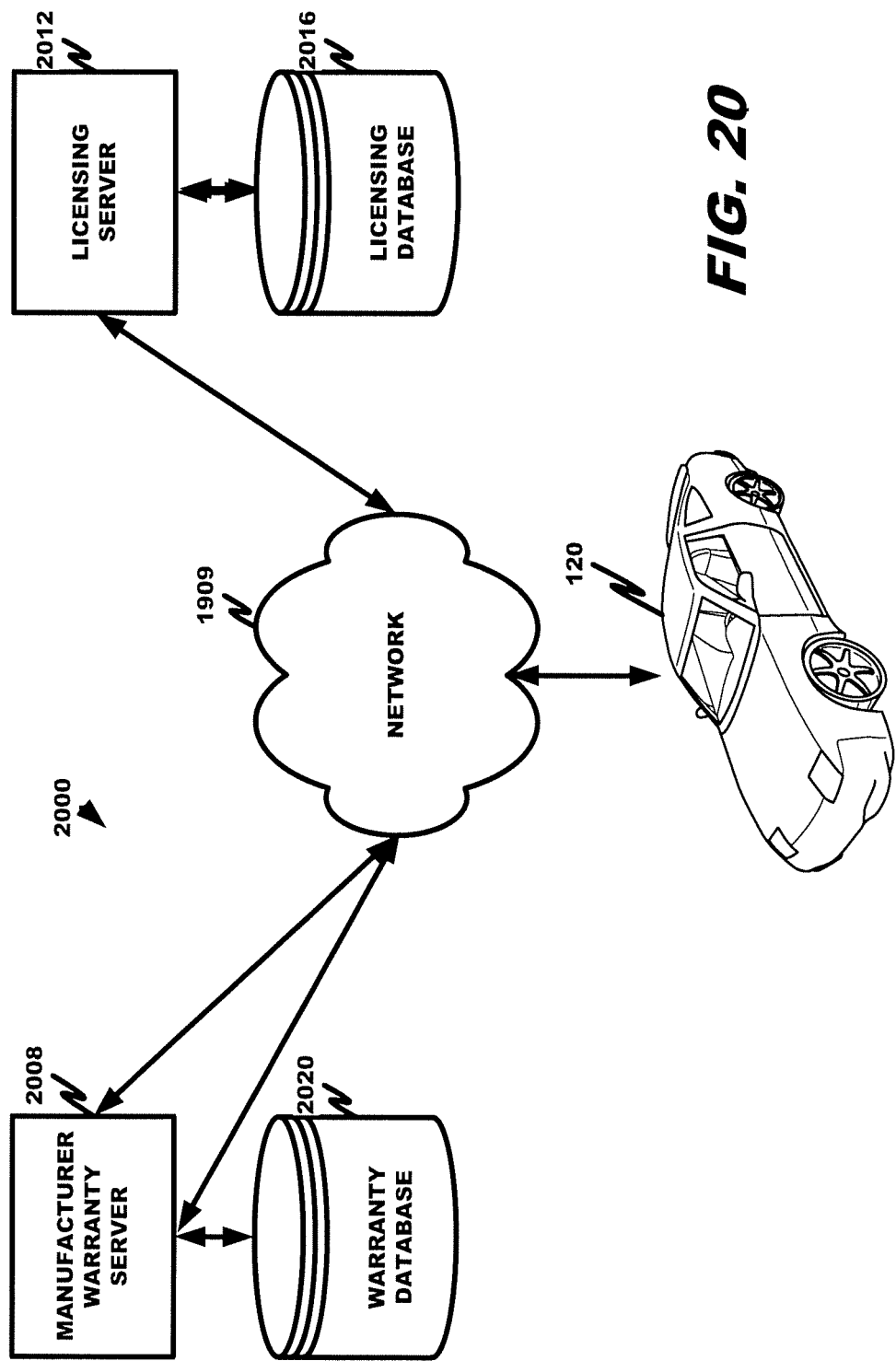

COLLECTING BATTERY PACK STATE INFORMATION

CROSS REFERENCE TO RELATED APPLICATIONS

The present application claims the benefits of and priority, under 35 U.S.C. § 119(e), to U.S. Provisional Application Ser. Nos. 62/359,563, filed Jul. 7, 2016, entitled "Next Generation Vehicle"; and 62/378,348, filed Aug. 23, 2016, entitled "Next Generation Vehicle." The entire disclosures of the applications listed above are hereby incorporated by reference, in their entirety, for all that they teach and for all purposes.

This application is also related to U.S. patent application Ser. No. 14/954,436 filed Nov. 30, 2015, entitled "Electric Vehicle Roadway Charging System and Method of Use"; Ser. No. 14/954,484 filed Nov. 30, 2015, entitled "Electric Vehicle Charging Device Positioning and Method of Use"; Ser. No. 14/979,158 filed Dec. 22, 2015, entitled "Electric Vehicle Charging Device Alignment and Method of Use"; Ser. No. 14/981,368 filed Dec. 28, 2015, entitled "Electric Vehicle Charging Device Obstacle Avoidance and Warning System and Method of Use"; Ser. No. 15/010,701 filed Jan. 29, 2016, entitled "Electric Vehicle Emergency Charging System and Method of Use"; Ser. No. 15/010,921 filed Jan. 29, 2016, entitled "Electric Vehicle Aerial Vehicle Charging System and Method of Use"; Ser. No. 15/044,940 filed Feb. 16, 2016, entitled "Electric Vehicle Overhead Charging System and Method of Use"; Ser. No. 15/048,307 filed Feb. 19, 2016, entitled "Electric Vehicle Charging Station System and Method of Use"; Ser. No. 15/055,345 filed Feb. 26, 2016, entitled "Charging Transmission Line Under Roadway For Moving Electric Vehicle"; Ser. No. 15/074,593 filed Mar. 18, 2016, entitled "Multi-Mode Rechargeable Electric Vehicle"; Ser. No. 15/074,624 filed Mar. 18, 2016, entitled "Distributed Processing Network for Rechargeable Electric Vehicle Tracking and Routing"; Ser. No. 15/143,083 filed Apr. 29, 2016, entitled "Vehicle To Vehicle Charging System and Method of Use"; Ser. No. 15/145,416 filed May 3, 2016, entitled "Electric Vehicle Optical Charging System and Method of Use"; Ser. No. 15/169,073 filed May 31, 2016, entitled "Vehicle Charge Exchange System and Method of Use"; Ser. No. 15/170,406 filed Jun. 1, 2016, entitled "Vehicle Group Charging System and Method of Use"; Ser. No. 15/196,898 filed Jun. 29, 2016, entitled "Predictive Charging System and Method of Use"; Ser. No. 15/198,034 filed Jun. 30, 2016, entitled "Integrated Vehicle Charging Panel System and Method of Use"; Ser. No. 15/223,814 filed Jul. 29, 2016, entitled "Vehicle Skin Charging System and Method"; Ser. No. 15/226,446 filed Aug. 2, 2016, entitled "Vehicle Capacitive Charging System and Method of Use"; Ser. No. 15/237,937 filed Aug. 16, 2016, entitled "Smart Grid Management"; Ser. No. 15/246,867 filed Aug. 25, 2016, entitled "Electric Contact Device for Electric Vehicles and Method of Use"; and Ser. No. 15/254,915 filed Sep. 1, 2016, entitled "Multi-Vehicle Communications and Control System". The entire disclosures of the applications listed above are hereby incorporated by reference, in their entirety, for all that they teach and for all purposes.

FIELD

The present disclosure is generally directed to vehicle systems, in particular, toward electric and/or hybrid-electric vehicles.

BACKGROUND

In recent years, transportation methods have changed substantially. This change is due in part to a concern over the limited availability of natural resources, a proliferation in personal technology, and a societal shift to adopt more environmentally friendly transportation solutions. These considerations have encouraged the development of a number of new flexible-fuel vehicles, hybrid-electric vehicles, and electric vehicles.

While these vehicles appear to be new they are generally implemented as a number of traditional subsystems that are merely tied to an alternative power source. In fact, the design and construction of the vehicles is limited to standard frame sizes, shapes, materials, and transportation concepts. Among other things, these limitations fail to take advantage of the benefits of new technology, power sources, and support infrastructure.

BRIEF DESCRIPTION OF THE DRAWINGS

FIG. 3 is a diagram of an embodiment of a data structure for storing information about a vehicle in an environment;

FIG. 20 is a block diagram of a distributed monitoring system according to an embodiment;

DETAILED DESCRIPTION

Embodiments of the present disclosure will be described in connection with a vehicle, and in accordance with one exemplary embodiment an electric vehicle and/or hybrid-electric vehicle and associated systems.

With attention to FIGS. 1-11, embodiments of the electric vehicle system 10 and method of use are depicted.

Figure 1:
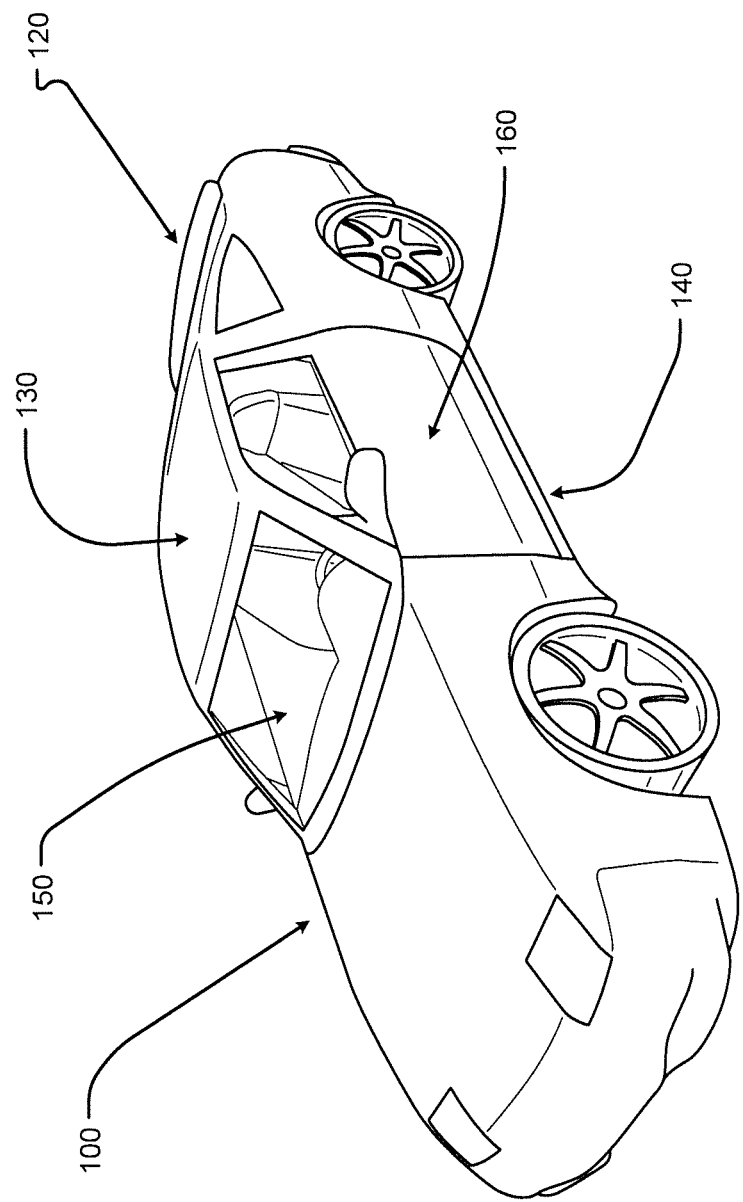
FIG. 1 shows a vehicle in accordance with embodiments of the present disclosure.

Referring to FIG. 1, the electric vehicle system comprises electric vehicle 100. The electric vehicle 100 comprises vehicle front 110, vehicle aft 120, vehicle roof 130, vehicle side 160, vehicle undercarriage 140 and vehicle interior 150.

Figure 2:
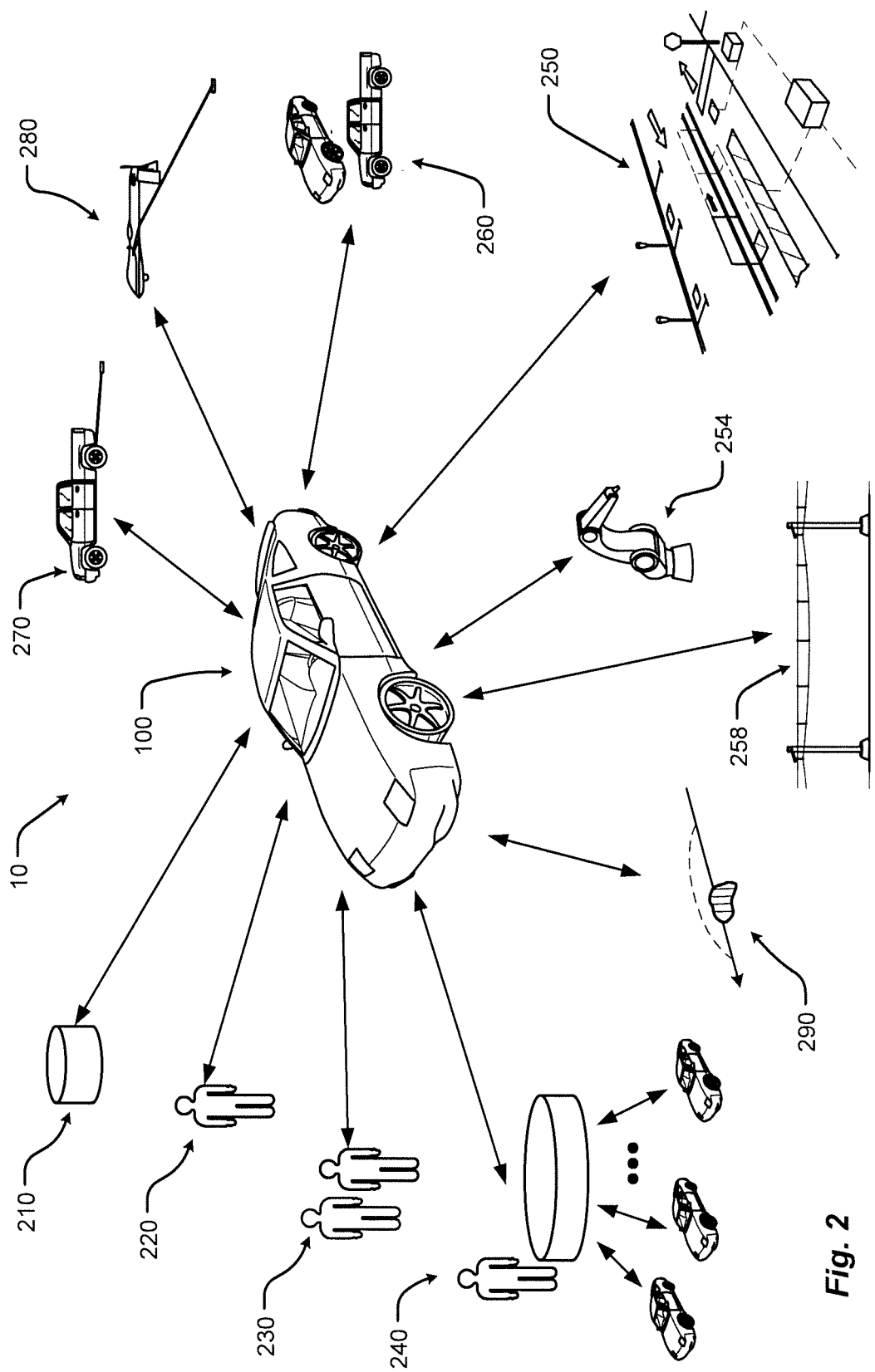
FIG. 2 shows a vehicle in an environment in accordance with embodiments of the present disclosure.

Referring to FIG. 2, the vehicle 100 is depicted in a plurality of exemplary environments. The vehicle 100 may operate in any one or more of the depicted environments in any combination. Other embodiments are possible but are not depicted in FIG. 2. Generally, the vehicle 100 may operate in environments which enable charging of the vehicle 100 and/or operation of the vehicle 100. More specifically, the vehicle 100 may receive a charge via one or more means comprising emergency charging vehicle system 270, aerial vehicle charging system 280, roadway system 250, robotic charging system 254 and overhead charging system 258. The vehicle 100 may interact and/or operate in an environment comprising one or more other roadway vehicles 260. The vehicle 100 may engage with elements within the vehicle 100 comprising vehicle driver 220, vehicle passengers 220 and vehicle database 210. In one embodiment, vehicle database 210 does not physically reside in the vehicle 100 but is instead accessed remotely, e.g. by wireless communication, and resides in another location such as a residence or business location. Vehicle 100 may operate autonomously and/or semi-autonomously in an autonomous environment 290 (here, depicted as a roadway environment presenting a roadway obstacle of which the vehicle 100 autonomously identifies and steers the vehicle 100 clear of the obstacle). Furthermore, the vehicle 100 may engage with a remote operator system 240, which may provide fleet management instructions or control.

FIG. 3 is a diagram of an embodiment of a data structure 300 for storing information about a vehicle 100 in an environment. The data structure may be stored in vehicle database 210. Generally, data structure 300 identifies operational data associated with charging types 310A. The data structures 300 may be accessible by a vehicle controller. The data contained in data structure 300 enables, among other things, for the vehicle 100 to receive a charge from a given charging type.

Data may comprise charging type 310A comprising a manual charging station 310J, robotic charging station 310K such as robotic charging system 254, a roadway charging system 310L such as those of roadway system 250, an emergency charging system 310M such as that of emergency charging vehicle system 270, an emergency charging system 310N such as that of aerial vehicle charging system 280, and overhead charging type 310O such as that of overhead charging system 258.

Compatible vehicle charging panel types 310B comprise locations on vehicle 100 wherein charging may be received, such as vehicle roof 130, vehicle side 160 and vehicle lower or undercarriage 140. Compatible vehicle storage units 310C data indicates storage units types that may receive power from a given charging type 310A. Available automation level 310D data indicates the degree of automation available for a given charging type; a high level may indicate full automation, allowing the vehicle driver 220 and/or vehicle passengers 230 to not involve themselves in charging operations, while a low level of automation may require the driver 220 and/or occupant 230 to manipulate/position a vehicle charging device to engage with a particular charging type 310A to receive charging. Charging status 310E indicates whether a charging type 310A is available for charging (i.e. is "up") or is unavailable for charging (i.e. is "down"). Charge rate 310F provides a relative value for time to charge, while Cost 310G indicates the cost to vehicle 100 to receive a given charge. The Other data element 310H may provide additional data relevant to a given charging type 310A, such as a recommended separation distance between a vehicle charging plate and the charging source. The Shielding data element 310I indicates if electromagnetic shielding is recommended for a given charging type 310A and/or charging configuration. Further data fields 310P, 310Q are possible.

Figure 4A:
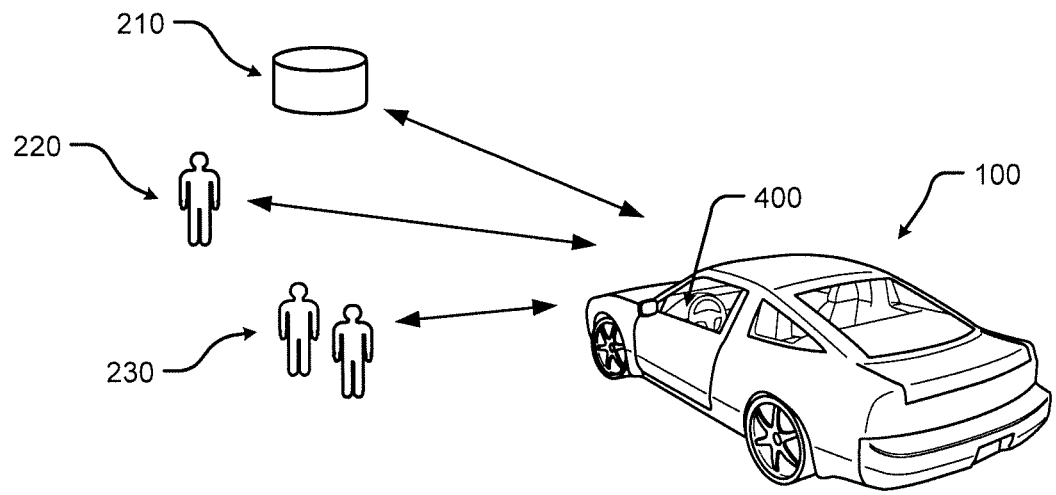
FIG. 4A shows a vehicle in a user environment in accordance with embodiments of the present disclosure.

FIG. 4A depicts the vehicle 100 in a user environment comprising vehicle database 210, vehicle driver 220 and vehicle passengers 230. Vehicle 100 further comprises vehicle instrument panel 400 to facilitate or enable interactions with one or more of vehicle database 210, vehicle driver 220 and vehicle passengers 230. In one embodiment, driver 210 interacts with instrument panel 400 to query database 210 so as to locate available charging options and to consider or weigh associated terms and conditions of the charging options. Once a charging option is selected, driver 210 may engage or operate a manual control device (e.g., a joystick) to position a vehicle charging receiver panel so as to receive a charge.

Figure 4B:
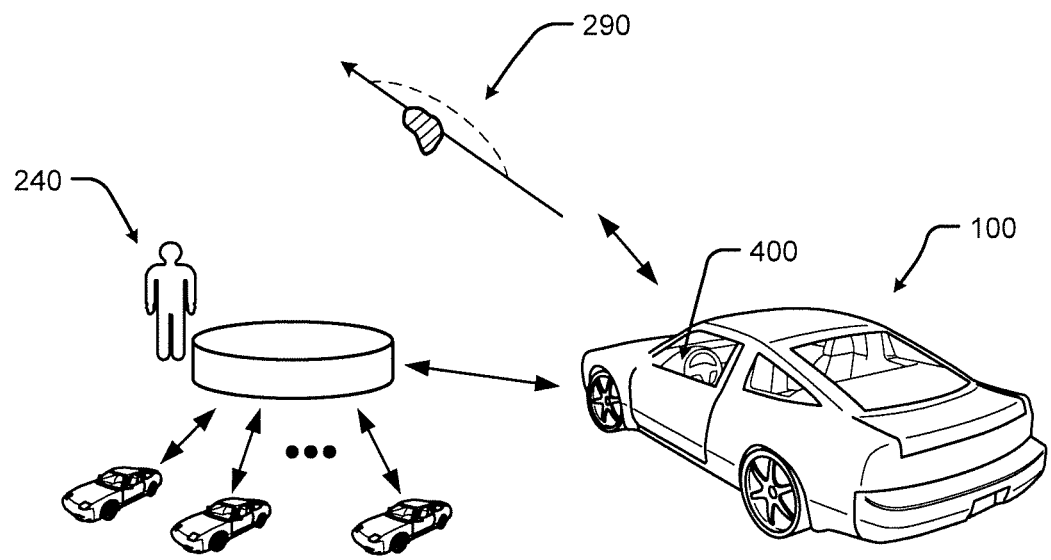
FIG. 4B shows a vehicle in a fleet management and automated operation environment in accordance with embodiments of the present disclosure.

FIG. 4B depicts the vehicle 100 in a user environment comprising a remote operator system 240 and an autonomous driving environment 290. In the remote operator system 240 environment, a fleet of electric vehicles 100 (or mixture of electric and non-electric vehicles) is managed and/or controlled remotely. For example, a human operator may dictate that only certain types of charging types are to be used, or only those charging types below a certain price point are to be used. The remote operator system 240 may comprise a database comprising operational data, such as fleet-wide operational data. In another example, the vehicle 100 may operate in an autonomous driving environment 290 wherein the vehicle 100 is operated with some degree of autonomy, ranging from complete autonomous operation to semi-automation wherein only specific driving parameters (e.g., speed control or obstacle avoidance) are maintained or controlled autonomously. In FIG. 4B, autonomous driving environment 290 depicts an oil slick roadway hazard that triggers that triggers the vehicle 100, while in an automated obstacle avoidance mode, to automatically steer around the roadway hazard.

Figure 4C:
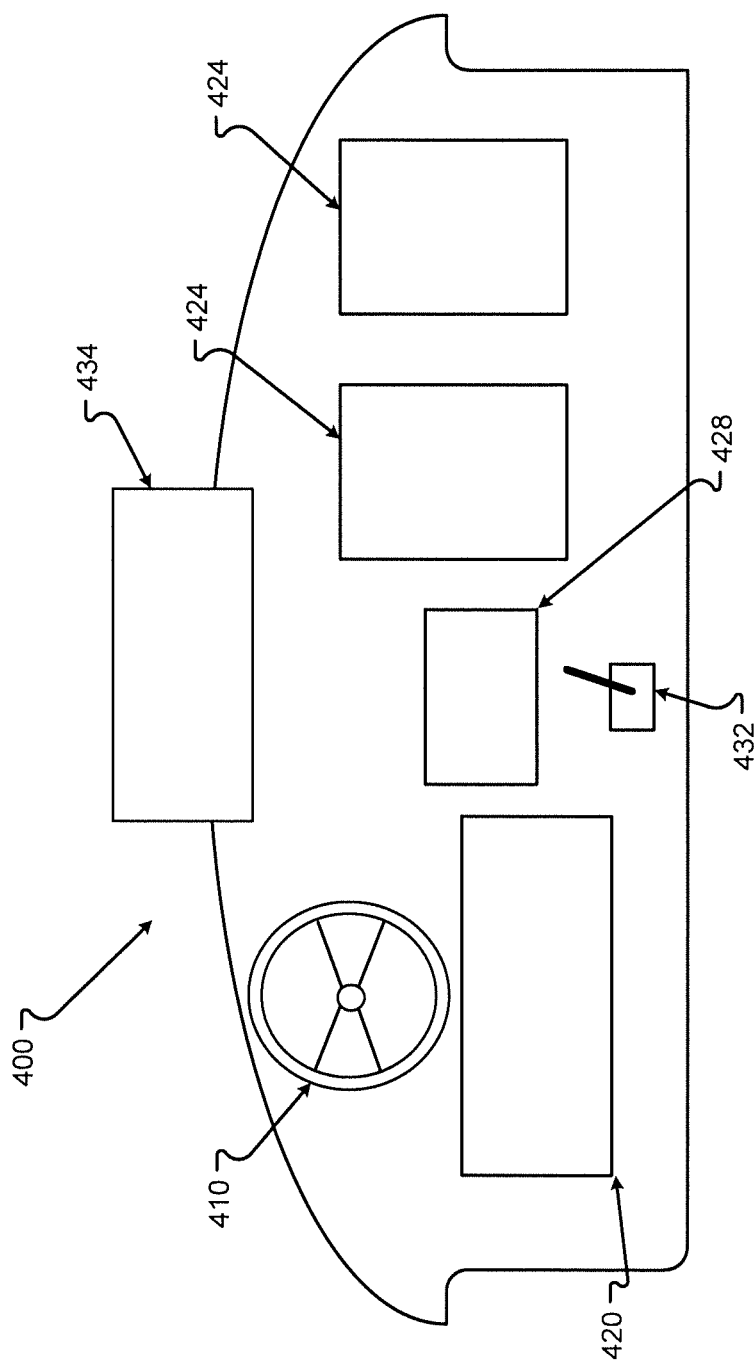
FIG. 4C shows an embodiment of the instrument panel of the vehicle according to one embodiment of the present disclosure.

FIG. 4C shows one embodiment of the vehicle instrument panel 400 of vehicle 100. Instrument panel 400 of vehicle 100 comprises steering wheel 410, vehicle operational display 420 (which would provide basic driving data such as speed), one or more auxiliary displays 424 (which may display, e.g., entertainment applications such as music or radio selections), heads-up display 434 (which may provide, e.g., guidance information such as route to destination, or obstacle warning information to warn of a potential collision, or some or all primary vehicle operational data such as speed), power management display 428 (which may provide, e.g., data as to electric power levels of vehicle 100), and charging manual controller 432 (which provides a physical input, e.g. a joystick, to manual maneuver, e.g., a vehicle charging plate to a desired separation distance). One or more of displays of instrument panel 400 may be touchscreen displays. One or more displays of instrument panel 400 may be mobile devices and/or applications residing on a mobile device such as a smart phone.

Figure 5:
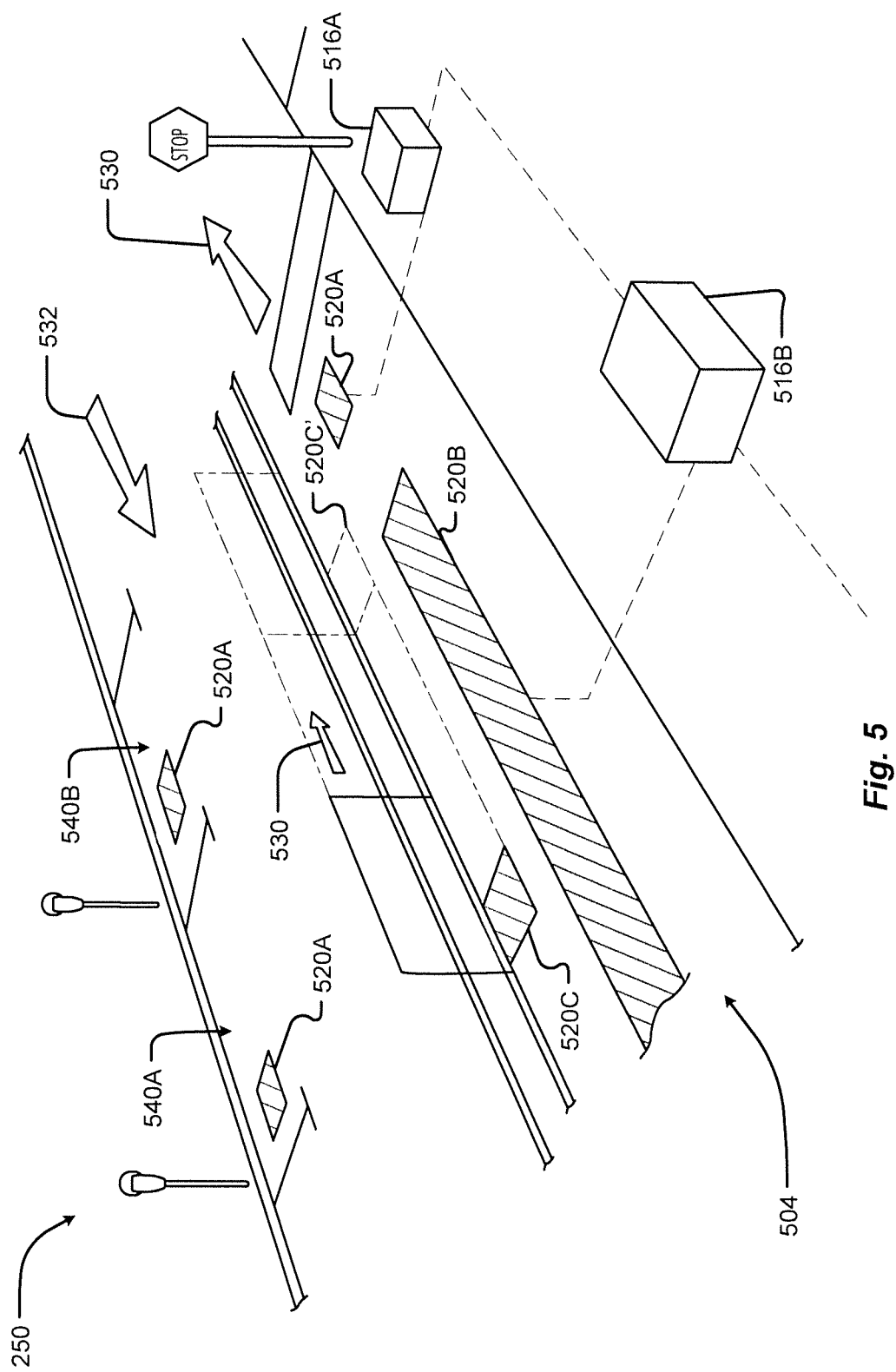
FIG. 5 shows charging areas associated with an environment in accordance with embodiments of the present disclosure.

FIG. 5 depicts a charging environment of a roadway charging system 250. The charging area may be in the roadway 504, on the roadway 504, or otherwise adjacent to the roadway 504, and/or combinations thereof. This static charging area 520B may allow a charge to be transferred even while the electrical vehicle 100 is moving. For example, the static charging area 520B may include a charging transmitter (e.g., conductor, etc.) that provides a transfer of energy when in a suitable range of a receiving unit (e.g., an inductor pick up, etc.). In this example, the receiving unit may be a part of the charging panel associated with the electrical vehicle 100.

The static charging areas 520A, 520B may be positioned a static area such as a designated spot, pad, parking space 540A, 540B, traffic controlled space (e.g., an area adjacent to a stop sign, traffic light, gate, etc.), portion of a building, portion of a structure, etc., and/or combinations thereof. Some static charging areas may require that the electric vehicle 100 is stationary before a charge, or electrical energy transfer, is initiated. The charging of vehicle 100 may occur by any of several means comprising a plug or other protruding feature. The power source 516A, 516B may include a receptacle or other receiving feature, and/or vice versa.

The charging area may be a moving charging area 520C. Moving charging areas 520C may include charging areas associated with one or more portions of a vehicle, a robotic charging device, a tracked charging device, a rail charging device, etc., and/or combinations thereof. In a moving charging area 520C, the electrical vehicle 100 may be configured to receive a charge, via a charging panel, while the vehicle 100 is moving and/or while the vehicle 100 is stationary. In some embodiments, the electrical vehicle 100 may synchronize to move at the same speed, acceleration, and/or path as the moving charging area 520C. In one embodiment, the moving charging area 520C may synchronize to move at the same speed, acceleration, and/or path as the electrical vehicle 100. In any event, the synchronization may be based on an exchange of information communicated across a communications channel between the electric vehicle 100 and the charging area 520C. Additionally or alternatively, the synchronization may be based on information associated with a movement of the electric vehicle 100 and/or the moving charging area 520C. In some embodiments, the moving charging area 520C may be configured to move along a direction or path 532 from an origin position to a destination position 520C'.

In some embodiments, a transformer may be included to convert a power setting associated with a main power supply to a power supply used by the charging areas 520A-C. For example, the transformer may increase or decrease a voltage associated with power supplied via one or more power transmission lines.

Figure 6:
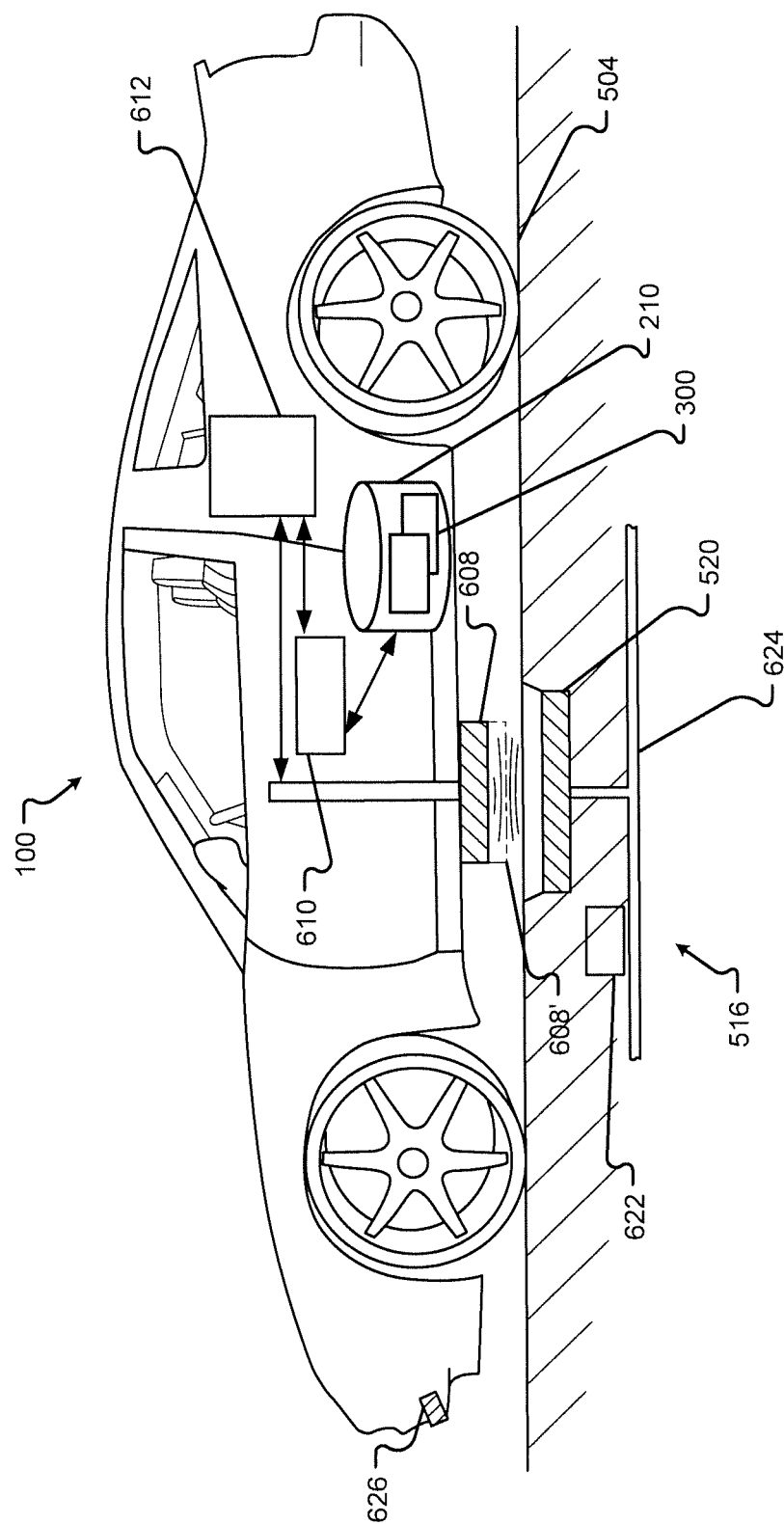
FIG. 6 shows a vehicle in a roadway charging environment in accordance with embodiments of the present disclosure.

Referring to FIG. 6, a vehicle 100 is shown in a charging environment in accordance with embodiments of the present disclosure. The system 10 comprises a vehicle 100, an electrical storage unit 612, an external power source 516 able to provide a charge to the vehicle 100, a charging panel 608 mounted on the vehicle 100 and in electrical communication with the electrical storage unit 612, and a vehicle charging panel controller 610. The charging panel controller 610 may determine if the electrical storage unit requires charging and if conditions allow for deployment of a charging panel. The vehicle charging panel 608 may operate in at least a retracted state and a deployed state (608 and 608' as shown is FIG. 6), and is movable by way of an armature.

The charging panel controller 610 may receive signals from vehicle sensors 626 to determine, for example, if a hazard is present in the path of the vehicle 100 such that deployment of the vehicle charging panel 608 is inadvisable. The charging panel controller 610 may also query vehicle database 210 comprising data structures 300 to establish other required conditions for deployment. For example, the database may provide that a particular roadway does not provide a charging service or the charging service is inactive, wherein the charging panel 108 would not be deployed.

The power source 516 may include at least one electrical transmission line 624 and at least one power transmitter or charging area 520. During a charge, the charging panel 608 may serve to transfer energy from the power source 516 to at least one energy storage unit 612 (e.g., battery, capacitor, power cell, etc.) of the electric vehicle 100.

Figure 7:
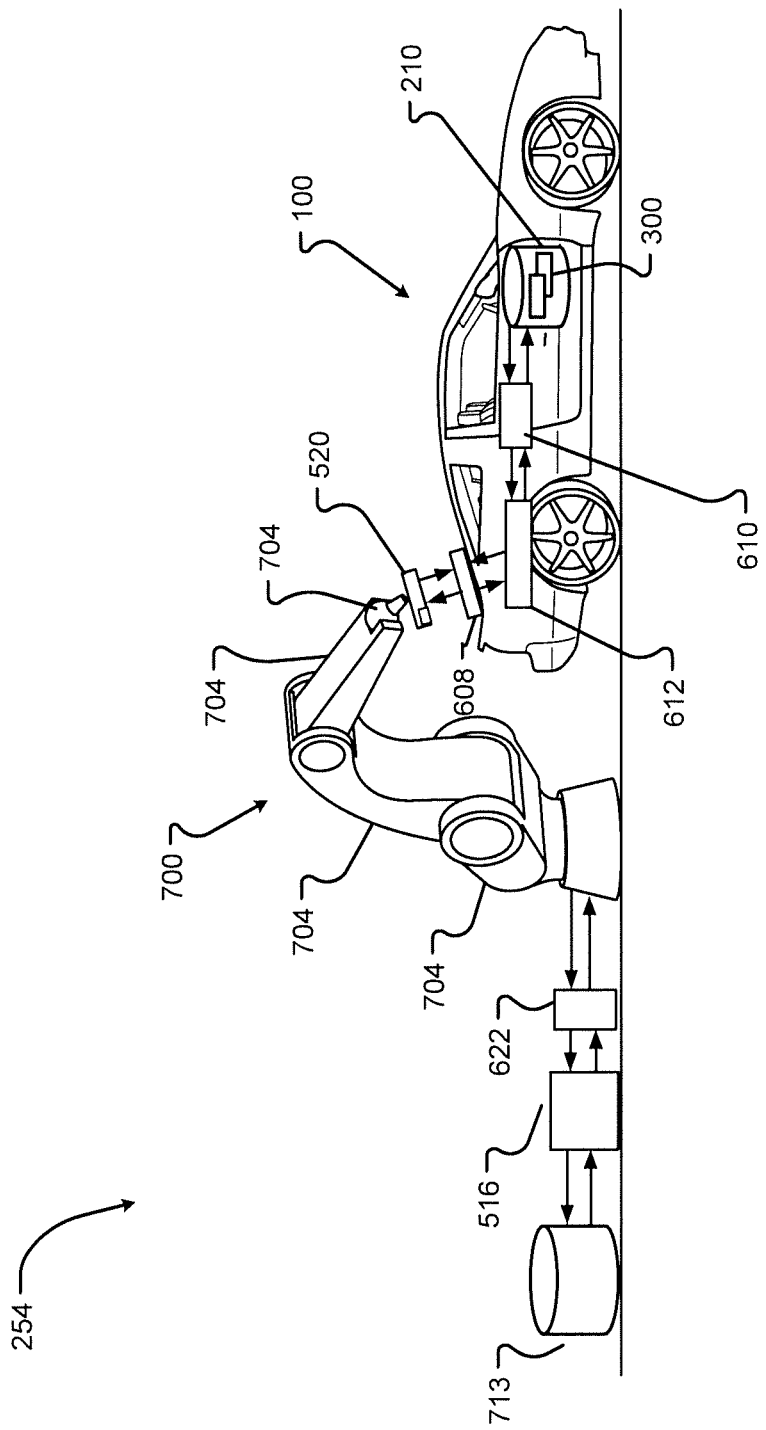
FIG. 7 shows a vehicle in a robotic charging station environment in accordance with another embodiment of the present disclosure.

FIG. 7 shows a vehicle 100 in a charging station environment 254 in accordance with another embodiment of the present disclosure. Generally, in this embodiment of the disclosure, charging occurs from a robotic unit 700.

Robotic charging unit 700 comprises one or more robotic unit arms 704, at least one robotic unit arm 704 interconnected with charging plate 520. The one or more robotic unit arms 704 manoeuver charging plate 520 relative to charging panel 608 of vehicle 100. Charging plate 520 is positioned to a desired or selectable separation distance, as assisted by a separation distance sensor disposed on charging plate 520. Charging plate 520 may remain at a finite separation distance from charging panel 608, or may directly contact charging panel (i.e. such that separation distance is zero). Charging may be by induction. In alternative embodiments, separation distance sensor is alternatively or additionally disposed on robotic arm 704. Vehicle 100 receives charging via charging panel 608 which in turn charges energy storage unit 612. Charging panel controller 610 is in communication with energy storage unit 612, charging panel 608, vehicle database 300, charge provider controller 622, and/or any one of elements of instrument panel 400.

Robotic unit further comprises, is in communication with and/or is interconnected with charge provider controller 622, power source 516 and a robotic unit database. Power source 516 supplies power, such as electrical power, to charge plate 520 to enable charging of vehicle 100 via charging panel 608. Controller 622 manoeuvers or operates robotic unit 704, either directly and/or completely or with assistance from a remote user, such as a driver or passenger in vehicle 100 by way of, in one embodiment, charging manual controller 432.

Figure 8:
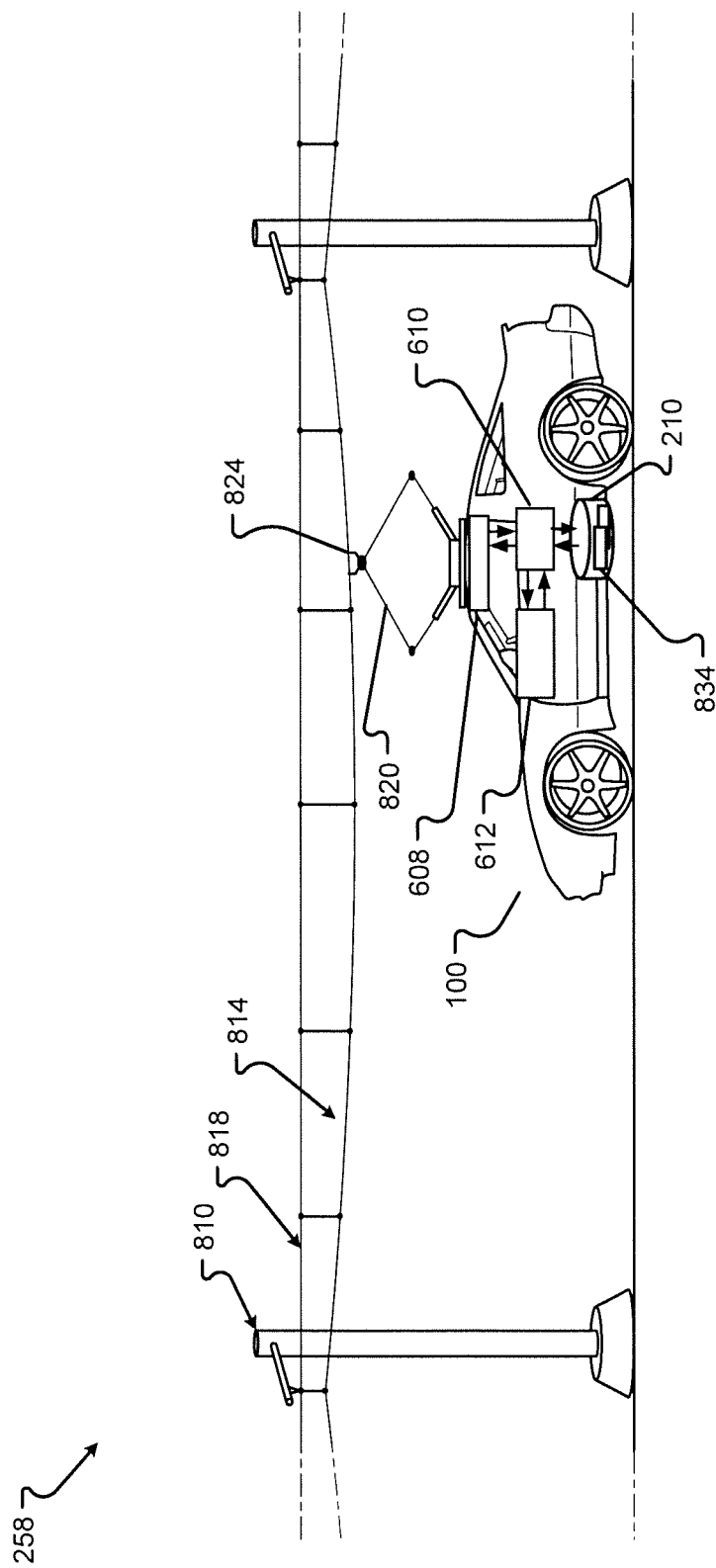
FIG. 8 shows a vehicle in an overhead charging environment in accordance with another embodiment of the present disclosure.

FIG. 8 shows a vehicle 100 in an overhead charging environment in accordance with another embodiment of the present disclosure. Generally, in this embodiment of the disclosure, charging occurs from an overhead towered charging system 258, similar to existing commuter rail systems. Such an overhead towered system 258 may be easier to build and repair compared to in-roadway systems. Generally, the disclosure includes a specially-designed overhead roadway charging system comprising an overhead charging cable or first wire 814 that is configured to engage an overhead contact 824 which provides charge to charging panel 608 which provides charge to vehicle energy storage unit 612. The overhead towered charging system 258 may further comprise second wire 818 to provide stability and structural strength to the roadway charging system 800. The first wire 814 and second wire 818 are strung between towers 810.

The overhead charging cable or first wire 814 is analogous to a contact wire used to provide charging to electric trains or other vehicles. An external source provides or supplies electrical power to the first wire 814. The charge provider comprises an energy source i.e. a provider battery and a provider charge circuit or controller in communication with the provider battery. The overhead charging cable or first wire 814 engages the overhead contact 824 which is in electrical communication with charge receiver panel 108. The overhead contact 824 may comprise any known means to connect to overhead electrical power cables, such as a pantograph 820, a bow collector, a trolley pole or any means known to those skilled in the art. Further disclosure regarding electrical power or energy transfer via overhead systems is found in US Pat. Publ. No. 2013/0105264 to Ruth entitled "Pantograph Assembly," the entire contents of which are incorporated by reference for all purposes. In one embodiment, the charging of vehicle 100 by overhead charging system 800 via overhead contact 824 is by any means know to those skilled in the art, to include those described in the above-referenced US Pat. Publ. No. 2013/0105264 to Ruth.

The overhead contact 824 presses against the underside of the lowest overhead wire of the overhead charging system, i.e. the overhead charging cable or first wire 814, aka the contact wire. The overhead contact 824 may be electrically conductive. Alternatively or additionally, the overhead contact 824 may be adapted to receive electrical power from overhead charging cable or first wire 814 by inductive charging.

In one embodiment, the receipt and/or control of the energy provided via overhead contact 824 (as connected to the energy storage unit 612) is provided by receiver charge circuit or charging panel controller 110.

Overhead contact 824 and/or charging panel 608 may be located anywhere on vehicle 100, to include, for example, the roof, side panel, trunk, hood, front or rear bumper of the charge receiver 100 vehicle, as long as the overhead contact 824 may engage the overhead charging cable or first wire 814. Charging panel 108 may be stationary (e.g. disposed on the roof of vehicle 100) or may be moveable, e.g. moveable with the pantograph 820. Pantograph 820 may be positioned in at least two states comprising retracted and extended. In the extended state pantograph 820 engages first wire 814 by way of the overhead contact 824. In the retracted state, pantograph 820 may typically reside flush with the roof of vehicle 100 and extend only when required for charging. Control of the charging and/or positioning of the charging plate 608, pantograph 820 and/or overhead contact 824 may be manual, automatic or semi-automatic (such as via controller 610); said control may be performed through a GUI engaged by driver or occupant of receiving vehicle 100 and/or driver or occupant of charging vehicle.

Figure 9:
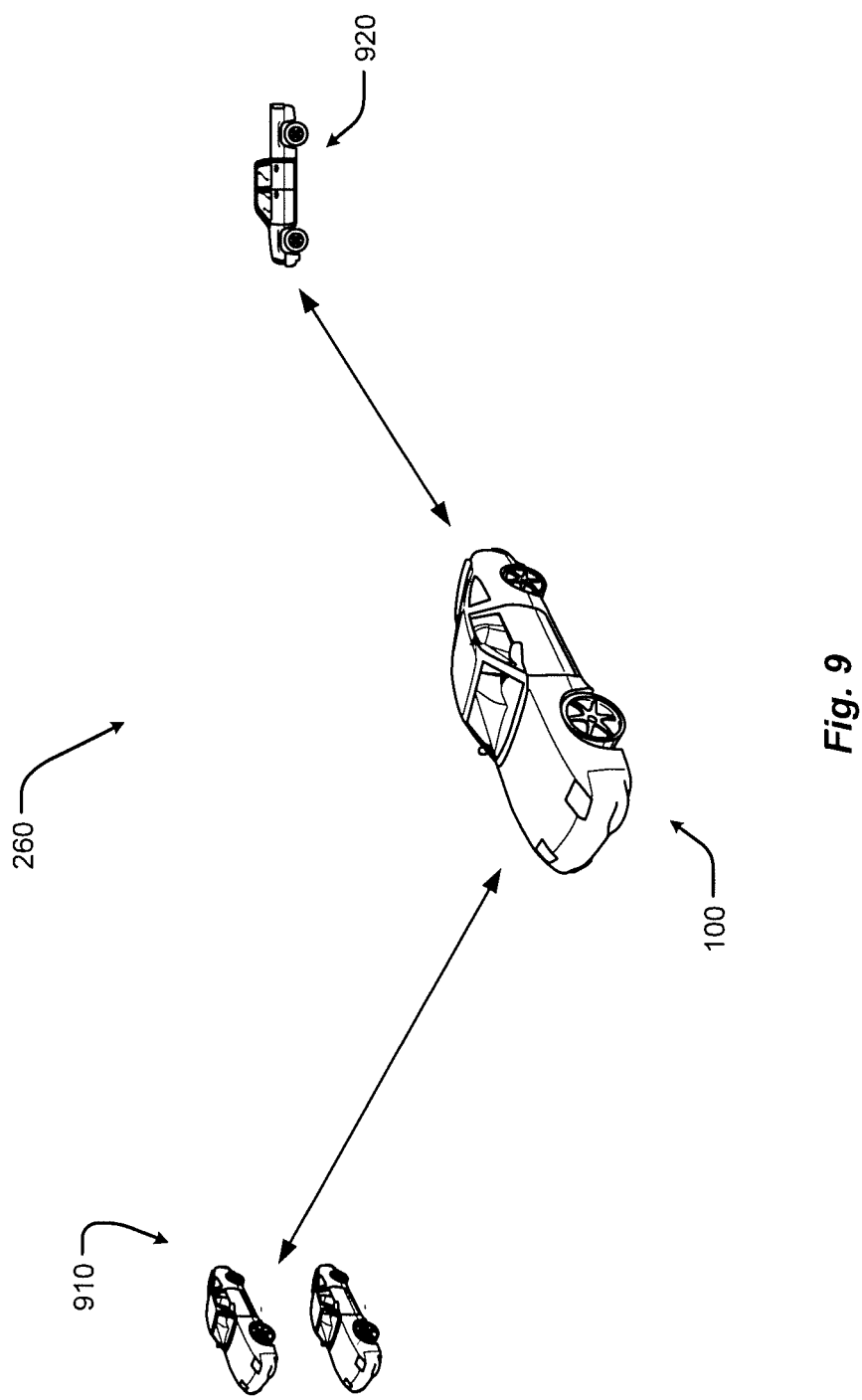
FIG. 9 shows a vehicle in a roadway environment comprising roadway vehicles in accordance with another embodiment of the present disclosure.

FIG. 9 shows a vehicle in a roadway environment comprising roadway vehicles 260 in accordance with another embodiment of the present disclosure. Roadway vehicles 260 comprise roadway passive vehicles 910 and roadway active vehicles 920. Roadway passive vehicles 910 comprise vehicles that are operating on the roadway of vehicle 100 but do no cooperatively or actively engage with vehicle 100. Stated another way, roadway passive vehicles 910 are simply other vehicles operating on the roadway with the vehicle 100 and must be, among other things, avoided (e.g., to include when vehicle 100 is operating in an autonomous or semi-autonomous manner). In contrast, roadway active vehicles 920 comprise vehicles that are operating on the roadway of vehicle 100 and have the capability to, or actually are, actively engaging with vehicle 100. For example, the emergency charging vehicle system 270 is a roadway active vehicle 920 in that it may cooperate or engage with vehicle 100 to provide charging. In some embodiments, vehicle 100 may exchange data with a roadway active vehicle 920 such as, for example, data regarding charging types available to the roadway active vehicle 920.

Figure 10:
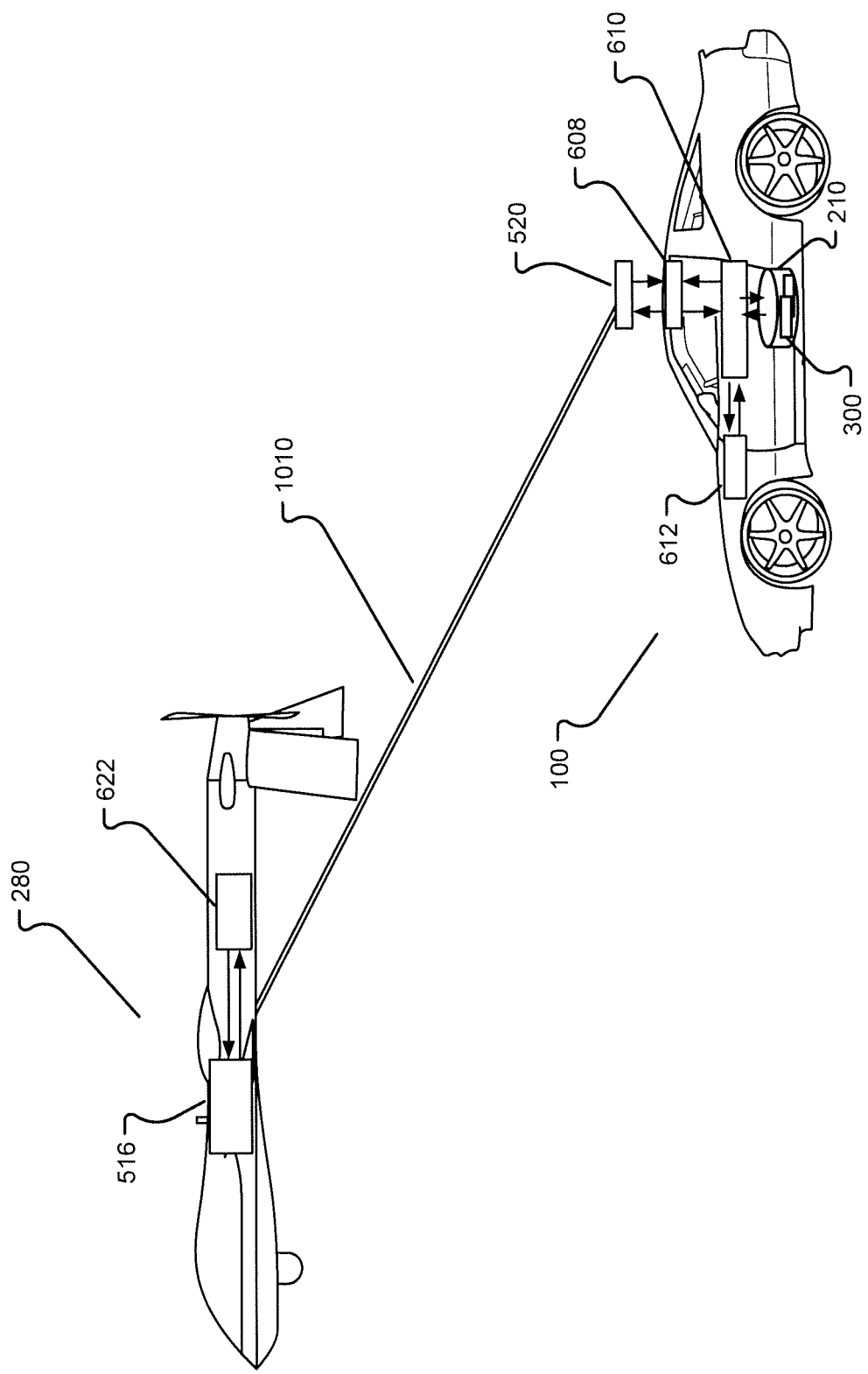
FIG. 10 shows a vehicle in an aerial vehicle charging environment in accordance with another embodiment of the present disclosure.

FIG. 10 shows a vehicle in an aerial vehicle charging environment in accordance with another embodiment of the present disclosure. Generally, this embodiment involves an aerial vehicle ("AV"), such as an Unmanned Aerial Vehicle (UAV), flying over or near a vehicle to provide a charge. The UAV may also land on the car to provide an emergency (or routine) charge. Such a charging scheme may be particularly suited for operations in remote areas, in high traffic situations, and/or when the car is moving. The AV may be a specially-designed UAV, aka RPV or drone, with a charging panel that can extend from the AV to provide a charge. The AV may include a battery pack and a charging circuit to deliver a charge to the vehicle. The AV may be a manned aerial vehicle, such as a piloted general aviation aircraft, such as a Cessna 172.

With reference to FIG. 10, an exemplar embodiment of a vehicle charging system 100 comprising a charge provider configured as an aerial vehicle 280, the aerial vehicle 280 comprising a power source 516 and charge provider controller 622. The AV may be semi-autonomous or fully autonomous. The AV may have a remote pilot/operator providing control inputs. The power source 516 is configured to provide a charge to a charging panel 608 of vehicle 100. The power source 516 is in communication with the charge provider controller 622. The aerial vehicle 280 provides a tether 1010 to deploy or extend charging plate 520 near to charging panel 608. The tether 1010 may comprise a chain, rope, rigid or semi-rigid tow bar or any means to position charging plate 520 near charging panel 608. For example, tether 1010 may be similar to a refueling probe used by airborne tanker aircraft when refueling another aircraft.

In one embodiment, the charging plate 520 is not in physical interconnection to AV 280, that is, there is no tether

1010. In this embodiment, the charging plate 520 is positioned and controlled by AV 280 by way of a controller on AV 280 or in communication with AV 280.

In one embodiment, the charging plate 520 position and/or characteristics (e.g. charging power level, flying separation distance, physical engagement on/off) are controlled by vehicle 100 and/or a user in or driver of vehicle 100.

Charge or power output of power source 516 is provided or transmitted to charger plate 620 by way of a charging cable or wire, which may be integral to tether 1010. In one embodiment, the charging cable is non-structural, that is, it provides zero or little structural support to the connection between AV 280 and charger plate 520.

Charging panel 608 of vehicle 100 receives power from charger plate 520. Charging panel 608 and charger plate 520 may be in direct physical contact (termed a "contact" charger configuration) or not in direct physical contact (termed a "flyer" charger configuration), but must be at or below a threshold (separation) distance to enable charging, such as by induction. Energy transfer or charging from the charger plate 520 to the charging panel 608 is inductive charging (i.e. use of an EM field to transfer energy between two objects). The charging panel 608 provides received power to energy storage unit 612 by way of charging panel controller 610. Charging panel controller 610 is in communication with vehicle database 210, vehicle database 210 comprising an AV charging data structure.

Charging panel 508 may be located anywhere on vehicle 100, to include, for example, the roof, side panel, trunk, hood, front or rear bumper and wheel hub of vehicle 100. Charging panel 608 is mounted on the roof of vehicle 100 in the embodiment of FIG. 10. In some embodiments, charging panel 608 may be deployable, i.e. may extend or deploy only when charging is needed. For example, charging panel 608 may typically reside flush with the roof of vehicle 100 and extend when required for charging. Similarly, charger plate 520 may, in one embodiment, not be connected to AV 280 by way of tether 1010 and may instead be mounted directly on the AV 280, to include, for example, the wing, empennage, undercarriage to include landing gear, and may be deployable or extendable when required. Tether 1010 may be configured to maneuver charging plate 520 to any position on vehicle 100 so as to enable charging. In one embodiment, the AV 280 may land on the vehicle 100 so as to enable charging through direct contact (i.e. the aforementioned contact charging configuration) between the charging plate 520 and the charging panel 608 of vehicle 100. Charging may occur while both AV 280 and vehicle 100 are moving, while both vehicle 100 and AV 280 are not moving (i.e., vehicle 100 is parked and AV 280 lands on top of vehicle 100), or while vehicle 100 is parked and AV 280 is hovering or circling above. Control of the charging and/or positioning of the charging plate 520 may be manual, automatic or semi-automatic; said control may be performed through a GUI engaged by driver or occupant of receiving vehicle 100 and/or driver or occupant of charging AV 280.

Figure 11:
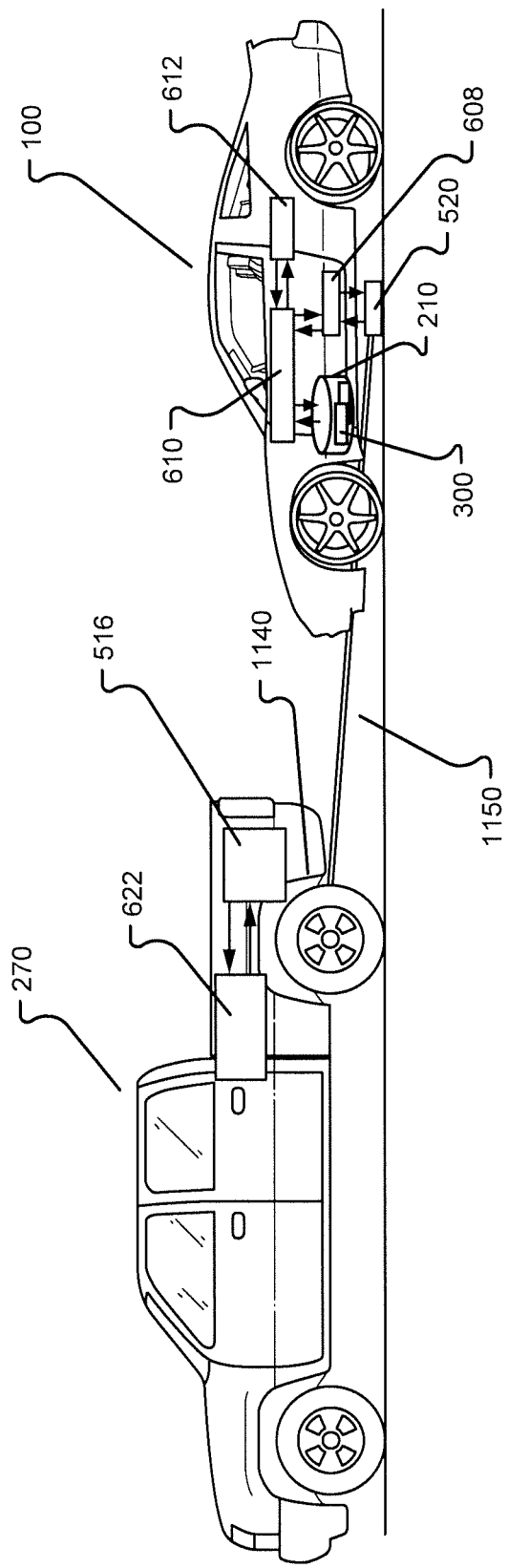
FIG. 11 shows a vehicle in an emergency charging environment in accordance with embodiments of the present disclosure.

FIG. 11 is an embodiment of a vehicle emergency charging system comprising an emergency charging vehicle 270 and charge receiver vehicle 100 is disclosed. The emergency charging vehicle 270 is a road vehicle, such as a pick-up truck, as shown in FIG. 11. The emergency charging vehicle 270 is configured to provide a charge to a charge receiver vehicle 100, such as an automobile. The emergency charging vehicle 270 comprises an energy source i.e. a charging power source 516 and a charge provider controller 622 in communication with the charging power source 516. The emergency charging vehicle 270 provides a towed and/or articulated charger plate 520, as connected to the emergency charging vehicle 270 by connector 1150. The connector 1150 may comprise a chain, rope, rigid or semi-rigid tow bar or any means to position charger plate 520 near the charging panel 608 of vehicle 100. Charge or power output of charging power source 516 is provided or transmitted to charger plate 520 by way of charging cable or wire 1140. In one embodiment, the charging cable 1140 is non-structural, that is, it provides little or no structural support to the connection between emergency charging vehicle 270 and charging panel 608. Charging panel 608 (of vehicle 100) receives power from charger plate 520. Charger plate 520 and charging panel 608 may be in direct physical contact or not in direct physical contact, but must be at or below a threshold separation distance to enable charging, such as by induction. Charger plate 520 may comprise wheels or rollers so as to roll along roadway surface. Charger plate 520 may also not contact the ground surface and instead be suspended above the ground; such a configuration may be termed a "flying" configuration. In the flying configuration, charger plate may form an aerodynamic surface to, for example, facilitate stability and control of the positioning of the charging plate 520. Energy transfer or charging from the charger plate 520 to the charge receiver panel 608 is through inductive charging (i.e. use of an EM field to transfer energy between two objects). The charging panel 608 provides received power to energy storage unit 612 directly or by way of charging panel controller 610. In one embodiment, the receipt and/or control of the energy provided via the charging panel 608 is provided by charging panel controller 610.

Charging panel controller 610 may be located anywhere on charge receiver vehicle 100, to include, for example, the roof, side panel, trunk, hood, front or rear bumper and wheel hub of charge receiver 100 vehicle. In some embodiments, charging panel 608 may be deployable, i.e. may extend or deploy only when charging is needed. For example, charging panel 608 may typically stow flush with the lower plane of vehicle 100 and extend when required for charging. Similarly, charger plate 520 may, in one embodiment, not be connected to the lower rear of the emergency charging vehicle 270 by way of connector 1150 and may instead be mounted on the emergency charging vehicle 270, to include, for example, the roof, side panel, trunk, hood, front or rear bumper and wheel hub of emergency charging vehicle 270. Connector 1150 may be configured to maneuver connector plate 520 to any position on emergency charging vehicle 270 so as to enable charging. Control of the charging and/or positioning of the charging plate may be manual, automatic or semi-automatic; said control may be performed through a GUI engaged by driver or occupant of receiving vehicle and/or driver or occupant of charging vehicle.

Figure 12:
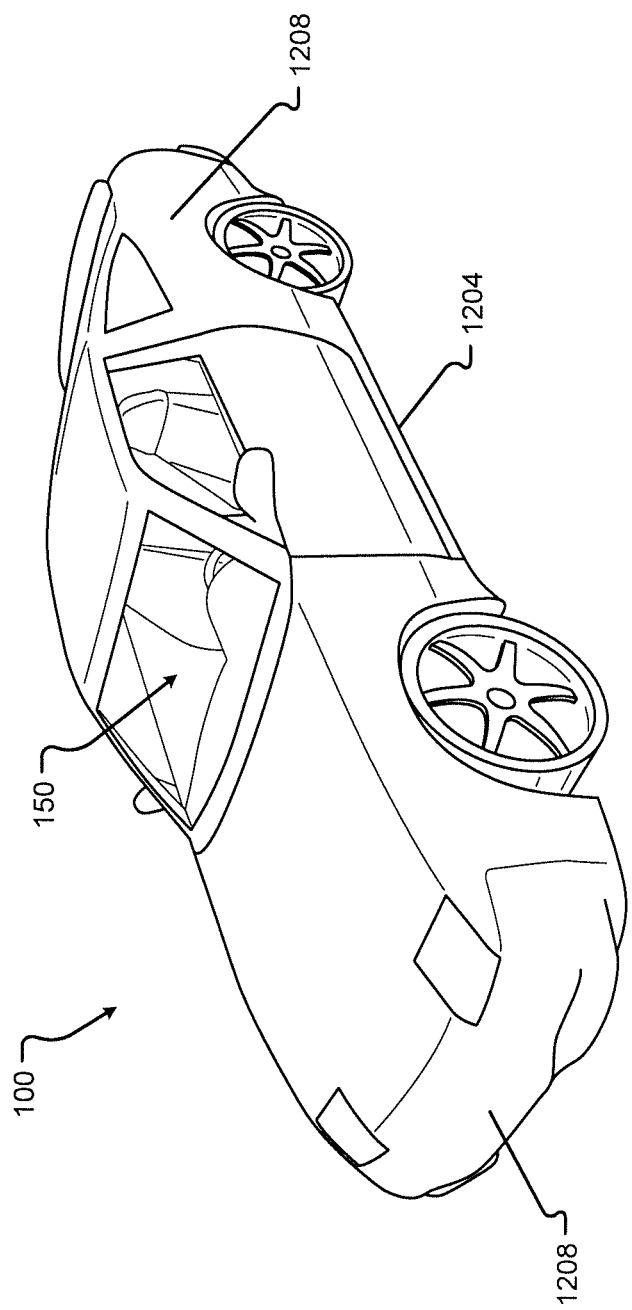
FIG. 12 is a perspective view of a vehicle in accordance with embodiments of the present disclosure.

FIG. 12 shows a perspective view of a vehicle 100 in accordance with embodiments of the present disclosure. Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like. In any event, the vehicle 100 may include a frame 1204 and one or more body panels 1208 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components.

Figure 13:
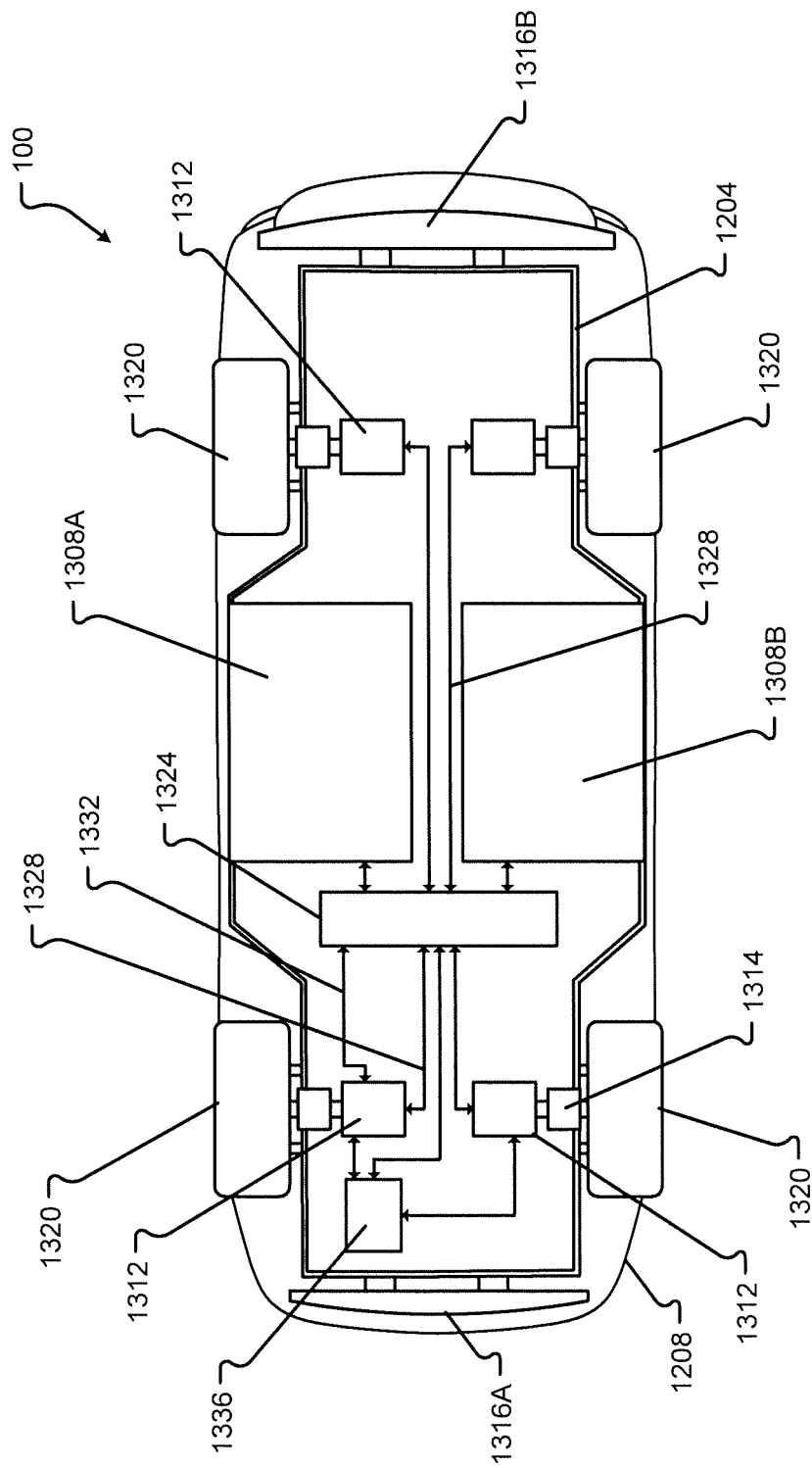
FIG. 13 is a plan view of a vehicle in accordance with at least some embodiments of the present disclosure.

Referring now to FIG. 13, a plan view of a vehicle 100 will be described in accordance with embodiments of the present disclosure. As provided above, the vehicle 100 may comprise a number of electrical and/or mechanical systems, subsystems, etc. The mechanical systems of the vehicle 100 can include structural, power, safety, and communications subsystems, to name a few. While each subsystem may be described separately, it should be appreciated that the components of a particular subsystem may be shared between one or more other subsystems of the vehicle 100.

The structural subsystem includes the frame 1204 of the vehicle 100. The frame 1204 may comprise a separate frame and body construction (i.e., body-on-frame construction), a unitary frame and body construction (i.e., a unibody construction), or any other construction defining the structure of the vehicle 100. The frame 1204 may be made from one or more materials including, but in no way limited to steel, titanium, aluminum, carbon fiber, plastic, polymers, etc., and/or combinations thereof. In some embodiments, the frame 1204 may be formed, welded, fused, fastened, pressed, etc., combinations thereof, or otherwise shaped to define a physical structure and strength of the vehicle 100. In any event, the frame 1204 may comprise one or more surfaces, connections, protrusions, cavities, mounting points, tabs, slots, or other features that are configured to receive other components that make up the vehicle 100. For example, the body panels, powertrain subsystem, controls systems, interior components, communications subsystem, and safety subsystem may interconnect with, or attach to, the frame 1204 of the vehicle 100.

The frame 1204 may include one or more modular system and/or subsystem connection mechanisms. These mechanisms may include features that are configured to provide a selectively interchangeable interface for one or more of the systems and/or subsystems described herein. The mechanisms may provide for a quick exchange, or swapping, of components while providing enhanced security and adaptability over conventional manufacturing or attachment. For instance, the ability to selectively interchange systems and/or subsystems in the vehicle 100 allow the vehicle 100 to adapt to the ever-changing technological demands of society and advances in safety. Among other things, the mechanisms may provide for the quick exchange of batteries, capacitors, power sources 1308A, 1308B, motors 1312, engines, safety equipment, controllers, user interfaces, interiors exterior components, body panels 1208, bumpers 1316, sensors, etc., and/or combinations thereof. Additionally or alternatively, the mechanisms may provide unique security hardware and/or software embedded therein that, among other things, can prevent fraudulent or low quality construction replacements from being used in the vehicle 100. Similarly, the mechanisms, subsystems, and/or receiving features in the vehicle 100 may employ poka-yoke, or mistake-proofing, features that ensure a particular mechanism is always interconnected with the vehicle 100 in a correct position, function, etc.

By way of example, complete systems or subsystems may be removed and/or replaced from a vehicle 100 utilizing a single minute exchange principle. In some embodiments, the frame 1204 may include slides, receptacles, cavities, protrusions, and/or a number of other features that allow for quick exchange of system components. In one embodiment, the frame 1204 may include tray or ledge features, mechanical interconnection features, locking mechanisms, retaining mechanisms, etc., and/or combinations thereof. In some embodiments, it may be beneficial to quickly remove a used power source 1308A, 1308B (e.g., battery unit, capacitor unit, etc.) from the vehicle 100 and replace the used power source 1308A, 1308B with a charged power source. Continuing this example, the power source 1308A, 1308B may include selectively interchangeable features that interconnect with the frame 1204 or other portion of the vehicle 100. For instance, in a power source 1308A, 1308B replacement, the quick release features may be configured to release the power source 1308A, 1308B from an engaged position and slide or move away from the frame 1204 of a vehicle 100. Once removed, the power source 1308A, 1308B may be replaced (e.g., with a new power source, a charged power source, etc.) by engaging the replacement power source into a system receiving position adjacent to the vehicle 100. In some embodiments, the vehicle 100 may include one or more actuators configured to position, lift, slide, or otherwise engage the replacement power source with the vehicle 100. In one embodiment, the replacement power source may be inserted into the vehicle 100 or vehicle frame 1204 with mechanisms and/or machines that are external or separate from the vehicle 100.

In some embodiments, the frame 1204 may include one or more features configured to selectively interconnect with other vehicles and/or portions of vehicles. These selectively interconnecting features can allow for one or more vehicles to selectively couple together and decouple for a variety of purposes. For example, it is an aspect of the present disclosure that a number of vehicles may be selectively coupled together to share energy, increase power output, provide security, decrease power consumption, provide towing services, and/or provide a range of other benefits. Continuing this example, the vehicles may be coupled together based on travel route, destination, preferences, settings, sensor information, and/or some other data. The coupling may be initiated by at least one controller of the vehicle and/or traffic control system upon determining that a coupling is beneficial to one or more vehicles in a group of vehicles or a traffic system. As can be appreciated, the power consumption for a group of vehicles traveling in a same direction may be reduced or decreased by removing any aerodynamic separation between vehicles. In this case, the vehicles may be coupled together to subject only the foremost vehicle in the coupling to air and/or wind resistance during travel. In one embodiment, the power output by the group of vehicles may be proportionally or selectively controlled to provide a specific output from each of the one or more of the vehicles in the group.

The interconnecting, or coupling, features may be configured as electromagnetic mechanisms, mechanical couplings, electromechanical coupling mechanisms, etc., and/or combinations thereof. The features may be selectively deployed from a portion of the frame 1204 and/or body of the vehicle 100. In some cases, the features may be built into the frame 1204 and/or body of the vehicle 100. In any event, the features may deploy from an unexposed position to an exposed position or may be configured to selectively engage/disengage without requiring an exposure or deployment of the mechanism from the frame 1204 and/or body. In some embodiments, the interconnecting features may be configured to interconnect one or more of power, communications, electrical energy, fuel, and/or the like. One or more of the power, mechanical, and/or communications connections between vehicles may be part of a single interconnection mechanism. In some embodiments, the interconnection mechanism may include multiple connection mechanisms. In any event, the single interconnection mechanism or the interconnection mechanism may employ the poka-yoke features as described above.

The power system of the vehicle 100 may include the powertrain, power distribution system, accessory power system, and/or any other components that store power, provide power, convert power, and/or distribute power to one or more portions of the vehicle 100. The powertrain may include the one or more electric motors 1312 of the vehicle 100. The electric motors 1312 are configured to convert electrical energy provided by a power source into mechanical energy. This mechanical energy may be in the form of a rotational or other output force that is configured to propel or otherwise provide a motive force for the vehicle 100.

In some embodiments, the vehicle 100 may include one or more drive wheels 1320 that are driven by the one or more electric motors 1312 and motor controllers 1314. In some cases, the vehicle 100 may include an electric motor 1312 configured to provide a driving force for each drive wheel 1320. In other cases, a single electric motor 1312 may be configured to share an output force between two or more drive wheels 1320 via one or more power transmission components. It is an aspect of the present disclosure that the powertrain include one or more power transmission components, motor controllers 1314, and/or power controllers that can provide a controlled output of power to one or more of the drive wheels 1320 of the vehicle 100. The power transmission components, power controllers, or motor controllers 1314 may be controlled by at least one other vehicle controller described herein.

As provided above, the powertrain of the vehicle 100 may include one or more power sources 1308A, 1308B. These one or more power sources 1308A, 1308B may be configured to provide drive power, system and/or subsystem power, accessory power, etc. While described herein as a single power source 1308 for sake of clarity, embodiments of the present disclosure are not so limited. For example, it should be appreciated that independent, different, or separate power sources 1308A, 1308B may provide power to various systems of the vehicle 100. For instance, a drive power source may be configured to provide the power for the one or more electric motors 1312 of the vehicle 100, while a system power source may be configured to provide the power for one or more other systems and/or subsystems of the vehicle 100. Other power sources may include an accessory power source, a backup power source, a critical system power source, and/or other separate power sources. Separating the power sources 1308A, 1308B in this manner may provide a number of benefits over conventional vehicle systems. For example, separating the power sources 1308A, 1308B allow one power source 1308 to be removed and/or replaced independently without requiring that power be removed from all systems and/or subsystems of the vehicle 100 during a power source 1308 removal/replacement. For instance, one or more of the accessories, communications, safety equipment, and/or backup power systems, etc., may be maintained even when a particular power source 1308A, 1308B is depleted, removed, or becomes otherwise inoperable.

In some embodiments, the drive power source may be separated into two or more cells, units, sources, and/or systems. By way of example, a vehicle 100 may include a first drive power source 1308A and a second drive power source 1308B. The first drive power source 1308A may be operated independently from or in conjunction with the second drive power source 1308B and vice versa. Continuing this example, the first drive power source 1308A may be removed from a vehicle while a second drive power source 1308B can be maintained in the vehicle 100 to provide drive power. This approach allows the vehicle 100 to significantly reduce weight (e.g., of the first drive power source 1308A, etc.) and improve power consumption, even if only for a temporary period of time. In some cases, a vehicle 100 running low on power may automatically determine that pulling over to a rest area, emergency lane, and removing, or "dropping off," at least one power source 1308A, 1308B may reduce enough weight of the vehicle 100 to allow the vehicle 100 to navigate to the closest power source replacement and/or charging area. In some embodiments, the removed, or "dropped off," power source 1308A may be collected by a collection service, vehicle mechanic, tow truck, or even another vehicle or individual.

The power source 1308 may include a GPS or other geographical location system that may be configured to emit a location signal to one or more receiving entities. For instance, the signal may be broadcast or targeted to a specific receiving party. Additionally or alternatively, the power source 1308 may include a unique identifier that may be used to associate the power source 1308 with a particular vehicle 100 or vehicle user. This unique identifier may allow an efficient recovery of the power source 1308 dropped off. In some embodiments, the unique identifier may provide information for the particular vehicle 100 or vehicle user to be billed or charged with a cost of recovery for the power source 1308.

The power source 1308 may include a charge controller 1324 that may be configured to determine charge levels of the power source 1308, control a rate at which charge is drawn from the power source 1308, control a rate at which charge is added to the power source 1308, and/or monitor a health of the power source 1308 (e.g., one or more cells, portions, etc.). In some embodiments, the charge controller 1324 or the power source 1308 may include a communication interface. The communication interface can allow the charge controller 1324 to report a state of the power source 1308 to one or more other controllers of the vehicle 100 or even communicate with a communication device separate and/or apart from the vehicle 100. Additionally or alternatively, the communication interface may be configured to receive instructions (e.g., control instructions, charge instructions, communication instructions, etc.) from one or more other controllers of the vehicle 100 or a communication device that is separate and/or apart from the vehicle 100.

The powertrain includes one or more power distribution systems configured to transmit power from the power source 1308 to one or more electric motors 1312 in the vehicle 100. The power distribution system may include electrical interconnections 1328 in the form of cables, wires, traces, wireless power transmission systems, etc., and/or combinations thereof. It is an aspect of the present disclosure that the vehicle 100 include one or more redundant electrical interconnections 1332 of the power distribution system. The redundant electrical interconnections 1332 can allow power to be distributed to one or more systems and/or subsystems of the vehicle 100 even in the event of a failure of an electrical interconnection portion of the vehicle 100 (e.g., due to an accident, mishap, tampering, or other harm to a particular electrical interconnection, etc.). In some embodiments, a user of a vehicle 100 may be alerted via a user interface associated with the vehicle 100 that a redundant electrical interconnection 1332 is being used and/or damage has occurred to a particular area of the vehicle electrical system. In any event, the one or more redundant electrical interconnections 1332 may be configured along completely different routes than the electrical interconnections 1328 and/or include different modes of failure than the electrical interconnections 1328 to, among other things, prevent a total interruption power distribution in the event of a failure.

In some embodiments, the power distribution system may include an energy recovery system 1336. This energy recovery system 1336, or kinetic energy recovery system, may be configured to recover energy produced by the movement of a vehicle 100. The recovered energy may be stored as electrical and/or mechanical energy. For instance, as a vehicle 100 travels or moves, a certain amount of energy is required to accelerate, maintain a speed, stop, or slow the vehicle 100. In any event, a moving vehicle has a certain amount of kinetic energy. When brakes are applied in a typical moving vehicle, most of the kinetic energy of the vehicle is lost as the generation of heat in the braking mechanism. In an energy recovery system 1336, when a vehicle 100 brakes, at least a portion of the kinetic energy is converted into electrical and/or mechanical energy for storage. Mechanical energy may be stored as mechanical movement (e.g., in a flywheel, etc.) and electrical energy may be stored in batteries, capacitors, and/or some other electrical storage system. In some embodiments, electrical energy recovered may be stored in the power source 1308. For example, the recovered electrical energy may be used to charge the power source 1308 of the vehicle 100.

The vehicle 100 may include one or more safety systems. Vehicle safety systems can include a variety of mechanical and/or electrical components including, but in no way limited to, low impact or energy-absorbing bumpers 1316A, 1316B, crumple zones, reinforced body panels, reinforced frame components, impact bars, power source containment zones, safety glass, seatbelts, supplemental restraint systems, air bags, escape hatches, removable access panels, impact sensors, accelerometers, vision systems, radar systems, etc., and/or the like. In some embodiments, the one or more of the safety components may include a safety sensor or group of safety sensors associated with the one or more of the safety components. For example, a crumple zone may include one or more strain gages, impact sensors, pressure transducers, etc. These sensors may be configured to detect or determine whether a portion of the vehicle 100 has been subjected to a particular force, deformation, or other impact. Once detected, the information collected by the sensors may be transmitted or sent to one or more of a controller of the vehicle 100 (e.g., a safety controller, vehicle controller, etc.) or a communication device associated with the vehicle 100 (e.g., across a communication network, etc.).

Figure 14:
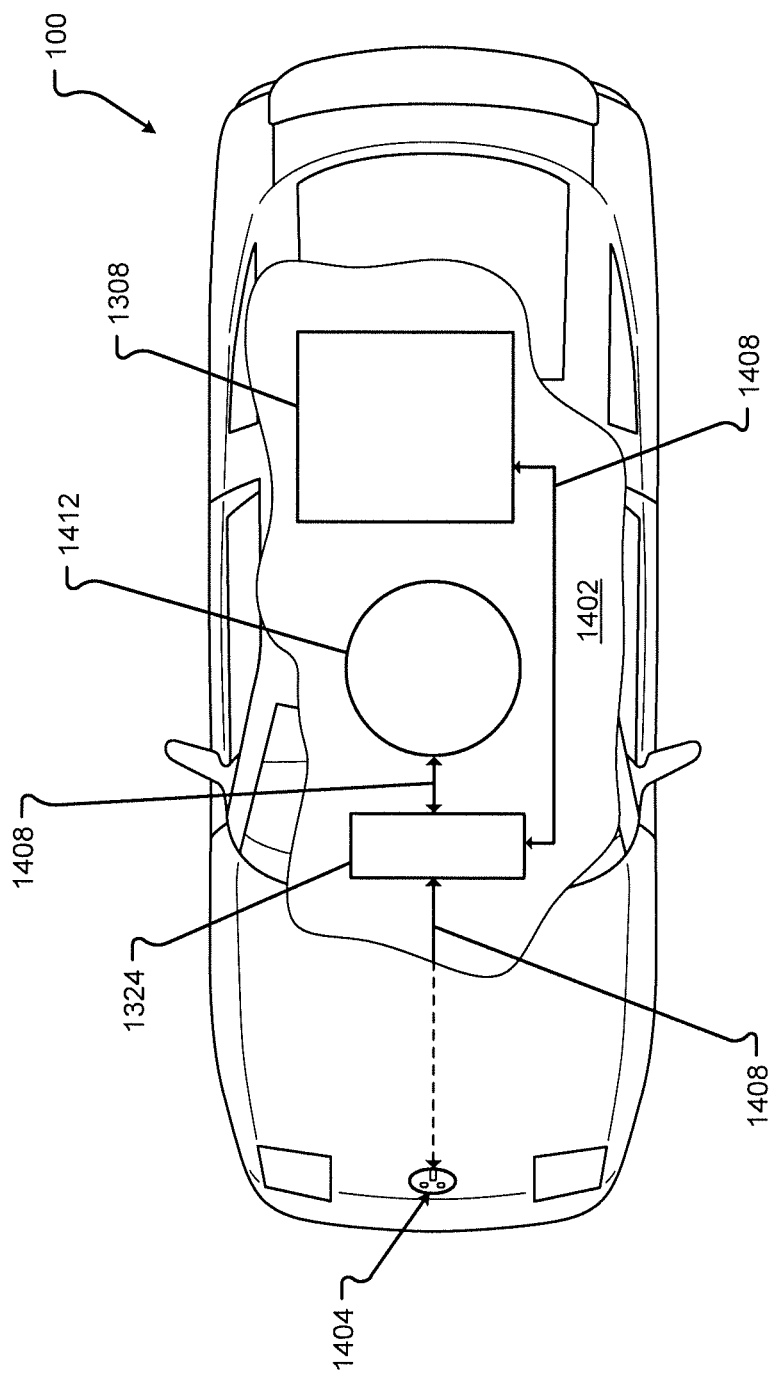
FIG. 14 is a plan view of a vehicle in accordance with embodiments of the present disclosure.

FIG. 14 shows a plan view of the vehicle 100 in accordance with embodiments of the present disclosure. In particular, FIG. 14 shows a broken section 1402 of a charging system for the vehicle 100. The charging system may include a plug or receptacle 1404 configured to receive power from an external power source (e.g., a source of power that is external to and/or separate from the vehicle 100, etc.). An example of an external power source may include the standard industrial, commercial, or residential power that is provided across power lines. Another example of an external power source may include a proprietary power system configured to provide power to the vehicle 100. In any event, power received at the plug/receptacle 1404 may be transferred via at least one power transmission interconnection 1408. Similar, if not identical, to the electrical interconnections 1328 described above, the at least one power transmission interconnection 1408 may be one or more cables, wires, traces, wireless power transmission systems, etc., and/or combinations thereof. Electrical energy in the form of charge can be transferred from the external power source to the charge controller 1324. As provided above, the charge controller 1324 may regulate the addition of charge to the power source 1308 of the vehicle 100 (e.g., until the power source 1308 is full or at a capacity, etc.).

In some embodiments, the vehicle 100 may include an inductive charging system and inductive charger 1412. The inductive charger 1412 may be configured to receive electrical energy from an inductive power source external to the vehicle 100. In one embodiment, when the vehicle 100 and/or the inductive charger 1412 is positioned over an inductive power source external to the vehicle 100, electrical energy can be transferred from the inductive power source to the vehicle 100. For example, the inductive charger 1412 may receive the charge and transfer the charge via at least one power transmission interconnection 1408 to the charge controller 1324 and/or the power source 1308 of the vehicle 100. The inductive charger 1412 may be concealed in a portion of the vehicle 100 (e.g., at least partially protected by the frame 1204, one or more body panels 1208, a shroud, a shield, a protective cover, etc., and/or combinations thereof) and/or may be deployed from the vehicle 100. In some embodiments, the inductive charger 1412 may be configured to receive charge only when the inductive charger 1412 is deployed from the vehicle 100. In other embodiments, the inductive charger 1412 may be configured to receive charge while concealed in the portion of the vehicle 100.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 15:
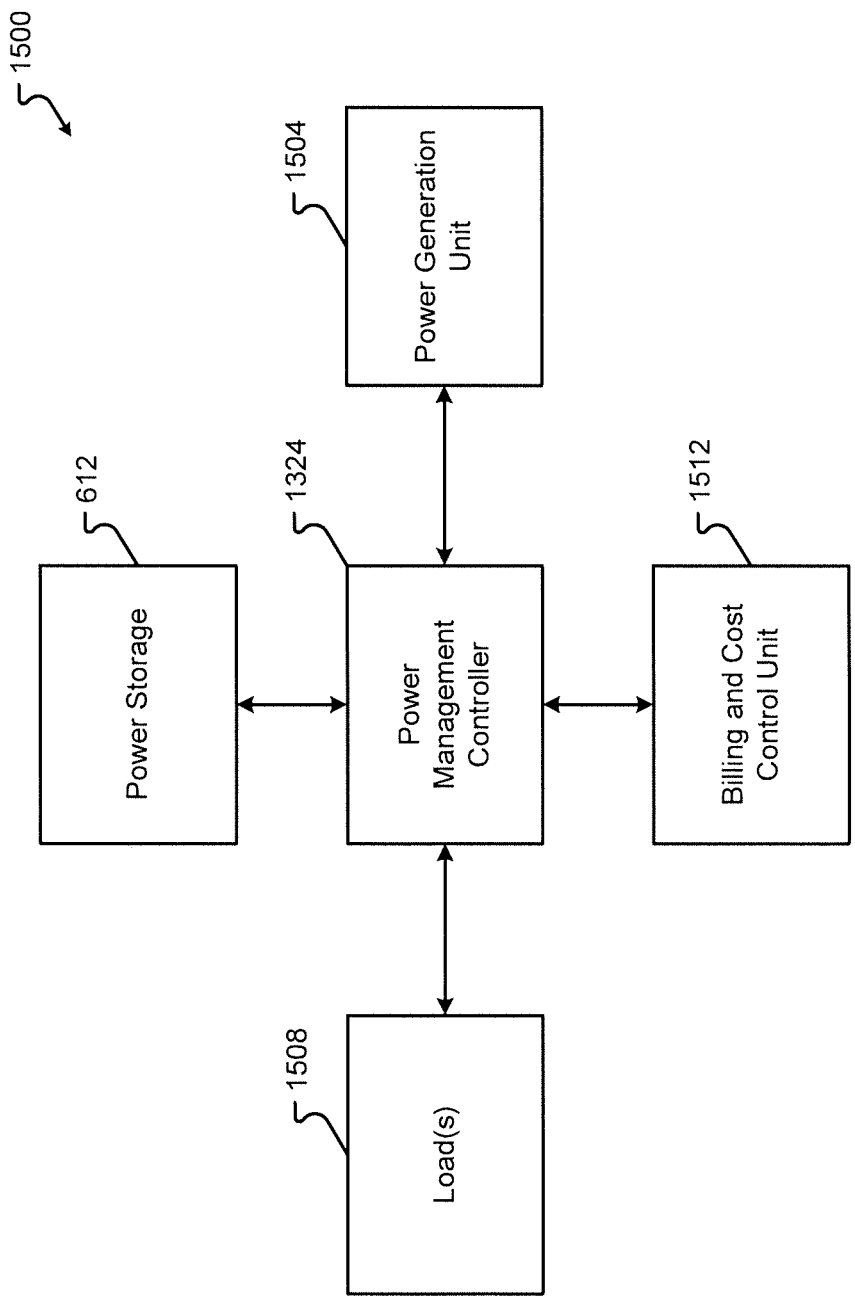
FIG. 15 is a block diagram of an embodiment of an electrical system of the vehicle.

An embodiment of the electrical system 1500 associated with the vehicle 100 may be as shown in FIG. 15. The electrical system 1500 can include power source(s) that generate power, power storage that stores power, and/or load(s) that consume power. Power sources may be associated with a power generation unit 1504. Power storage may be associated with a power storage system 612. Loads may be associated with loads 1508. The electrical system 1500 may be managed by a power management controller 1324. Further, the electrical system 1500 can include one or more other interfaces or controllers, which can include the billing and cost control unit 1512.

Figure 16:
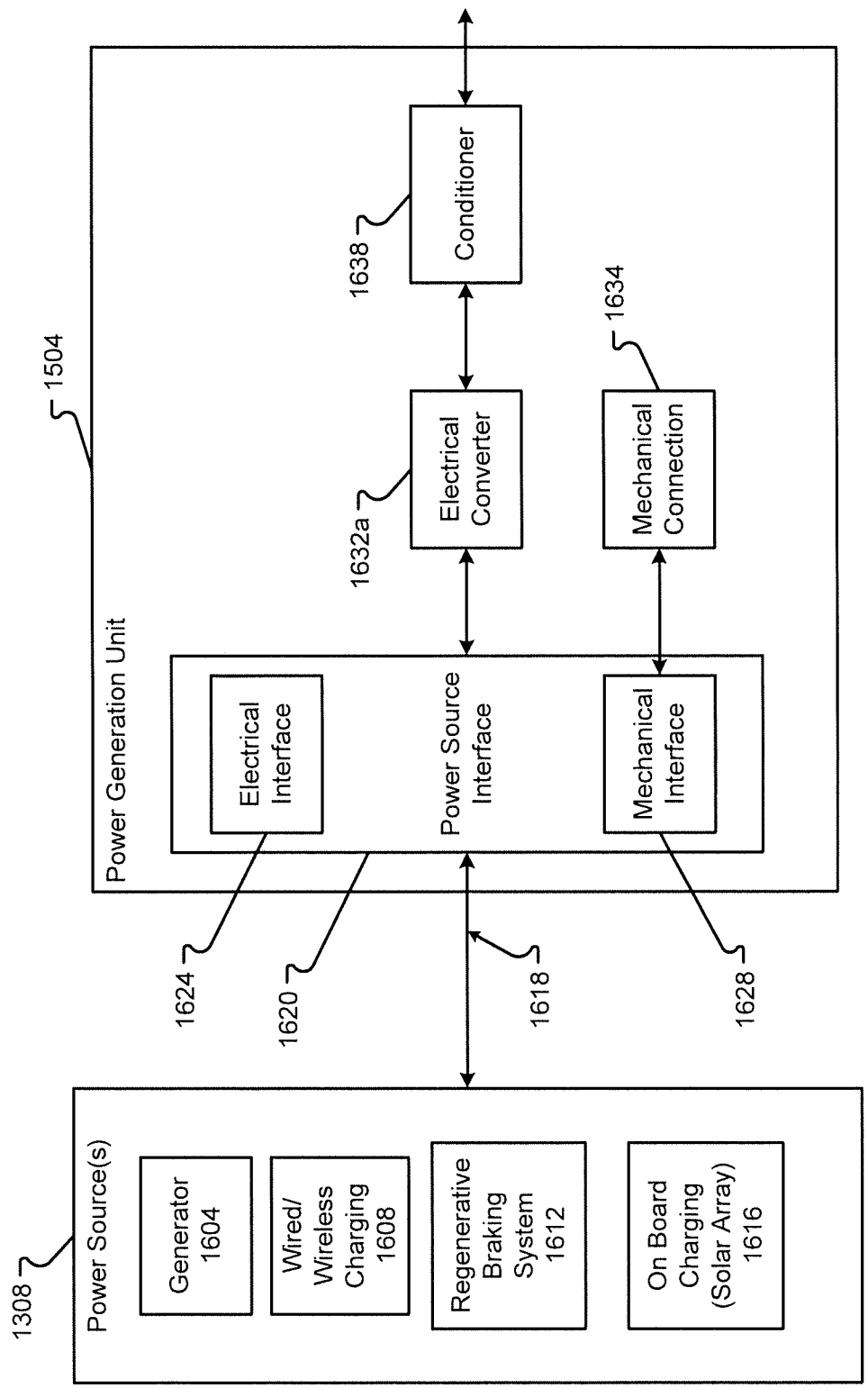
FIG. 16 is a block diagram of an embodiment of a power generation unit associated with the electrical system of the vehicle.

The power generation unit 1504 may be as described in conjunction with FIG. 16. The power storage component 612 may be as described in conjunction with FIG. 17. The loads 1508 may be as described in conjunction with FIG. 18.

The billing and cost control unit 1512 may interface with the power management controller 1324 to determine the amount of charge or power provided to the power storage 612 through the power generation unit 1504. The billing and cost control unit 1512 can then provide information for billing the vehicle owner. Thus, the billing and cost control unit 1512 can receive and/or send power information to third party system(s) regarding the received charge from an external source. The information provided can help determine an amount of money required, from the owner of the vehicle, as payment for the provided power. Alternatively, or in addition, if the owner of the vehicle provided power to another vehicle (or another device/system), that owner may be owed compensation for the provided power or energy, e.g., a credit.

The power management controller 1324 can be a computer or computing system(s) and/or electrical system with associated components, as described herein, capable of managing the power generation unit 1504 to receive power, routing the power to the power storage 612, and then providing the power from either the power generation unit 1504 and/or the power storage 612 to the loads 1508. Thus, the power management controller 1324 may execute programming that controls switches, devices, components, etc. involved in the reception, storage, and provision of the power in the electrical system 1500.

An embodiment of the power generation unit 1504 may be as shown in FIG. 16. Generally, the power generation unit 1504 may be electrically coupled to one or more power sources 1308. The power sources 1308 can include power sources internal and/or associated with the vehicle 100 and/or power sources external to the vehicle 100 to which the vehicle 100 electrically connects. One of the internal power sources can include an on board generator 1604. The generator 1604 may be an alternating current (AC) generator, a direct current (DC) generator or a self-excited generator. The AC generators can include induction generators, linear electric generators, and/or other types of generators. The DC generators can include homopolar generators and/or other types of generators. The generator 1604 can be brushless or include brush contacts and generate the electric field with permanent magnets or through induction. The generator 1604 may be mechanically coupled to a source of kinetic energy, such as an axle or some other power take-off. The generator 1604 may also have another mechanical coupling to an exterior source of kinetic energy, for example, a wind turbine.

Another power source 1308 may include wired or wireless charging 1608. The wireless charging system 1608 may include inductive and/or resonant frequency inductive charging systems that can include coils, frequency generators, controllers, etc. Wired charging may be any kind of grid-connected charging that has a physical connection, although, the wireless charging may be grid connected through a wireless interface. The wired charging system can include an connectors, wired interconnections, the controllers, etc. The wired and wireless charging systems 1608 can provide power to the power generation unit 1504 from external power sources 1308.

Internal sources for power may include a regenerative braking system 1612. The regenerative braking system 1612 can convert the kinetic energy of the moving car into electrical energy through a generation system mounted within the wheels, axle, and/or braking system of the vehicle 100. The regenerative braking system 1612 can include any coils, magnets, electrical interconnections, converters, controllers, etc. required to convert the kinetic energy into electrical energy.

Another source of power 1308, internal to or associated with the vehicle 100, may be a solar array 1616. The solar array 1616 may include any system or device of one or more solar cells mounted on the exterior of the vehicle 100 or integrated within the body panels of the vehicle 100 that provides or converts solar energy into electrical energy to provide to the power generation unit 1504.

The power sources 1308 may be connected to the power generation unit 1504 through an electrical interconnection 1618. The electrical interconnection 1618 can include any wire, interface, bus, etc. between the one or more power sources 1308 and the power generation unit 1504.

The power generation unit 1504 can also include a power source interface 1620. The power source interface 1620 can be any type of physical and/or electrical interface used to receive the electrical energy from the one or more power sources 1308; thus, the power source interface 1620 can include an electrical interface 1624 that receives the electrical energy and a mechanical interface 1628 which may include wires, connectors, or other types of devices or physical connections. The mechanical interface 1608 can also include a physical/electrical connection 1634 to the power generation unit 1504.

The electrical energy from the power source 1308 can be processed through the power source interface 1624 to an electric converter 1632. The electric converter 1632 may convert the characteristics of the power from one of the power sources into a useable form that may be used either by the power storage 612 or one or more loads 1508 within the vehicle 100. The electrical converter 1624 may include any electronics or electrical devices and/or component that can change electrical characteristics, e.g., AC frequency, amplitude, phase, etc. associated with the electrical energy provided by the power source 1308. The converted electrical energy may then be provided to an optional conditioner 1638. The conditioner 1638 may include any electronics or electrical devices and/or component that may further condition the converted electrical energy by removing harmonics, noise, etc. from the electrical energy to provide a more stable and effective form of power to the vehicle 100.

Figure 17:
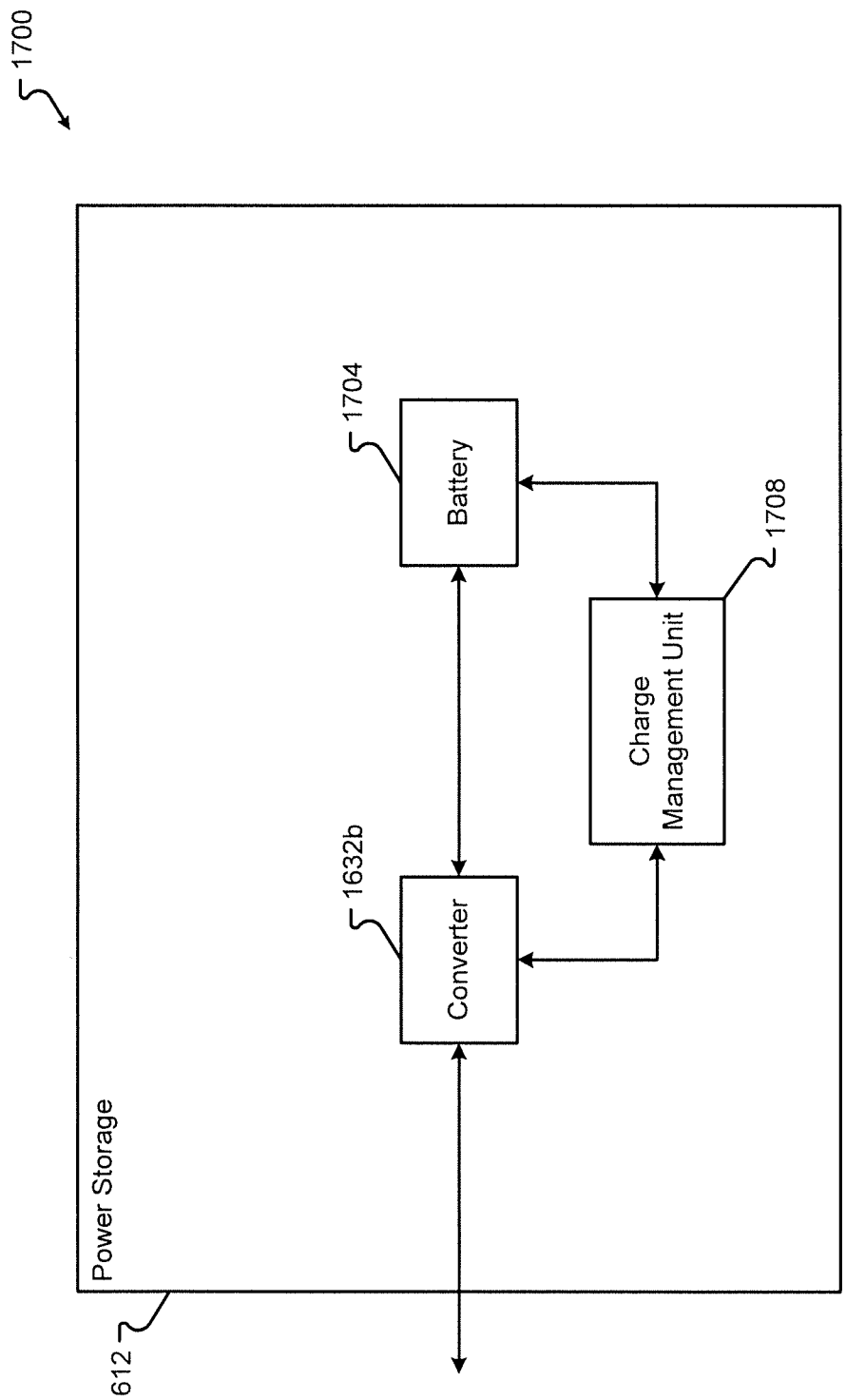
FIG. 17 is a block diagram of an embodiment of power storage associated with the electrical system of the vehicle.

An embodiment of the power storage 1612 may be as shown in FIG. 17. The power storage unit can include an electrical converter 1632b, one or more batteries, one or more rechargeable batteries, one or more capacitors, one or more accumulators, one or more supercapacitors, one or more ultrabatteries, and/or superconducting magnetics 1704, and/or a charge management unit 1708. The converter 1632b may be the same or similar to the electrical converter 1632a shown in FIG. 16. The converter 1632b may be a replacement for the electric converter 1632a shown in FIG. 16 and thus eliminate the need for the electrical converter 1632a as shown in FIG. 16. However, if the electrical converter 1632a is provided in the power generation unit 1504, the converter 1632b, as shown in the power storage unit 612, may be eliminated. The converter 1632b can also be redundant or different from the electrical converter 1632a shown in FIG. 16 and may provide a different form of energy to the battery and/or capacitors 1704. Thus, the converter 1632b can change the energy characteristics specifically for the battery/capacitor 1704.

The battery 1704 can be any type of battery for storing electrical energy, for example, a lithium ion battery, a lead acid battery, a nickel cadmium battery, etc. Further, the battery 1704 may include different types of power storage systems, such as, ionic fluids or other types of fuel cell systems. The energy storage 1704 may also include one or more high-capacity capacitors 1704. The capacitors 1704 may be used for long-term or short-term storage of electrical energy. The input into the battery or capacitor 1704 may be different from the output, and thus, the capacitor 1704 may be charged quickly but drain slowly. The functioning of the converter 1632 and battery capacitor 1704 may be monitored or managed by a charge management unit 1708.

The charge management unit 1708 can include any hardware (e.g., any electronics or electrical devices and/or components), software, or firmware operable to adjust the operations of the converter 1632 or batteries/capacitors 1704. The charge management unit 1708 can receive inputs or periodically monitor the converter 1632 and/or battery/capacitor 1704 from this information; the charge management unit 1708 may then adjust settings or inputs into the converter 1632 or battery/capacitor 1704 to control the operation of the power storage system 612.

Figure 18:
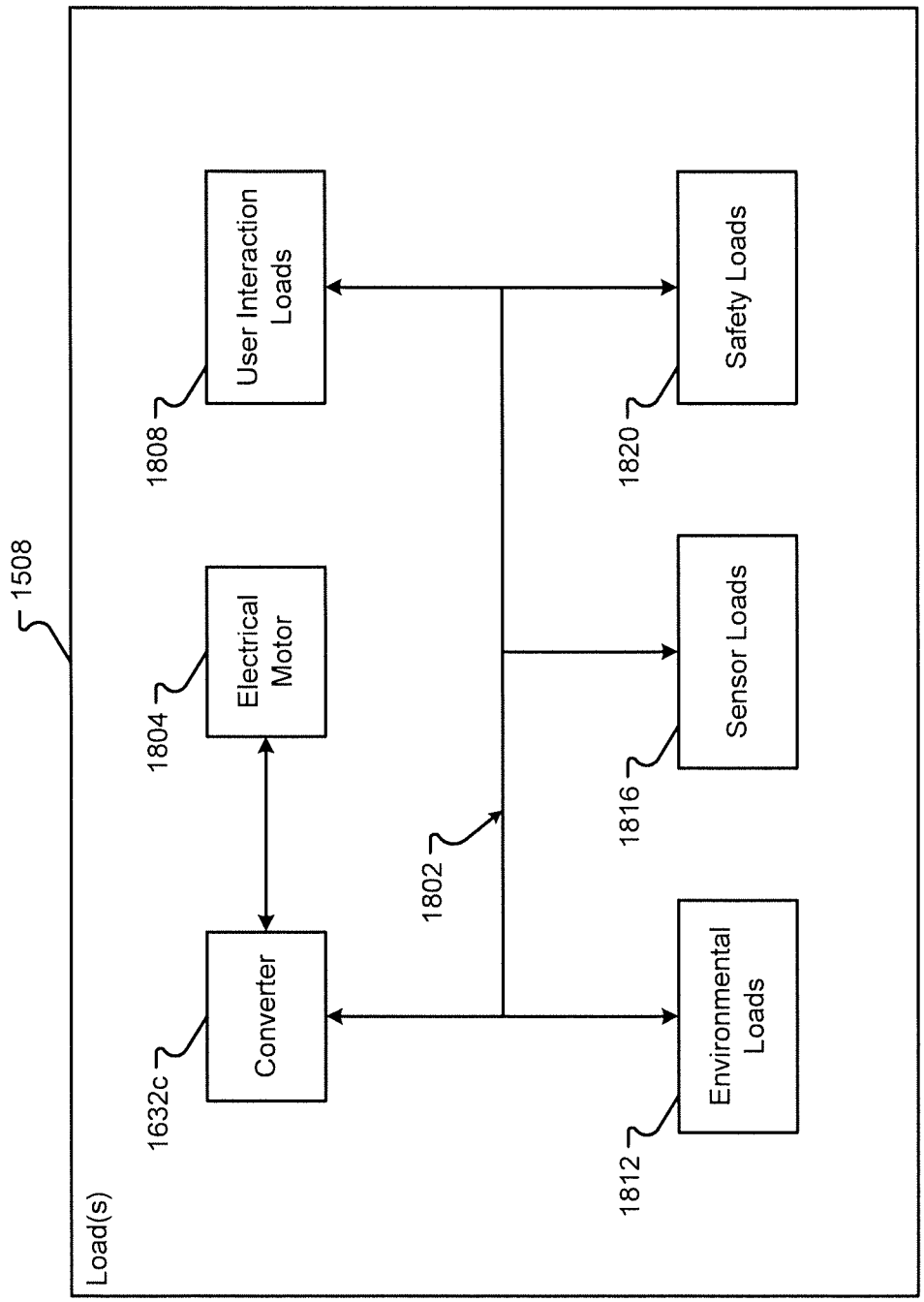
FIG. 18 is a block diagram of an embodiment of loads associated with the electrical system of the vehicle.

An embodiment of one or more loads 1508 associated with the vehicle 100 may be as shown in FIG. 18. The loads 1508 may include a bus or electrical interconnection system 1802, which provides electrical energy to one or more different loads within the vehicle 100. The bus 1802 can be any number of wires or interfaces used to connect the power generation unit 1504 and/or power storage 1612 to the one or more loads 1508. The converter 1632c may be an interface from the power generation unit 1504 or the power storage 612 into the loads 1508. The converter 1632c may be the same or similar to electric converter 1632a as shown in FIG. 16. Similar to the discussion of the converter 1632b in FIG. 17, the converter 1632c may be eliminated, if the electric converter 1632a, shown in FIG. 16, is present. However, the converter 1632c may further condition or change the energy characteristics for the bus 1802 for use by the loads 1508. The converter 1632c may also provide electrical energy to electric motor 1804, which may power the vehicle 100.

The electric motor 1804 can be any type of DC or AC electric motor. The electric motor may be a direct drive or induction motor using permanent magnets and/or winding either on the stator or rotor. The electric motor 1804 may also be wireless or include brush contacts. The electric motor 1804 may be capable of providing a torque and enough kinetic energy to move the vehicle 100 in traffic.

The different loads 1508 may also include environmental loads 1812, sensor loads 1816, safety loads 1820, user interaction loads 1808, etc. User interaction loads 1808 can be any energy used by user interfaces or systems that interact with the driver and/or passenger(s). These loads 1808 may include, for example, the heads up display, the dash display, the radio, user interfaces on the head unit, lights, radio, and/or other types of loads that provide or receive information from the occupants of the vehicle 100. The environmental loads 1812 can be any loads used to control the environment within the vehicle 100. For example, the air conditioning or heating unit of the vehicle 100 can be environmental loads 1812. Other environmental loads can include lights, fans, and/or defrosting units, etc. that may control the environment within the vehicle 100. The sensor loads 1816 can be any loads used by sensors, for example, air bag sensors, GPS, and other such sensors used to either manage or control the vehicle 100 and/or provide information or feedback to the vehicle occupants. The safety loads 1820 can include any safety equipment, for example, seat belt alarms, airbags, headlights, blinkers, etc. that may be used to manage the safety of the occupants. There may be more or fewer loads than those described herein, although they may not be shown in FIG. 18.

Figure 19A:
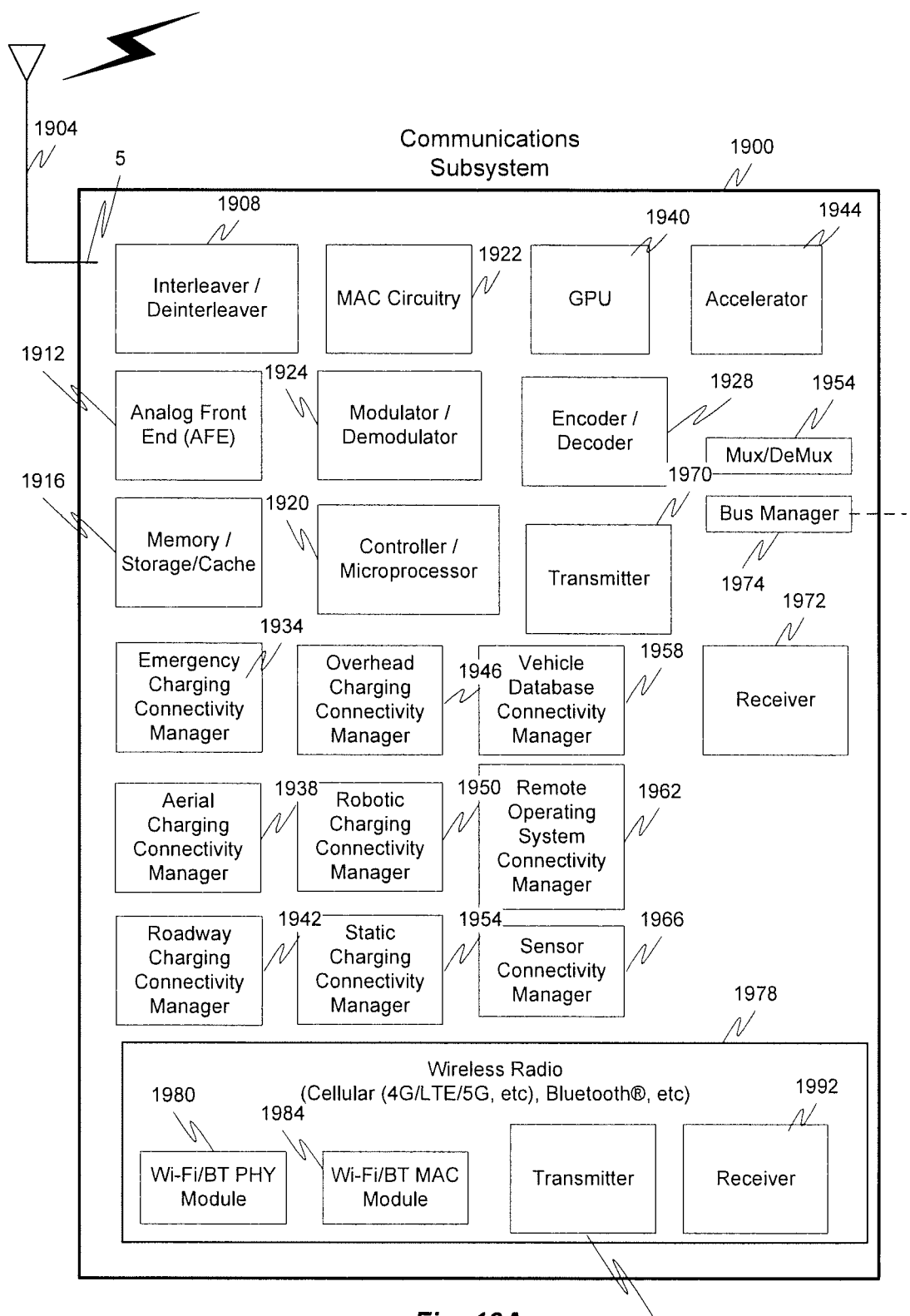
FIG. 19A is a block diagram of an exemplary embodiment of a communications subsystem of the vehicle.

FIG. 19 illustrates an exemplary hardware diagram of communications componentry that can be optionally associated with the vehicle.

The communications componentry can include one or more wired or wireless devices such as a transceiver(s) and/or modem that allows communications not only between the various systems disclosed herein but also with other devices, such as devices on a network, and/or on a distributed network such as the Internet and/or in the cloud.

The communications subsystem can also include inter- and intra-vehicle communications capabilities such as hotspot and/or access point connectivity for any one or more of the vehicle occupants and/or vehicle-to-vehicle communications.

Additionally, and while not specifically illustrated, the communications subsystem can include one or more communications links (that can be wired or wireless) and/or communications busses (managed by the bus manager 1974), including one or more of CANbus, OBD-II, ARCINC 429, Byteflight, CAN (Controller Area Network), D2B (Domestic Digital Bus), FlexRay, DC-BUS, IDB-1394, IEBus, $I^2C$, ISO 9141-1/-2, J1708, J1587, J1850, J1939, ISO 11783, Keyword Protocol 2000, LIN (Local Interconnect Network), MOST (Media Oriended Systems Transport), Multifunction Vehicle Bus, SMARTwireX, SPI, VAN (Vehicle Area Network), and the like or in general any communications protocol and/or standard.

The various protocols and communications can be communicated one or more of wirelessly and/or over transmission media such as single wire, twisted pair, fibre optic, IEEE 1394, MIL-STD-1553, MIL-STD-1773, power-line communication, or the like. (All of the above standards and protocols are incorporated herein by reference in their entirety)

As discussed, the communications subsystem enables communications between any if the inter-vehicle systems and subsystems as well as communications with non-collocated resources, such as those reachable over a network such as the Internet.

The communications subsystem, in addition to well-known componentry (which has been omitted for clarity), the device communications subsystem 1900 includes interconnected elements including one or more of: one or more antennas 1904, an interleaver/deinterleaver 1908, an analog front end (AFE) 1912, memory/storage/cache 1916, controller/microprocessor 1920, MAC circuitry 1922, modulator/demodulator 1924, encoder/decoder 1928, a plurality of connectivity managers 1934-1966, GPU 1940, accelerator 1944, a multiplexer/demultiplexer 1954, transmitter 1970, receiver 1972 and wireless radio 1978 components such as a Wi-Fi PHY/Bluetooth® module 1980, a Wi-Fi/BT MAC module 1984, transmitter 1988 and receiver 1992. The various elements in the device 1900 are connected by one or more links/busses 5 (not shown, again for sake of clarity).

The device 400 can have one more antennas 1904, for use in wireless communications such as multi-input multi-output (MIMO) communications, multi-user multi-input multi-output (MU-MIMO) communications Bluetooth®, LTE, 4G, 5G, Near-Field Communication (NFC), etc. The antenna(s) 1904 can include, but are not limited to one or more of directional antennas, omnidirectional antennas, monopoles, patch antennas, loop antennas, microstrip antennas, dipoles, and any other antenna(s) suitable for communication transmission/reception. In an exemplary embodiment, transmission/reception using MIMO may require particular antenna spacing. In another exemplary embodiment, MIMO transmission/reception can enable spatial diversity allowing for different channel characteristics at each of the antennas. In yet another embodiment, MIMO transmission/reception can be used to distribute resources to multiple users for example within the vehicle and/or in another vehicle.

Antenna(s) 1904 generally interact with the Analog Front End (AFE) 1912, which is needed to enable the correct processing of the received modulated signal and signal conditioning for a transmitted signal. The AFE 1912 can be functionally located between the antenna and a digital baseband system in order to convert the analog signal into a digital signal for processing and vice-versa.

The subsystem 1900 can also include a controller/microprocessor 1920 and a memory/storage/cache 1916. The subsystem 1900 can interact with the memory/storage/cache 1916 which may store information and operations necessary for configuring and transmitting or receiving the information described herein. The memory/storage/cache 1916 may also be used in connection with the execution of application programming or instructions by the controller/microprocessor 1920, and for temporary or long term storage of program instructions and/or data. As examples, the memory/storage/cache 1920 may comprise a computer-readable device, RAM, ROM, DRAM, SDRAM, and/or other storage device(s) and media.

The controller/microprocessor 1920 may comprise a general purpose programmable processor or controller for executing application programming or instructions related to the subsystem 1900. Furthermore, the controller/microprocessor 1920 can perform operations for configuring and transmitting/receiving information as described herein. The controller/microprocessor 1920 may include multiple processor cores, and/or implement multiple virtual processors. Optionally, the controller/microprocessor 1920 may include multiple physical processors. By way of example, the controller/microprocessor 1920 may comprise a specially configured Application Specific Integrated Circuit (ASIC) or other integrated circuit, a digital signal processor(s), a controller, a hardwired electronic or logic circuit, a programmable logic device or gate array, a special purpose computer, or the like.

The subsystem 1900 can further include a transmitter 1970 and receiver 1972 which can transmit and receive signals, respectively, to and from other devices, subsystems and/or other destinations using the one or more antennas 1904 and/or links/busses. Included in the subsystem 1900 circuitry is the medium access control or MAC Circuitry 1922. MAC circuitry 1922 provides for controlling access to the wireless medium. In an exemplary embodiment, the MAC circuitry 1922 may be arranged to contend for the wireless medium and configure frames or packets for communicating over the wireless medium.

The subsystem 1900 can also optionally contain a security module (not shown). This security module can contain information regarding but not limited to, security parameters required to connect the device to one or more other devices or other available network(s), and can include WEP or WPA/WPA-2 (optionally+AES and/or TKIP) security access keys, network keys, etc. The WEP security access key is a security password used by Wi-Fi networks. Knowledge of this code can enable a wireless device to exchange information with an access point and/or another device. The information exchange can occur through encoded messages with the WEP access code often being chosen by the network administrator. WPA is an added security standard that is also used in conjunction with network connectivity with stronger encryption than WEP.

The exemplary subsystem 1900 also includes a GPU 1940, an accelerator 1944, a Wi-Fi/BT/BLE PHY module 1980 and a Wi-Fi/BT/BLE MAC module 1984 and wireless transmitter 1988 and receiver 1992. In some embodiments, the GPU 1940 may be a graphics processing unit, or visual processing unit, comprising at least one circuit and/or chip that manipulates and changes memory to accelerate the creation of images in a frame buffer for output to at least one display device. The GPU 1940 may include one or more of a display device connection port, printed circuit board (PCB), a GPU chip, a metal-oxide-semiconductor field-effect transistor (MOSFET), memory (e.g., single data rate random-access memory (SDRAM), double data rate random-access memory (DDR) RAM, etc., and/or combinations thereof), a secondary processing chip (e.g., handling video out capabilities, processing, and/or other functions in addition to the GPU chip, etc.), a capacitor, heatsink, temperature control or cooling fan, motherboard connection, shielding, and the like.

The various connectivity managers 1934-1966 (even) manage and/or coordinate communications between the subsystem 1900 and one or more of the systems disclosed herein and one or more other devices/systems. The connectivity managers include an emergency charging connectivity manager 1934, an aerial charging connectivity manager 1938, a roadway charging connectivity manager 1942, an overhead charging connectivity manager 1946, a robotic charging connectivity manager 1950, a static charging connectivity manager 1954, a vehicle database connectivity manager 1958, a remote operating system connectivity manager 1962 and a sensor connectivity manager 1966.

The emergency charging connectivity manager 1934 can coordinate not only the physical connectivity between the vehicle and the emergency charging device/vehicle, but can also communicate with one or more of the power management controller, one or more third parties and optionally a billing system(s). As an example, the vehicle can establish communications with the emergency charging device/vehicle to one or more of coordinate interconnectivity between the two (e.g., by spatially aligning the charging receptacle on the vehicle with the charger on the emergency charging vehicle) and optionally share navigation information. Once charging is complete, the amount of charge provided can be tracked and optionally forwarded to, for example, a third party for billing. In addition to being able to manage connectivity for the exchange of power, the emergency charging connectivity manager 1934 can also communicate information, such as billing information to the emergency charging vehicle and/or a third party. This billing information could be, for example, the owner of the vehicle, the driver of the vehicle, company information, or in general any information usable to charge the appropriate entity for the power received.

The aerial charging connectivity manager 1938 can coordinate not only the physical connectivity between the vehicle and the aerial charging device/vehicle, but can also communicate with one or more of the power management controller, one or more third parties and optionally a billing system(s). As an example, the vehicle can establish communications with the aerial charging device/vehicle to one or more of coordinate interconnectivity between the two (e.g., by spatially aligning the charging receptacle on the vehicle with the charger on the emergency charging vehicle) and optionally share navigation information. Once charging is complete, the amount of charge provided can be tracked and optionally forwarded to, for example, a third party for billing. In addition to being able to manage connectivity for the exchange of power, the aerial charging connectivity manager 1938 can similarly communicate information, such as billing information to the aerial charging vehicle and/or a third party. This billing information could be, for example, the owner of the vehicle, the driver of the vehicle, company information, or in general any information usable to charge the appropriate entity for the power received etc., as discussed.

The roadway charging connectivity manager 1942 and overhead charging connectivity manager 1946 can coordinate not only the physical connectivity between the vehicle and the charging device/system, but can also communicate with one or more of the power management controller, one or more third parties and optionally a billing system(s). As one example, the vehicle can request a charge from the charging system when, for example, the vehicle needs or is predicted to need power. As an example, the vehicle can establish communications with the charging device/vehicle to one or more of coordinate interconnectivity between the two for charging and share information for billing. Once charging is complete, the amount of charge provided can be tracked and optionally forwarded to, for example, a third party for billing. This billing information could be, for example, the owner of the vehicle, the driver of the vehicle, company information, or in general any information usable to charge the appropriate entity for the power received etc., as discussed. The person responsible for paying for the charge could also receive a copy of the billing information as is customary. The robotic charging connectivity manager 1950 and static charging connectivity manager 1954 can operate in a similar manner to that described herein.

The vehicle database connectivity manager 1958 allows the subsystem to receive and/or share information stored in the vehicle database. This information can be shared with other vehicle components/subsystems and/or other entities, such as third parties and/or charging systems. The information can also be shared with one or more vehicle occupant devices, such as an app on a mobile device the driver uses to track information about the vehicle and/or a dealer or service/maintenance provider. In general any information stored in the vehicle database can optionally be shared with any one or more other devices optionally subject to any privacy or confidentially restrictions.

The remote operating system connectivity manager 1962 facilitates communications between the vehicle and any one or more autonomous vehicle systems. These communications can include one or more of navigation information, vehicle information, occupant information, or in general any information related to the remote operation of the vehicle.

The sensor connectivity manager 1966 facilitates communications between any one or more of the vehicle sensors and any one or more of the other vehicle systems. The sensor connectivity manager 1966 can also facilitate communications between any one or more of the sensors and/or vehicle systems and any other destination, such as a service company, app, or in general to any destination where sensor data is needed.

In accordance with one exemplary embodiment, any of the communications discussed herein can be communicated via the conductor(s) used for charging. One exemplary protocol usable for these communications is Power-line communication (PLC). PLC is a communication protocol that uses electrical wiring to simultaneously carry both data, and Alternating Current (AC) electric power transmission or electric power distribution. It is also known as power-line carrier, power-line digital subscriber line (PDSL), mains communication, power-line telecommunications, or power-line networking (PLN). For DC environments in vehicles PLC can be used in conjunction with CAN-bus, LIN-bus over power line (DC-LIN) and DC-BUS.

The communications subsystem can also optionally manage one or more identifiers, such as an IP (internet protocol) address(es), associated with the vehicle and one or other system or subsystems or components therein. These identifiers can be used in conjunction with any one or more of the connectivity managers as discussed herein.

Figure 19B:
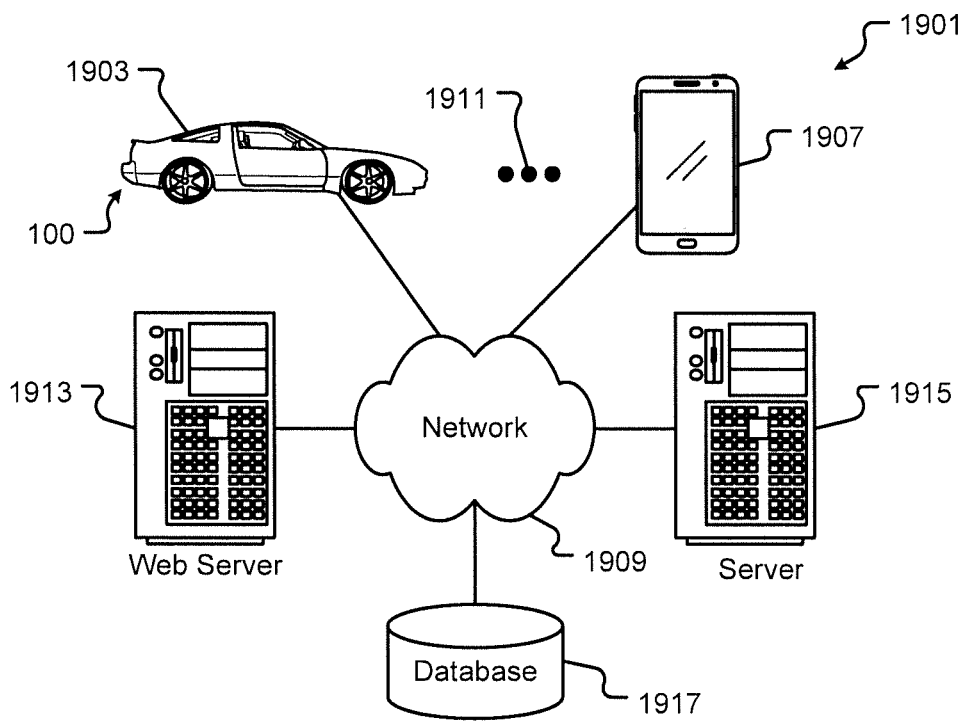
FIG. 19B is a block diagram of a computing environment associated with the embodiments presented herein.

FIG. 19B illustrates a block diagram of a computing environment 1901 that may function as the servers, user computers, or other systems provided and described above. The environment 1901 includes one or more user computers, or computing devices, such as a vehicle computing device 1903, a communication device 1907, and/or more 1911. The computing devices 1903, 1907, 1911 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 1903, 1907, 1911 may also have any of a variety of applications, including for example, database client and/or server applications, and web browser applications. Alternatively, the computing devices 1903, 1907, 1911 may be any other electronic device, such as a thin-client computer, Internet-enabled mobile telephone, and/or personal digital assistant, capable of communicating via a network 1909 and/or displaying and navigating web pages or other types of electronic documents. Although the exemplary computer environment 1901 is shown with two computing devices, any number of user computers or computing devices may be supported.

Environment 1901 further includes a network 1909. The network 1909 may can be any type of network familiar to those skilled in the art that can support data communications using any of a variety of commercially-available protocols, including without limitation SIP, TCP/IP, SNA, IPX, AppleTalk, and the like. Merely by way of example, the network 1909 maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.9 suite of protocols, the Bluetooth® protocol known in the art, and/or any other wireless protocol); and/or any combination of these and/or other networks.

The system may also include one or more servers 1913, 1915. In this example, server 1913 is shown as a web server and server 1915 is shown as an application server. The web server 1913, which may be used to process requests for web pages or other electronic documents from computing devices 1903, 1907, 1911. The web server 1913 can be running an operating system including any of those discussed above, as well as any commercially-available server operating systems. The web server 1913 can also run a variety of server applications, including SIP servers, HTTP servers, FTP servers, CGI servers, database servers, Java servers, and the like. In some instances, the web server 1913 may publish operations available operations as one or more web services.

The environment 1901 may also include one or more file and or/application servers 1915, which can, in addition to an operating system, include one or more applications accessible by a client running on one or more of the computing devices 1903, 1907, 1911. The server(s) 1915 and/or 1913 may be one or more general purpose computers capable of executing programs or scripts in response to the computing devices 1903, 1907, 1911. As one example, the server 1915, 1913 may execute one or more web applications. The web application may be implemented as one or more scripts or programs written in any programming language, such as Java™, C, C#®, or C++, and/or any scripting language, such as Perl, Python, or TCL, as well as combinations of any programming/scripting languages. The application server(s) 1915 may also include database servers, including without limitation those commercially available from Oracle, Microsoft, Sybase™, IBM™ and the like, which can process requests from database clients running on a computing device 1903, 1907, 1911.

The web pages created by the server 1913 and/or 1915 may be forwarded to a computing device 1903, 1907, 1911 via a web (file) server 1913, 1915. Similarly, the web server 1913 may be able to receive web page requests, web services invocations, and/or input data from a computing device 1903, 1907, 1911 (e.g., a user computer, etc.) and can forward the web page requests and/or input data to the web (application) server 1915. In further embodiments, the server 1915 may function as a file server. Although for ease of description, FIG. 19B illustrates a separate web server 1913 and file/application server 1915, those skilled in the art will recognize that the functions described with respect to servers 1913, 1915 may be performed by a single server and/or a plurality of specialized servers, depending on implementation-specific needs and parameters. The computer systems 1903, 1907, 1911, web (file) server 1913 and/or web (application) server 1915 may function as the system, devices, or components described in FIGS. 1-19A.

The environment 1901 may also include a database 1917. The database 1917 may reside in a variety of locations. By way of example, database 1917 may reside on a storage medium local to (and/or resident in) one or more of the computers 1903, 1907, 1911, 1913, 1915. Alternatively, it may be remote from any or all of the computers 1903, 1907, 1911, 1913, 1915, and in communication (e.g., via the network 1909) with one or more of these. The database 1917 may reside in a storage-area network ("SAN") familiar to those skilled in the art. Similarly, any necessary files for performing the functions attributed to the computers 1903, 1907, 1911, 1913, 1915 may be stored locally on the respective computer and/or remotely, as appropriate. The database 1917 may be a relational database, such as Oracle 20i®, that is adapted to store, update, and retrieve data in response to SQL-formatted commands.

Figure 19C:
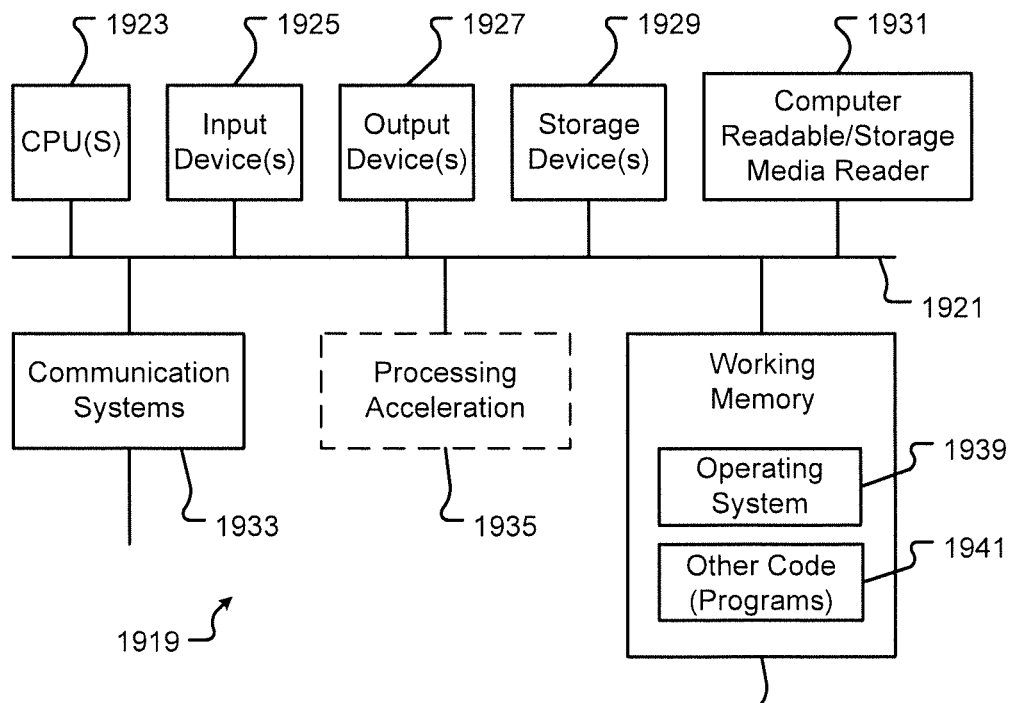
FIG. 19C is a block diagram of a computing device associated with one or more components described herein.

FIG. 19C illustrates one embodiment of a computer system 1919 upon which the servers, user computers, computing devices, or other systems or components described above may be deployed or executed. The computer system 1919 is shown comprising hardware elements that may be electrically coupled via a bus 1921. The hardware elements may include one or more central processing units (CPUs) 1923; one or more input devices 1925 (e.g., a mouse, a keyboard, etc.); and one or more output devices 1927 (e.g., a display device, a printer, etc.). The computer system 1919 may also include one or more storage devices 1929. By way of example, storage device(s) 1929 may be disk drives, optical storage devices, solid-state storage devices such as a random access memory ("RAM") and/or a read-only memory ("ROM"), which can be programmable, flash-updateable and/or the like.

The computer system 1919 may additionally include a computer-readable storage media reader 1931; a communications system 1933 (e.g., a modem, a network card (wireless or wired), an infra-red communication device, etc.); and working memory 1937, which may include RAM and ROM devices as described above. The computer system 1919 may also include a processing acceleration unit 1935, which can include a DSP, a special-purpose processor, and/or the like.

The computer-readable storage media reader 1931 can further be connected to a computer-readable storage medium, together (and, optionally, in combination with storage device(s) 1929) comprehensively representing remote, local, fixed, and/or removable storage devices plus storage media for temporarily and/or more permanently containing computer-readable information. The communications system 1933 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 1919 may also comprise software elements, shown as being currently located within a working memory 1937, including an operating system 1939 and/or other code 1941. It should be appreciated that alternate embodiments of a computer system 1919 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 1923 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

As REVs rise in popularity, violation of battery pack licensing and warranty restrictions on battery pack use will become an increasingly large problem. REV owners may secretly use battery packs in violation of licensing and warranty requirements and restrictions, thereby increasing warranty coverage costs of vehicle manufacturers. For example, REV owners or third party service facilities may substitute less expensive unauthorized cells, modules, or batteries for authorized cells, modules, or batteries in the pack. For illegal battery pack alterations or substitutions by third party service facilities, not only manufacturers but also owners/operators of vehicles should be notified.

This disclosure discloses systems and methods for exchanging identifier information and power source-related measurements between a vehicle and a reporting entity about an on board power source (e.g., cell, module, battery, or battery pack). The identifier can be associated with the on board power source. It can be read periodically and compared to stored values. When the read value differs from a stored value for an identifier and/or associated power source-related measurement, it is indication that a licensing and/or warranty requirement or restriction has been violated. Examples of licensing requirements or restrictions include limitations on geographical use of the battery pack, requirements of payment of a one-time or ongoing fee for battery pack use, use of the battery pack in a different vehicle, and the like. Examples of warranty requirements or restrictions include requirements on battery pack discharging and/or charging to avoid damage to the battery pack, tampering with or altering the battery pack in a manner that violates the warranty, substitution of unauthorized parts in the battery pack, and the like. These rule violations can be identified not only by use of different battery pack or battery pack component identifiers but also by detection of alterations in battery pack or battery pack component performance or other operational parameters. For example, replacing a battery in the pack with a different (older or newer) battery can be detected by an unacceptable increase or decrease in a battery pack performance or other operational parameter even if the same identifier or tag is reused on the different battery.

The identifier can be any unique or quasi-unique sequence of characters, such as numbers, letters, or symbols. It can be physically attached by a label to the power source or component thereof, printed or painted on the power source or component thereof, or digitally stored in a computational tag, such as RFID, that is physically attached to the power source or component thereof.

The identifier can be paired with a sensor responsible for collecting parameters for the battery pack or common battery pack component with which the identifier is associated. This can be done by including the identifier in the signaling payload from the sensor or including the sensor electronic address or other sensor identifier in the signaling payload received from an RFID tag comprising the identifier. Alternatively, a look up table can be used to index or map each identifier against a corresponding electronic address or other sensor identifier.

The power source-related measurement can be sensed, captured, or otherwise collected by an on board sensor and can be a static or dynamic parameter. The parameter can be, for instance, an operating metric or other parameter associated with the vehicle power source or component thereof. Examples include winding temperature and/or rotor speed of on board electric motor(s), battery pack voltage, output current, state-of-charge, state-of-health, state-of-function, or temperature, motor controller current (and/or direction of current), voltage, temperature and leaking current, accelerator pedal voltage as a function of voltage position, and other power source-related measurements.

The controller/microprocessor 1920 or sensor connectivity manager 1966 of the vehicle 120 generally continuously or substantially continuously monitors sensor feedback signals to acquire the foregoing parameters. In the case of a rechargeable electric vehicle, the foregoing measurement can be determined for the battery pack as a whole, each module thereof, each battery thereof, and/or each cell thereof.

Referring to FIG. 20, a monitoring system 2000 is depicted according to an embodiment. The monitoring system 2000 comprises a power manager (not shown) on board a vehicle 2004 in communication, via network 1909, with a manufacturer warranty server 2008 (which includes a warranty manager) and associated warranty database 2020, and/or a licensing server 2012 (which includes license manager) and associated licensing database 2016. The manufacturer warranty 2008 and associated warranty database 2020 receive power source identifier(s) and optionally power source measurements and the warranty manager determines, based on comparisons to stored identifier(s) and/or power source measurements for the vehicle, whether or not the on board vehicle power source has been substituted or altered in a manner violating warranty restrictions or requirements. The licensing server 2012 and associated licensing database 2016 receive power source identifier(s) and/or power source measurements and the license manager determines, based on comparisons to stored identifier(s) and/or power source measurements for the vehicle, whether or not the on board vehicle power source has been used in a manner violating licensing restrictions or requirements. As will be appreciated, warranty restrictions and requirements delineate when and for what defects or faults or malfunctions a warranty will apply and over what time period and practices or other events that can void warranty coverage while licensing restrictions and requirements delineate the metes and bounds of permission to use the power source.

Figure 21:
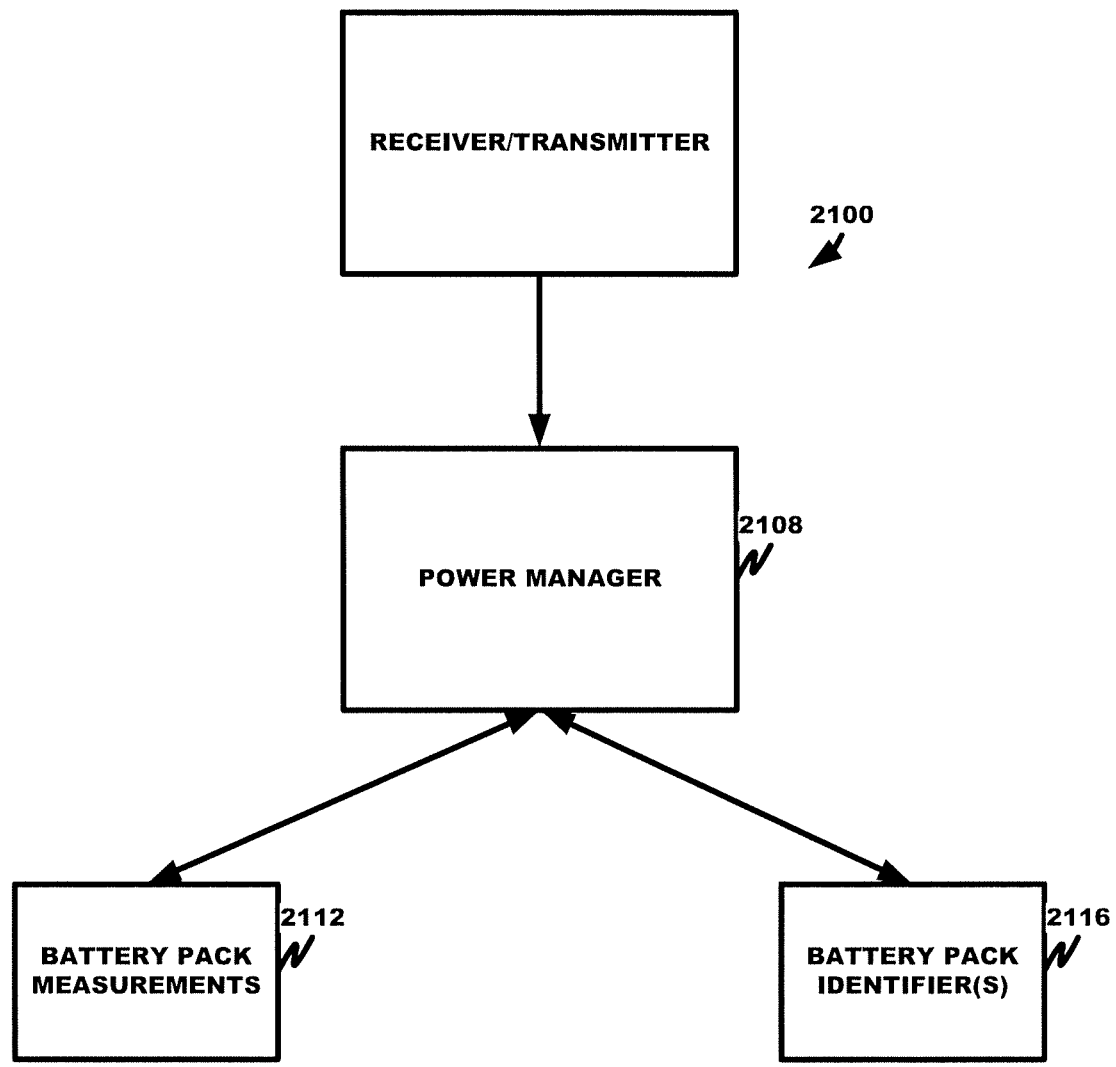
FIG. 21 is a block diagram of an on board power manager according to an embodiment.

Referring to FIG. 21, the power management system 2100 on board the vehicle 2004 comprises a receiver 1972 or 1992 and transmitter 1970 or 1988 to receive and send, respectively, wireless signals, a power manager 2108 to receive, via receiver 1972 or 1992, requests for identifier(s) and power source measurements in connection with warranty monitoring or license checks. In the case of an REV, the power manager 2108 maintains and accesses battery pack measurements 2112 and battery pack identifier(s) 2116.

The battery pack measurements 2112 can be any performance measurement associated with the battery pack, module, battery or cell, including, without limitation, stored energy level, winding temperature, voltage level, output electrical current, electrical current direction of flow, leakage current, temperature, state-of-charge, state-of-health, state-of-function, number of charge-discharge cycles, depth of discharge, cycle life, or calendar life.

In some applications, the parameter is non-uniform among battery packs, modules, batteries, or cells and can be time-varying or stored charge-varying. The parameter can change over the life of the battery pack, module, battery, or cell. As will be appreciated, battery packs, modules, batteries, and cells have a finite life is due to occurrence of the unwanted chemical or physical changes to, or the loss of, the active materials of which they are made. Performance deteriorates over time whether the battery pack, module, battery, or cell is used or not. This is known as "calendar fade". Performance also deteriorates with usage and this is known as "cycle fade". Battery Calendar Life is the elapsed time before a battery becomes unusable whether it is in active use or inactive. There are two key factors influencing calendar life, namely temperature and time. Battery Cycle Life is defined as the number of complete charge-discharge cycles a battery can perform before its nominal capacity falls below 80% of its initial rated capacity. Key factors affecting cycle life are time t and the number N of charge-discharge cycles completed.

Battery pack, module, battery, or cell identifiers comprise, for example, any unique or quasi-unique code, such as a serial or product code. The identifier can, for example, be a unique or quasi-unique serial code or product code such as a Universal Product Code ("UPC"), Quick Response ("QR") code, or Electronic Product Code ("EPC"), or other code.

The identifier can also be an identifier digitally stored in an RFID tag. The code is a string of numerical, alphabetical, and other typographical characters or symbols.

The power manager of the vehicle generally continuously or substantially continuously monitors sensor feedback signals to acquire the foregoing measurements and an associated timestamp. The timestamp enables the temporal trend of the sensed measurement or a parameter derived therefrom to be determined for use in identifying whether or not the historically sensed measurement or parameter battery pack, module, battery or cell is consistent with the currently sensed measurement or parameter for the battery pack, module, battery or cell. This can be done using known battery pack, module, battery or cell performance trends over time and use patterns.

The power manager is responsible for governing the operation of the vehicle. The power manager can receive inputs from the operator, control/feedback signals from a motor controller (not shown) and motor (not shown) and also feedback signals from other systems (not shown) within the vehicle. The speed at which the power manager must receive data from other systems, process the data in an algorithm, and output a response to the given conditions must be accomplished in milliseconds The power manager can receive the sensor feedback measurement signals noted in the prior paragraph.

Figure 22:
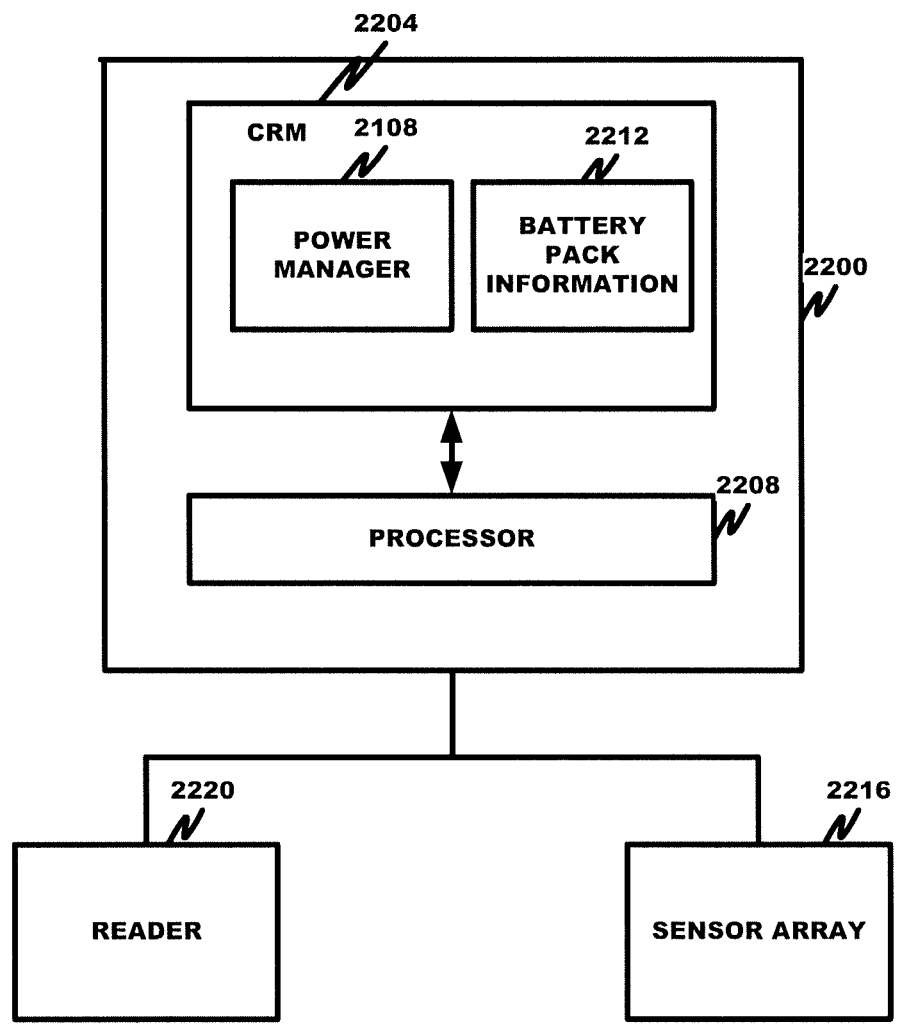
FIG. 22 is a block diagram of an on board computational device executing the power manager according to an embodiment.
Figure 23:
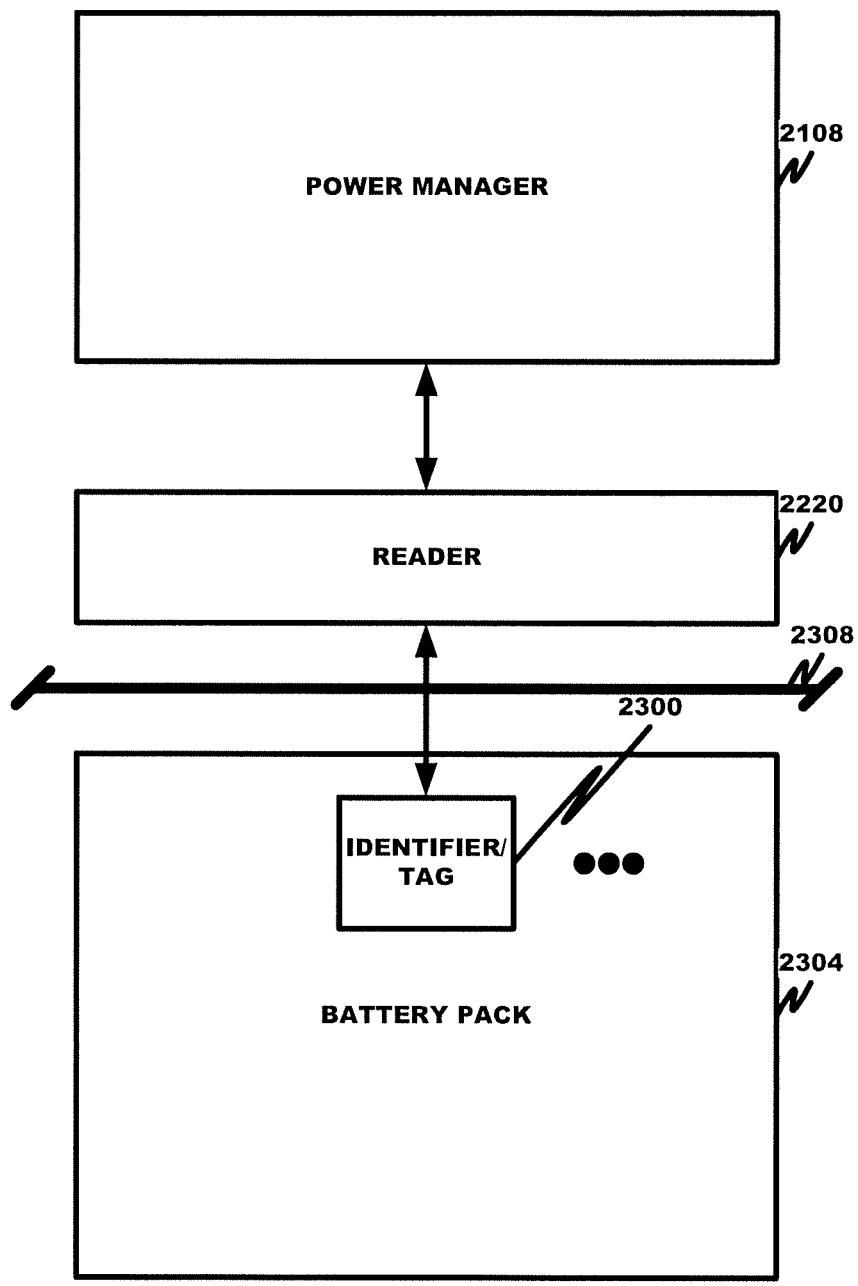
FIG. 23 is a block diagram of the on board power manager and battery pack information collection system

Referring to FIGS. 22-23, the computational system 2200 on board the vehicle executing the power manager 2108 comprises a computer readable medium 2204 comprising the power manager 2108 and battery pack information 2212 (which includes the battery pack measurements 2112 and battery pack identifiers 2116), and a processor 2208. The power manager 2108 can receive the battery pack measurements 2112 from a sensor array 2216 and the identifiers 2116 from a reader 2220. Referring to FIG. 23, the power manager 2108 reads, via the reader 2220, one or more identifier(s) 2300, from the battery pack 2304 or a component thereof.

The sensor array 2216 can include a throttle position sensor, manifold pressure sensor, engine coolant temperature sensor, mass air flow sensor, camshaft position sensor, crankshaft position sensor, pedal angle sensor, chassis position sensor, oxygen sensor, AC, or DC current sensor, brake pad wear sensor, detonation sensor, EGR sensor and intake air temperature sensor.

The reader 2220 can be any device able to read an identifier or tag 2300 on the battery pack. This can be done in many ways. For example, a passive RFID configuration can be used in which a battery-assisted passive or passive RFID chip, containing in memory the identifier 2300, is on the cell, module, battery, or battery pack and an active reader 2220 (powered by the on board battery pack) is on the vehicle, or active RFID configuration can be used in which an active RFID chip, containing in memory the identifier 2300, is on the cell, module, battery, or battery pack and powered thereby and a passive reader 2220 is on the vehicle. The RFID system can be active reader passive tag in which the active reader transmits interrogator signals and receives authentication replies from the passive tag or active reader active tag in which the active reader awakes an active tag (or battery-assisted passive tag) with an interrogator signal.

RFID tags contain at least two parts: an integrated circuit for storing and processing information, modulating and demodulating a radio-frequency (RF) signal, collecting DC power from the incident reader signal, and other specialized functions; and an antenna for receiving and transmitting the signal. The tag information is stored in a non-volatile memory. The RFID tag includes either fixed or programmable logic for processing the transmission and sensor data, respectively. Tags may either be read-only, having a factory-assigned serial number that is used as a key into a database, or may be read/write, where object-specific data can be written into the tag by the licensing server 2012 or manufacturer warranty server 2008. Field programmable tags may be write-once, read-multiple; "blank" tags may be written with an electronic product code by the user.

The reader 2220 transmits an encoded radio signal to interrogate the tag. The RFID tag 2300 receives the message and then responds with its identification and other information. This may be only a unique tag serial number, serial or product code, or other product-related information such as a stock number, lot or batch number, production date, or other specific information.

The power manager 2108 can discriminate among several tags 2300 that might be within the range of the RFID reader and read them simultaneously. For example, each battery pack component, whether a module, battery or cell, can have a different tag 2300. Often more than one tag will respond to a tag reader. Collision detection can be important to allow reading of data. Two different types of protocols are used to "singulate" a particular tag, allowing its data to be read in the midst of many similar tags. In a slotted Aloha system, the reader 2220 broadcasts an initialization command and a parameter that the tags individually use to pseudo-randomly delay their responses. When using an "adaptive binary tree" protocol, the reader 2220 sends an initialization symbol and then transmits one bit of ID data at a time; only tags 2300 with matching bits respond, and eventually only one tag matches the complete ID string. Bulk reading can interrogate multiple tags at the same time.

When written into the tag 2300 by an RFID printer, the identifier of the tag 2300 can contain a 96-bit string of data. The first eight bits can be a header which identifies the version of the protocol. The next 28 bits can identify the organization that manages the data for this tag; the organization number is commonly assigned by the EPCGlobal consortium. The next 24 bits can be an object class, identifying the kind of product; the last 36 bits can be a unique serial number for a particular tag. These last two fields are set by the organization that issued the tag. Like a URL, the total electronic product code number can be used as a key into a global database to uniquely identify a particular product.

Optical RFID (aka OPID) is an alternative to RFID that is based on optical readers 2220. Unlike most other RFID chips (which use radio frequencies of 0.125-0.1342, 0.140-0.1485, 13.56, and 868-928 MHz), optical RFID operates in the electromagnetic spectrum between the frequencies of 333 THz ($3.33 \times 10^{14}$ hertz, 900 nm) and 380 THz (788 nm) and 750 THz (400 nm). The tag information is communicated to the reader 2220 by reflecting the read request. Parts of the incoming signal are filtered by the tag in a well-defined way as it is sent back to the reader. On the reader's side, the tag data can be deduced by analyzing the pattern used for filtering. As an alternative to reflection mode, active circuits can be used, replacing awkward RFID antenna with photovoltaic components and IR-LEDs on the integrated circuits, Regarding privacy, optical RFID provides much more protection against abuse than RFID based on common electromagnetic waves. This is mainly because line-of-sight is required for malicious read out. Such an attack can easily be prevented with low cost optical RFID sight blockers.

Other configurations include an optical configuration in which an illumination source and optical sensor collectively act as the reader 2220 to read the identifier 2300 configured as a bar code on each cell, module, battery, or battery pack, a magnetic ID configuration in which a magnetic reader 2220 is used to read a magnetic strip identifier 2300 on each cell, module, battery, or battery pack, and other electronic ID configurations in which an ID signal emitter located on the cell, module, battery, or battery pack wirelessly transmits by a short range protocol, such as Bluetooth™, infrared, etc., to a receiver (or reader 2220) on the vehicle or an ID signal emitter located on the cell, module, battery, or battery pack transmits by a wired channel the identifier 2300 to a receiver (or reader 2220) on the vehicle. The power manager can optically read the identifier(s) with a barcode scanner or digital camera or digitally read the identifier(s) via OBD-II.

The battery pack 2304 can be removably positioned in the vehicle. An electrical interface 2308 engages with and disengages from the battery pack 2304 during battery pack 2304 removal. The battery pack 2304 can be any configuration, such as lead acid, advanced lead acid, GM Ovonic™ NiMH, SAFT™ NiMH, SAFT™ lithium ion, lithium polymer, Zebra¶ sodium-nickel chloride, and other battery configurations known in the art.

The power manager 2108 receives data from sensors of the sensor array 2216, when, depending on the configuration, can be positioned within the battery pack adjacent to the corresponding battery pack component associated with the identifier. Temperature, current output, battery voltage and fault detection sensor output signals are provided to the power manager 2108, which calculates how much energy is remaining in the battery pack and how much energy has been consumed from the battery pack. Monitoring the battery pack temperature and the resistance to the vehicle's ground can protect both the battery pack and the passengers from danger. The power manager 2108 can monitor the energy consumed by the vehicle while being driven, as well as temperature, individual cell voltages and total pack voltage.

An exemplary embodiment of the power manager 2108 will now be discussed with reference to FIG. 24.

In step 2400, the receiver 1972 or 1992 on the vehicle 120 receives a request, from the manufacturer warranty server 2008 or licensing server 2012, for an identifier and sensed parameter associated with the battery pack.

In step 2404, the power manager validates the request using known cryptographic or other packet authentication or verification techniques, such as public-private key cryptography.

In optional step 2408, the power manager determines, from the successfully validated request, which identifier(s) and sensed parameter(s) are to be provided to the manufacturer warranty server 2008 or licensing server 2012. The identifier(s) can be for the battery pack as a whole and/or for one or more modules, batteries, or cells thereof. The sensed parameter(s) can be one or more sensed parameter(s) associated with the battery pack as a whole and/or for one or more modules, batteries, or cells thereof and can be selected ones of multiple possible sensed parameters.

In step 2412, the power manager retrieves the determined identifier(s) from the reader and sensed parameter(s) from sensor array output.

In optional step 2416, the power manager compares the retrieved determined identifier(s) and sensed parameter(s) with locally stored identifier(s) and sensed parameter(s) to determine whether or not they match and whether or not the locally stored identifier(s) and sensed parameter(s) need to be updated. In some applications, when the locally stored identifier(s) or sensed parameter(s) do not match, the power manager determines that the battery pack or component thereof is not licensed properly and sends a notice to the vehicle operator and licensing server 2012 or that the battery pack or component thereof has been altered or otherwise tampered with and sends a notice to the vehicle operator and manufacturer warranty server 2008. In other applications, the locally stored identifier(s) or sensed parameter(s) are updated when a failed match is detected.

Figure 26:
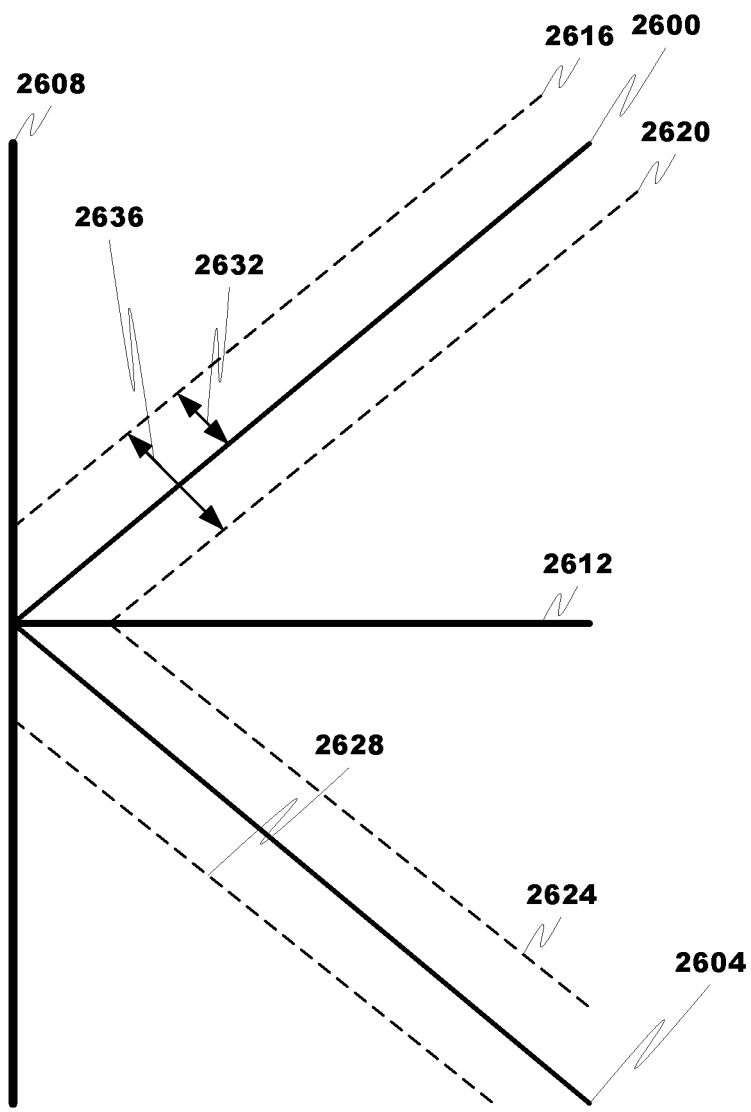
FIG. 26 is an exemplary X-Y plot of the magnitude of the first and second sensed parameters (Y-axis) as a function of a selected variable (X-axis)

While the match condition for an identifier is relatively straightforward, determining whether a match condition exists for a sensed parameter can be more difficult and depend on the type of sensed parameter. With reference to FIG. 26, two plots are illustrated, a first line 2600 for a first sensed parameter and a second line 2604 for a second sensed parameter. The X-axis 2608 can be any variable, with time being typical, and the Y-axis 2612 can be any variable, with magnitude of the first or second sensed parameter being typical. The first sensed parameter 2600 increases in magnitude over the life of the battery pack or component thereof, with examples being leakage current and number of charge-discharge cycles, while the second sensed parameter 2604 decreases in magnitude over the life of the battery pack or component thereof, with examples being (maximum) stored or storable energy level, voltage level, output electrical current, state-of-charge, state-of-health, state-of-function, remaining cycle life, or remaining calendar life. While the plot depicts the lines 2600 and 2612 originating at an origin, it is to be appreciated that they can originate at any point along the Y-axis 2608 and can have any slope or shape (other than linear). A linear relationship is used only for purposes of illustration. When the stored parameter magnitude is compared with the currently sensed parameter magnitude, a perfect match is not always possible or practical due to variations in operating parameters. To account for this variation, a match is deemed to exist when the currently sensed parameter magnitude falls within a standard deviation or range of the stored parameter magnitude (which is analogous to a point along the first or second lines 2600 or 2604). The standard deviation or range is denoted by the dashed lines 2616 and 2620 for the first line 2600 and by the dashed lines 2624 and 2628 for the second line 2604. The width of the standard deviation for the first line 2600 is shown by distance 2632 and the total width of the standard deviation on either side of the first line 2600 is shown by distance 2636. A match is therefore deemed to exist with respect to a stored first parameter lying along the first line 2600 when the magnitude of the currently sensed first parameter is within the range 2636 of the magnitude of the stored first parameter.

In step 2420, the determined identifier(s) and sensed parameter(s) are forwarded by transmitter 1970 or 1988 to the manufacturer warranty server 2008 or licensing server 2012 with an optional indication whether or not a match with locally stored identifier(s) or sensed parameter(s) exists.

An exemplary embodiment of the manufacturer warranty server 2008 or licensing server 2012 will now be discussed with reference to FIG. 25.

In step 2500, the manufacturer warranty server 2008 or licensing server 2012 receives the identifier(s) and sensed parameter(s) from the power manager.

In step 2504, the manufacturer warranty server 2008 or licensing server 2012 determines whether or not the received identifier(s) and sensed parameter(s) match previously stored values. Whether or not the received parameter matches a stored parameter is determined as noted above.

In step 2508, the manufacturer warranty server 2008 or licensing server 2012 determines that the identifier(s) and sensed parameter(s) match and updates the timestamp to a current timestamp and saves the received sensed parameter(s) as the current sensed parameter value.

In step 2512, the manufacturer warranty server 2008 or licensing server 2012 determines that one or more of the identifier(s) and sensed parameter(s) do not match and determines whether the new identifier(s) are authorized by a query to the warranty database 2020 or licensing database 2016 as appropriate.

In step 2516, the manufacturer warranty server 2008 or licensing server 2012 determines whether to update the stored identifier(s) and sensed parameter(s) to the non-matching identifier or sensed parameter value(s) and transmits an appropriate response to the power manager for presentation to the vehicle owner or operator.

Figure 24:
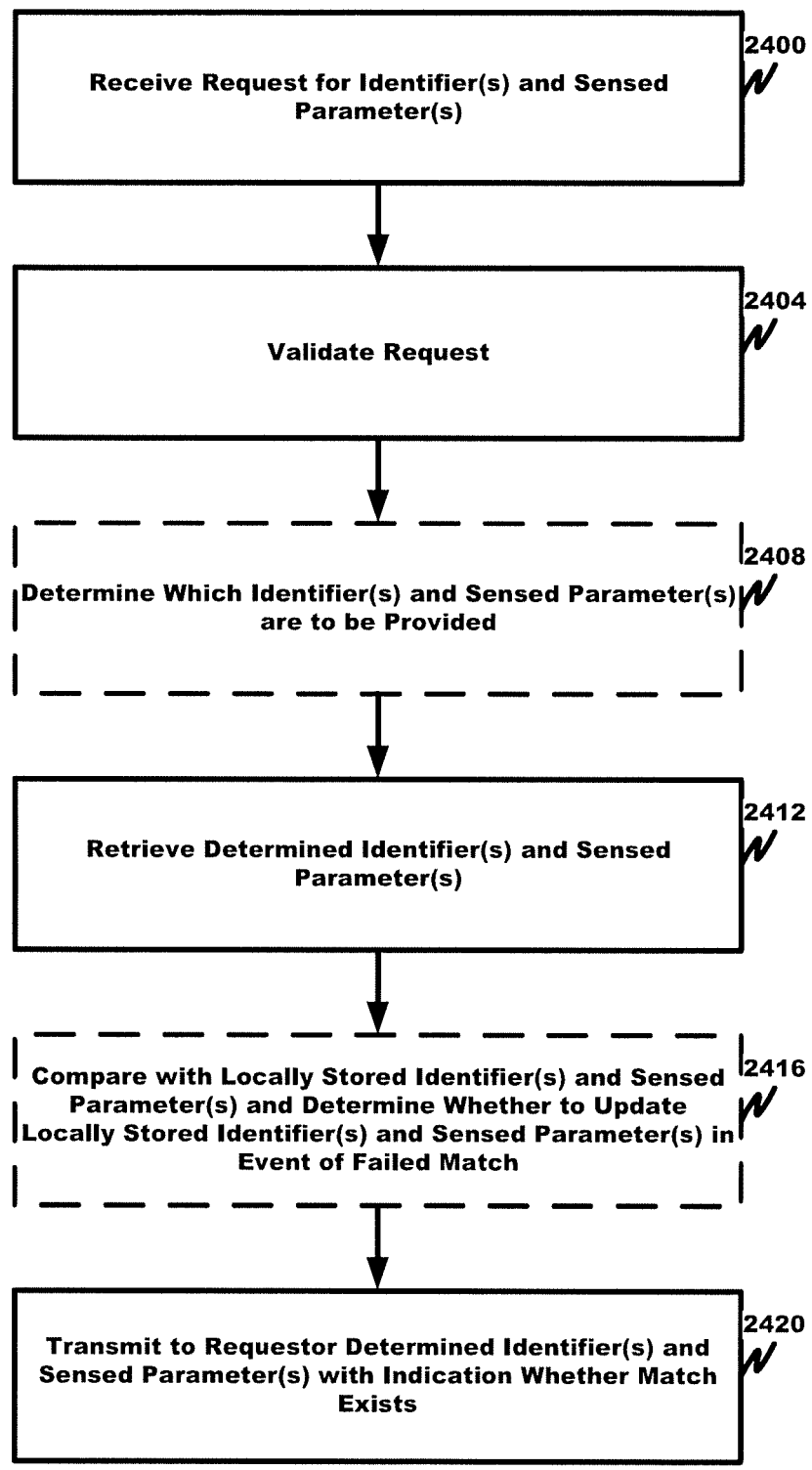
FIG. 24 is a flow chart according to an embodiment.
Figure 25:
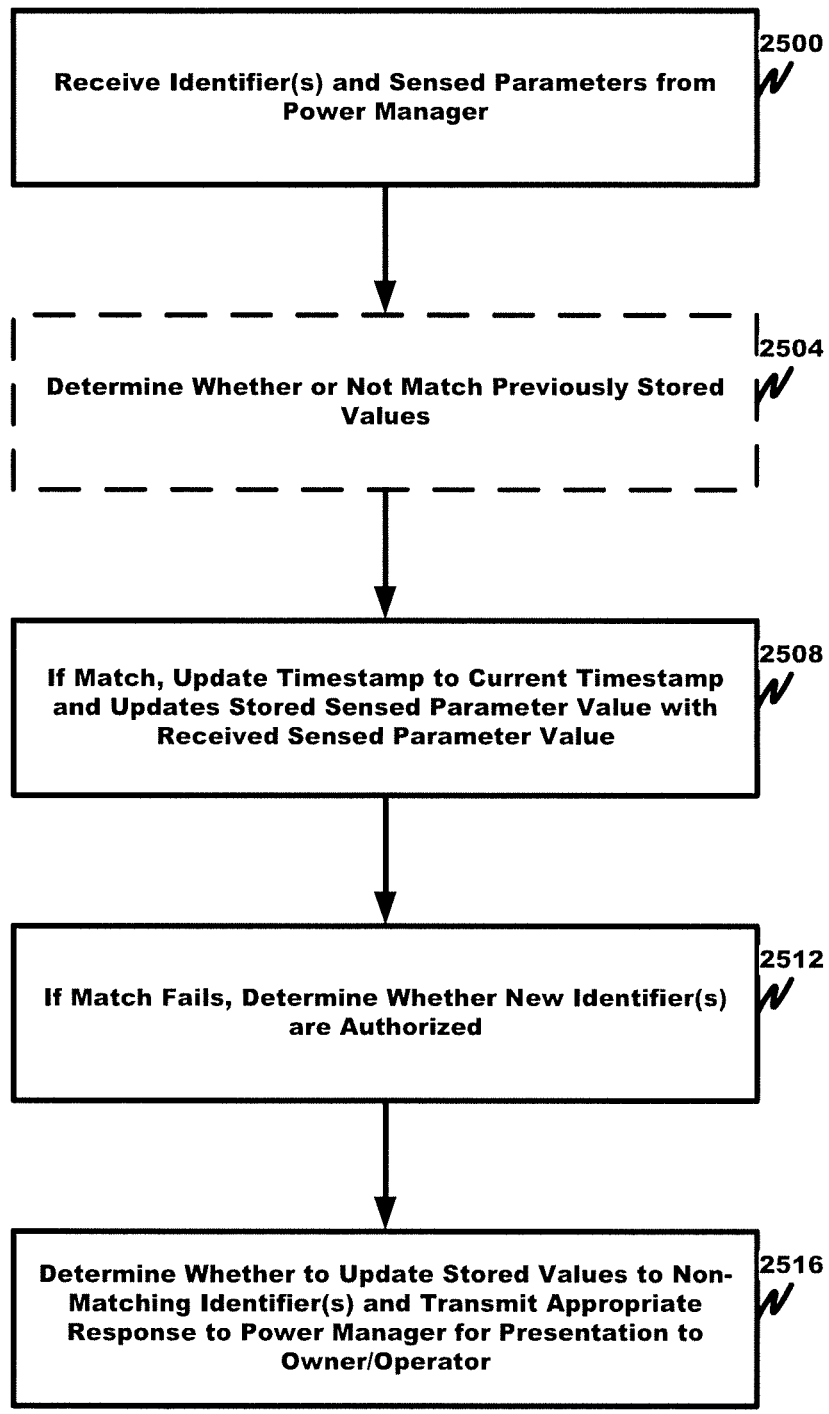
FIG. 25 is a flow chart according to an embodiment.
Figure 27:
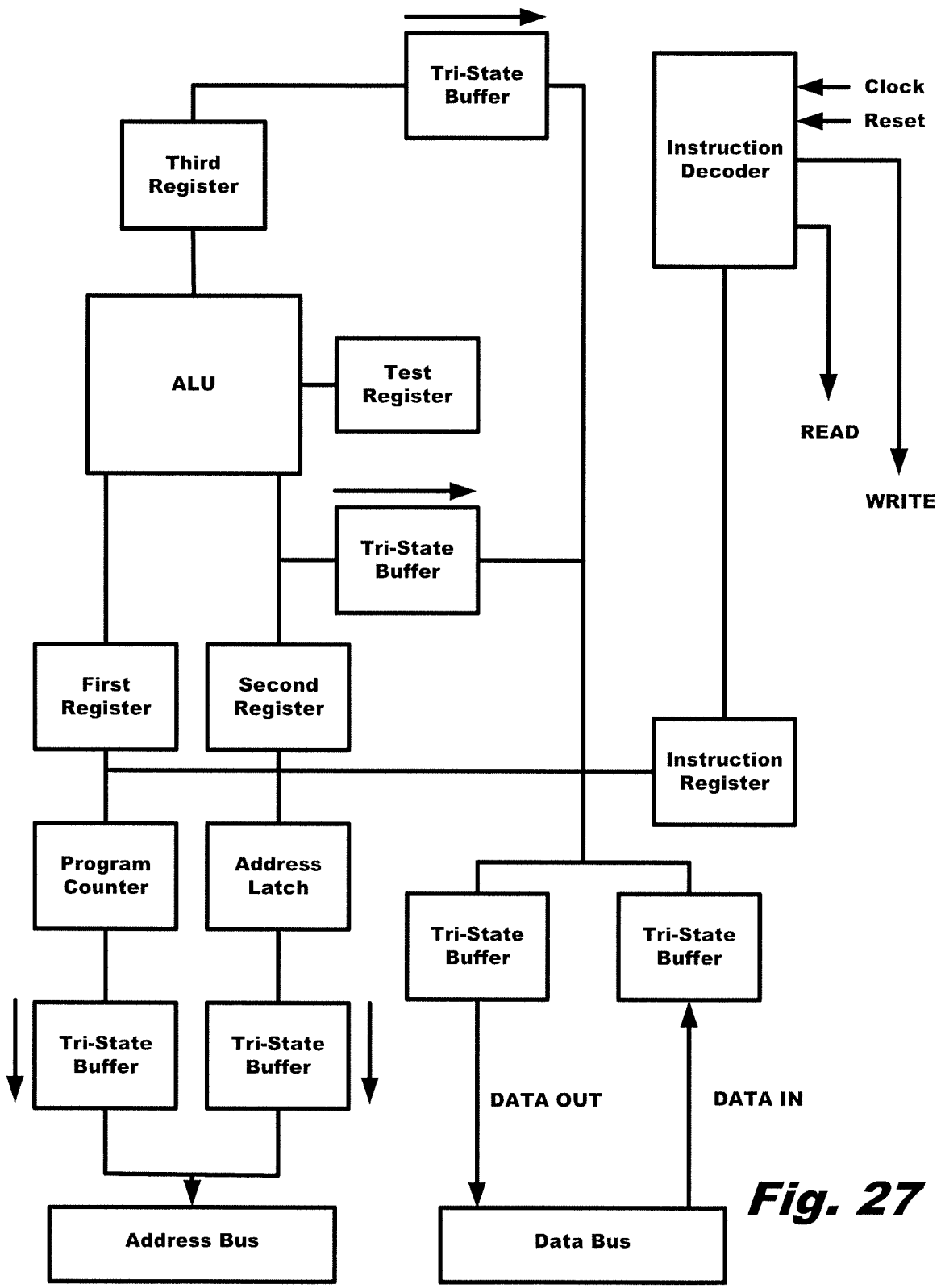
FIG. 27 is a block diagram of an exemplary computing system to execute the power monitoring system logic and the logic of its components.

With reference to FIG. 27, the logical instructions of FIGS. 24 and 25 are executed by an arithmetic/logic unit ("ALU"), which performs mathematical operations, such as addition, subtraction, multiplication, and division, machine instructions, an address bus (that sends an address to memory), a data bus (that can send data to memory or receive data from memory), a read and write line to tell the memory whether to set or get the addressed location, a clock line that enables a clock pulse to sequence the processor, and a reset line that resets the program counter to zero or another value and restarts execution. The arithmetic/logic unit can be a floating point processor that performs operations on floating point numbers. The verification system further includes first, second, and third registers that are typically configured from flip-flops, an address latch, a program counter (which can increment by "1" and reset to "0"), a test register to hold values from comparisons performed in the arithmetic/logic unit, plural tri-state buffers to pass a "1" or "0" or disconnect its output (thereby allowing multiple outputs to connect to a wire but only one of them to actually drive a "1" or "0" into the line), and an instruction register and decoder to control other components. Control lines, in the computational system 2200, manufacturer warranty server, or licensing server, from the instruction decoder can: command the first register to latch the value currently on the data bus, command the second register to latch the value currently on the data bus, command the third register to latch the value currently output by the ALU, command the program counter register to latch the value currently on the data bus, command the address register to latch the value currently on the data bus, command the instruction register to latch the value currently on the data bus, command the program counter to increment, command the program counter to reset to zero, activate any of the plural tri-state buffers (plural separate lines), command the ALU what operation to perform, command the test register to latch the ALU's test bits, activate the read line, and activate the write line. Bits from the test register and clock line as well as the bits from the instruction register come into the instruction decoder. Hardware similar or identical to that of FIG. 27 is in each of the computational system 2200 on board the vehicle, manufacturer warranty server 2008, and licensing server 2012. The ALU executes instructions for a random or pseudo-random number generation algorithm and generates the recipient identifier using the appropriate seed values.

Any of the steps, functions, and operations discussed herein can be performed continuously and automatically.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include a vehicle that can include:
a power source to propel the vehicle, the power source having one or more identifiers associated therewith;
a user interface to receive commands from an occupant and provide output to the occupant;
a plurality of on board sensors to sense one or more parameters associated with the power source or a component thereof;
a reader to determine the one or more identifiers;
a computer readable medium for storing the one or more sensed power source parameters; and
an on board microprocessor, coupled with the computer readable medium, that is programmed to:
provide the read one or more identifiers and one or more sensed power source parameters to a remote server to compare with one or more stored identifiers and one or more stored power source parameters, respectively, and apply the following rules:
when the read one or more identifiers or the one or more sensed power source parameters fails to match one or more stored identifiers or the one or more stored power source parameters, respectively, determine that a rule is violated; and
when each of the read one or more identifiers or the one or more sensed power source parameters match a corresponding one of the one or more stored identifiers or one or more stored parameters, respectively, determine that a rule is not violated.

Embodiments include a vehicle that can include:
a power source to propel the vehicle, the power source having one or more identifiers associated therewith;
a user interface to receive commands from an occupant and provide output to the occupant;
a plurality of on board sensors to sense one or more parameters associated with the power source or a component thereof;
a reader to determine the one or more identifiers;
a computer readable medium for storing one or more power source parameters; and
an on board microprocessor, coupled with the computer readable medium, that is programmed to:
compare with one or more stored identifiers and the one or more stored power source parameters, respectively, and apply the following rules:
when the read one or more identifiers or the one or more sensed power source parameters fails to match the one or more stored identifiers or the one or more stored power source parameters, respectively, determine that a rule is violated; and
when each of the read one or more identifiers or the one or more sensed power source parameters match a corresponding one of the one or more stored identifiers or the one or more stored power source parameters, respectively, determine that a rule is not violated.

Embodiments include a server that can include:

a computer readable medium for storing one or more identifiers and one or more power source parameters corresponding to plural vehicles, each vehicle comprising a power source to propel the vehicle, the power source having one or more identifiers associated therewith, a plurality of on board sensors to sense one or more parameters associated with the power source or a component thereof, and a reader to determine the one or more identifiers; and a microprocessor, coupled with the computer readable medium, that is programmed to:

receive, from each vehicle, the respective one or more identifiers and the respective sensed power source parameter to compare with the one or more stored identifiers and the one or more stored power source parameters, respectively, and apply the following rules for each vehicle:

when the read one or more identifiers or the one or more sensed power source parameters fails to match one or more stored identifiers or the one or more stored power source parameters, respectively, determine that a rule is violated; and when each of the read one or more identifiers or the one or more sensed power source parameters match a corresponding one of the one or more stored identifiers or one or more stored parameters, respectively, determine that a rule is not violated.

In aspects of one or more of the above embodiments, the rule can be a warranty or licensing rule. The power source can be a battery pack. The read one or more identifiers and one or more stored identifiers can be a serial code, Universal Product Code ("UPC"), Quick Response ("QR") code, Electronic Product Code ("EPC"), or RFID tag. The one or more sensed power source parameters and the one or more stored power source parameters can correspond to one or more of stored energy level, winding temperature, voltage level, output electrical current, electrical current direction of flow, leakage current, temperature, state-of-charge, state-of-health, state-of-function, number of charge-discharge cycles, depth of discharge, cycle life, and calendar life.

In aspects of one or more of the above embodiments, the one or more sensed power source parameters and the one or more stored power source parameters can correspond to one or more of stored energy level, voltage level, output electrical current, leakage current, state-of-charge, state-of-health, state-of-function, number of charge-discharge cycles, cycle life, and calendar life. The read one or more identifiers and the one or more stored identifiers and the one or more sensed power source parameters and the one or more stored parameters can be associated with a module, battery, or cell. The read one or more identifiers and the one or more stored identifiers can each be multiple identifiers. The sensed one or more power source parameters and the one or more stored power source parameters can each be multiple power source parameters.

In aspects of one or more of the above embodiments, the one or more sensed power source parameters can be determined to match the one or more stored power source parameters, when a magnitude of each of the one or more sensed power source parameters is within a determined range of a magnitude of a corresponding one of the one or more stored power source parameters. The one or more sensed power source parameters can be determined not to match the one or more stored power source parameters, when the magnitude one or more of the one or more of the sensed power source parameters is not within a determined range of the magnitude of any of the one or more stored power source parameters.

In aspects of one or more of the above embodiments, the reader can be one or more of an active RFID tag reader, optical reader, illumination source and optical sensor, and magnetic reader.

In aspects of one or more of the above embodiments, the identifier can be an RFID. More than one RFID tags can respond at a selected time to the reader. To disambiguate between concurrent responses from different RFID tags, the reader can broadcast (a) an initialization command and a parameter that each of the tags individually use to pseudo-randomly delay a respective response or (h) send an initialization symbol and then transmits one or more bits of identification data at a time, with only an UM tag having a matching bit responding to the transmitted one or more bits of identification data.

In aspects of one or more of the above embodiments, the one or more stored power source parameters and the one or more sensed power source parameters can each be non-uniform among power sources of plural vehicles and/or can be time-varying and/or stored charge-varying.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

The term "electric vehicle" (EV), also referred to herein as an electric drive vehicle, may use one or more electric motors or traction motors for propulsion. An electric vehicle may be powered through a collector system by electricity from off-vehicle sources, or may be self-contained with a battery or generator to convert fuel to electricity. An electric vehicle generally includes a rechargeable electricity storage system (RESS) (also called Full Electric Vehicles (FEV)). Power storage methods may include: chemical energy stored on the vehicle in on-board batteries (e.g., battery electric vehicle or BEV), on board kinetic energy storage (e.g., flywheels), and/or static energy (e.g., by on-board double-layer capacitors). Batteries, electric double-layer capacitors, and flywheel energy storage may be forms of rechargeable on-board electrical storage.

The term "electronic product code" ("EPC") is a universal identifier that provides a unique identity for every physical object anywhere in the world, for all time. Its structure is defined in the EPCglobal Tag Data Standard. The EPCglobal Tag Data Standard defines the structure of the URI syntax and binary format, as well as the encoding and decoding rules to allow conversion between these representations. The canonical representation of an EPC is a URL–the 'pure-identity URI' that is intended for use when referring to a specific physical object in communications about EPCs among information systems and business application software. Each coding scheme within the EPC identifier framework is distinguished through the use of a separate namespace. In the URI notations, this is indicated using a URI prefix such as urn:epc:id:sgtin or urn:epc:sscc. In the compact binary encoding of an EPC identifier, the namespace is instead indicated using a compact binary header (typically the first 8 bits of the binary encoding of an EPC identifier). The EPCglobal Tag Data Standard provides details of the URI prefixes and corresponding binary header values. This namespace indicator (URI prefix or compact binary header value) in turn dictates the length, type and structure of the EPC. EPC encoding schemes are used to uniquely identify one object. Most EPCs include an element within their structure that corresponds to a serial number.

The term "hybrid electric vehicle" refers to a vehicle that may combine a conventional (usually fossil fuel-powered) powertrain with some form of electric propulsion. Most hybrid electric vehicles combine a conventional internal combustion engine (ICE) propulsion system with an electric propulsion system (hybrid vehicle drivetrain). In parallel hybrids, the ICE and the electric motor are both connected to the mechanical transmission and can simultaneously transmit power to drive the wheels, usually through a conventional transmission. In series hybrids, only the electric motor drives the drivetrain, and a smaller ICE works as a generator to power the electric motor or to recharge the batteries. Power-split hybrids combine series and parallel characteristics. A full hybrid, sometimes also called a strong hybrid, is a vehicle that can run on just the engine, just the batteries, or a combination of both. A mid hybrid is a vehicle that cannot be driven solely on its electric motor, because the electric motor does not have enough power to propel the vehicle on its own.

The term "product code" refers to any identifier of a trade or other commerce item. One type of product code is the "universal product code" or "UPC" that refers to a barcode used in tracking items in the stream of commerce. Typically, the UPC includes 12 numerical digits, that are uniquely assigned to each trade item. Along with the related EAN barcode (another type of produce code), the UPC is the barcode mainly used for scanning of commerce items at the point of sale. The International Article Number (EAN) (also known as European Article Number, which technically refers to EAN-13) (yet another type of product code) is a 13-digit barcode symbology, which is a superset of the original 12-digit Universal Product Code ("UPC"). UPC data structures are a component of GTINs (yet another type of product code) and follow the global GS1 specification, which is based on international standards. But some retailers (clothing, furniture) do not use the GS1 system (rather other barcode symbologies or article number systems). On the other hand, some retailers use the EAN/UPC barcode symbology (yet another type of product code), but without using a GTIN (for products, brands, sold at such retailers only). Global Trade Item Number (GTIN) is an identifier for commerce items, developed by GS1. Such identifiers are used to look up product information in a database (often by entering the number through a barcode scanner pointed at an actual product) which may belong to a retailer, manufacturer, collector, researcher, or other entity. The GTIN standard has incorporated the International Standard Book Number (ISBN), International Standard Serial Number (ISSN), International Standard Music Number (ISMN), International Article Number (which includes the European Article Number and Japanese Article Number) and some Universal Product Codes, into a universal number space. GTINs may be 8, 12, 13 or 14 digits long, and each of these 4 numbering structures are constructed in a similar fashion, combining Company Prefix, Item Reference and a calculated Check Digit (GTIN-14 adds another component—the Indicator Digit, which can be 1-8).

The term "rechargeable electric vehicle" or "REV" refers to a vehicle with on board rechargeable energy storage, including electric vehicles and hybrid electric vehicles.

The term "Quick Response Code" or "QR code" refers to a matrix barcode (or two-dimensional barcode) that is a machine-readable optical label containing information about the item to which it is attached. A QR code commonly uses four standardized encoding modes (numeric, alphanumeric, byte/binary, and kanji) to efficiently store data; extensions may also be used. A QR code includes black squares arranged in a square grid on a white background, which can be read by an imaging device such as a camera, and processed using Reed-Solomon error correction until the image can be appropriately interpreted. The required data can then be extracted from patterns that are present in both horizontal and vertical components of the image.

What is claimed is:

1. A vehicle, comprising:
   a power source to propel the vehicle, the power source having one or more identifiers associated therewith;
   a user interface to receive commands from an occupant and provide output to the occupant;
   a plurality of on board sensors to sense one or more parameters associated with the power source;
   a reader to determine the one or more identifiers for the power source;
   a computer readable medium for storing the one or more sensed parameters for the power source; and
   an on board microprocessor, coupled with the computer readable medium, that is programmed to:
      provide the one or more identifiers and the one or more sensed parameters for the power source to a remote server to determine, based on stored parameter magnitudes over time for the power source identified by the one or more identifiers, whether the one or more sensed parameters for the power source fall within a standard deviation of the stored parameter magnitudes over time for the power source, the standard deviation defining a range of match values above and below the stored parameter magnitudes over time, and apply the following rules:
      when the one or more sensed parameters for the power source fall below and outside the standard deviation of the stored parameter magnitudes over time for the power source, determine that a rule is violated and send, to the occupant via the user interface, a notice comprising information about the one or more sensed parameters for the power source falling below and outside the standard deviation of the stored parameter magnitudes over time for the power source;
      when the one or more sensed parameters for the power source fall above and outside the standard deviation of the stored parameter magnitudes over time for the power source, determine that the rule is violated and send, to the occupant via the user interface, a notice comprising information about the one or more sensed parameters for the power source falling above and outside the standard deviation of the stored parameter magnitudes over time for the power source; and
      when the one or more sensed parameters for the power source fall within the standard deviation of the stored parameter magnitudes over time for the power source, determine that the rule is not violated and transmit, to the occupant via the user interface, a response comprising information about the one or more sensed parameters for the power source falling within the standard deviation of the stored parameter magnitudes over time for the power source.

2. The vehicle of claim 1, wherein the rule is a warranty rule, wherein the power source is a battery pack, and wherein the one or more identifiers are a serial code, Universal Product Code ("UPC"), Quick Response ("QR") code, Electronic Product Code ("EPC"), or RFID tag and wherein the one or more sensed parameters for the power source and the one or more stored parameter magnitudes over time for the power source correspond to one or more of stored energy level, winding temperature, voltage level, output electrical current, electrical current direction of flow, leakage current, temperature, state-of-charge, state-of-health, state-of-function, number of charge-discharge cycles, depth of discharge, cycle life, and calendar life.

3. The vehicle of claim 2, wherein the one or more sensed parameters for the power source and the one or more stored parameter magnitudes over time for the power source correspond to one or more of stored energy level, voltage level, output electrical current, leakage current, state-of-charge, state-of-health, state-of-function, number of charge-discharge cycles, cycle life, and calendar life, wherein the one or more identifiers and the one or more sensed parameters for the power source and the one or more stored parameter magnitudes over time for the power source are associated with a module, battery, or cell, wherein the one or more identifiers are each multiple identifiers, and wherein the one or more sensed parameters for the power source and the one or more stored parameter magnitudes over time for the power source are each multiple power source parameters.

4. The vehicle of claim 3, wherein the one or more identifiers comprises an RFID associated with an RFID tag, wherein more than one RFID tag responds at a selected time to the reader, and wherein to disambiguate between concurrent responses from different RFID tags, the reader broadcasts (a) an initialization command and a parameter that each RFID tag individually uses to pseudo-randomly delay a respective response or (b) sends an initialization symbol and then transmits one or more bits of identification data at a time, with only a single RFID tag having a matching bit responding to the transmitted one or more bits of identification data.

5. The vehicle of claim 2, wherein the one or more stored parameter magnitudes over time for the power source and the one or more sensed parameters for the power source are each non-uniform among power sources of plural vehicles and are time-varying or stored charge-varying.

6. The vehicle of claim 1, wherein the one or more sensed parameters for the power source define a current magnitude of a state-of-health associated with the power source, and wherein determining that the rule is violated comprises determining that the current magnitude of the state-of-health associated with the power source falls below a stored magnitude of a state-of-health for the power source.

7. The vehicle of claim 1, wherein the reader is one or more of an active RFID tag reader, optical reader, illumination source and optical sensor, and magnetic reader.

8. A vehicle, comprising:
   a power source to propel the vehicle, the power source having one or more identifiers associated therewith;
   a user interface to receive commands from an occupant and provide output to the occupant;
   a plurality of on board sensors to sense one or more parameters associated with the power source;
   a reader to determine the one or more identifiers for the power source;
   a computer readable medium for storing the one or more sensed parameters for the power source; and
   an on board microprocessor, coupled with the computer readable medium, that is programmed to:
      determine, based on stored parameter magnitudes over time for the power source identified by the one or more identifiers, whether the one or more sensed parameters for the power source fall within a standard deviation of the stored parameter magnitudes over time for the power source, the standard deviation defining a range of match values above and below the stored parameter magnitudes over time, and apply the following rules:

when the one or more sensed parameters for the power source fall below and outside the standard deviation of the stored parameter magnitudes over time for the power source, determine that a rule is violated and send, to the user interface, a notice comprising information about the one or more sensed parameters for the power source falling below and outside the standard deviation of the stored parameter magnitudes over time for the power source;

when the one or more sensed parameters for the power source fall above and outside the standard deviation of the stored parameter magnitudes over time for the power source, determine that the rule is violated and send, to the occupant via the user interface, a notice comprising information about the one or more sensed parameters for the power source falling above and outside the standard deviation of the stored parameter magnitudes over time for the power source; and when the one or more sensed parameters for the power source fall within the standard deviation of the stored parameter magnitudes over time for the power source, determine that the rule is not violated and transmit, to the occupant via the user interface, a response comprising information about the one or more sensed parameters for the power source falling within the standard deviation of the stored parameter magnitudes over time for the power source.

9. The vehicle of claim 8, wherein the rule is a warranty rule, wherein the power source is a battery pack, and wherein the one or more identifiers are a serial code, Universal Product Code ("UPC"), Quick Response ("QR") code, Electronic Product Code ("EPC"), or RFID tag and wherein the one or more sensed parameters of the power source and the one or more stored parameter magnitudes over time for the power source correspond to one or more of stored energy level, winding temperature, voltage level, output electrical current, electrical current direction of flow, leakage current, temperature, state-of-charge, state-of-health, state-of-function, number of charge-discharge cycles, depth of discharge, cycle life, and calendar life.

10. The vehicle of claim 9, wherein the one or more sensed parameters for the power source and the one or more stored parameter magnitudes over time for the power source correspond to one or more of stored energy level, voltage level, output electrical current, leakage current, state-of-charge, state-of-health, state-of-function, number of charge-discharge cycles, cycle life, and calendar life, wherein the one or more identifiers and the one or more sensed parameters for the power source and the one or more stored parameter magnitudes over time for the power source are associated with a module, battery, or cell, wherein the one or more identifiers are each multiple identifiers, and wherein the one or more sensed parameters for the power source and the one or more stored parameter magnitudes over time for the power source are each multiple power source parameters.

11. The vehicle of claim 10, wherein the one or more identifiers is an RFID associated with an RFID tag, wherein more than one RFID tag responds at a selected time to the reader, and wherein to disambiguate between concurrent responses from different RFID tags, the reader broadcasts (a) an initialization command and a parameter that each RFID tag individually uses to pseudo-randomly delay a respective response or (b) sends an initialization symbol and then transmits one or more bits of identification data at a time, with only a single RFID tag having a matching bit responding to the transmitted one or more bits of identification data.

12. The vehicle of claim 9, wherein the one or more stored parameter magnitudes over time for the power source and the one or more sensed parameters for the power source are each non-uniform among power sources of plural vehicles and are time-varying or stored charge-varying.

13. The vehicle of claim 8, wherein the one or more sensed parameters for the power source define a current magnitude of a state-of-health associated with the power source, and wherein determining that the rule is violated comprises determining that the current magnitude of the state-of-health associated with the power source falls below a stored magnitude of a state-of-health for the power source.

14. The vehicle of claim 8, wherein the reader is one or more of an active RFID tag reader, optical reader, illumination source and optical sensor, and magnetic reader.

15. A server, comprising:
a computer readable medium for storing one or more identifiers and one or more parameters for a power source corresponding to plural vehicles, each vehicle comprising the corresponding power source to propel the vehicle, the corresponding power source having one or more identifiers associated therewith, a plurality of on board sensors to sense one or more parameters for the corresponding power source, and a reader to determine the one or more identifiers for the corresponding power source; and
a microprocessor, coupled with the computer readable medium, that is programmed to:
receive, from each vehicle, the respective one or more identifiers and the respective sensed parameter for the corresponding power source to determine, based on stored parameter magnitudes over time for the corresponding power source identified by the one or more stored identifiers, whether the one or more sensed parameters for the corresponding power source fall within a standard deviation of the stored parameter magnitudes over time for the corresponding power source, the standard deviation defining a range of match values above and below the stored parameter magnitudes over time, and apply the following rules for each vehicle:
when the one or more sensed parameters for the corresponding power source fall below and outside the standard deviation of the stored parameter magnitudes over time for the corresponding power source, determine that a rule is violated and cause a notice comprising information about the one or more sensed parameters for the corresponding power source falling below and outside the standard deviation of the stored parameter magnitudes over time for the corresponding power source to be sent to an occupant via a user interface;
when the one or more sensed parameters for the corresponding power source fall above and outside the standard deviation of the stored parameter magnitudes over time for the corresponding power source, determine that the rule is violated and cause a notice comprising information about the one or more sensed parameters for the corresponding power source falling above and outside the standard deviation of the stored parameter magnitudes over time for the corresponding power source to be sent to the occupant via the user interface; and when the one or more sensed parameters for the corresponding power source falls within the standard deviation of the stored parameter magnitudes over time for the corresponding power source, determine that the rule is not violated and cause a response comprising information about the one or more sensed parameters for the corresponding power source falling within the standard deviation of the stored parameter magnitudes over time for the corresponding power source to be transmitted for presentation to the occupant via the user interface.

16. The server of claim 15, wherein the rule is a warranty or licensing rule, wherein the power source is a battery pack, and wherein the one or more identifiers are a serial code, Universal Product Code ("UPC"), Quick Response ("QR") code, Electronic Product Code ("EPC"), or RFID tag and wherein the one or more sensed parameters for the power source and the one or more stored parameter magnitudes over time for the power source correspond to one or more of stored energy level, winding temperature, voltage level, output electrical current, electrical current direction of flow, leakage current, temperature, state-of-charge, state-of-health, state-of-function, number of charge-discharge cycles, depth of discharge, cycle life, and calendar life.

17. The server of claim 16, wherein the one or more sensed parameters for the power source and the one or more stored parameter magnitudes over time for the power source correspond to one or more of stored energy level, voltage level, output electrical current, leakage current, state-of-charge, state-of-health, state-of-function, number of charge-discharge cycles, cycle life, and calendar life, wherein, for a selected vehicle, the one or more identifiers and the one or more sensed parameters for the power source and the one or more stored parameter magnitudes over time for the power source are associated with a module, battery, or cell, wherein, for the selected vehicle, the one or more identifiers are each multiple identifiers, and wherein, for the selected vehicle, the sensed one or more parameters for the power source and the one or more stored parameter magnitudes over time for the power source are each multiple power source parameters.

18. The server of claim 17, wherein the one or more identifiers comprise an RFID associated with an RFID tag, wherein more than one RFID tag responds at a selected time to the reader of the selected vehicle, and wherein to disambiguate between concurrent responses from different RFID tags, the reader broadcasts (a) an initialization command and a parameter that each RFID tag individually uses to pseudo-randomly delay a respective response or (b) sends an initialization symbol and then transmits one or more bits of identification data at a time, with only a single RFID tag having a matching bit responding to the transmitted one or more bits of identification data.

19. The server of claim 15, wherein, for a selected vehicle, the one or more sensed parameters for the power source define a current magnitude of a state-of-health associated with the power source, and wherein determining that the rule is violated comprises determining that the current magnitude of the state-of-health associated with the power source falls below a stored magnitude of a state-of-health for the power source.

20. The server of claim 15, wherein the reader is one or more of an active RFID tag reader, optical reader, illumination source and optical sensor, and magnetic reader.

* * * * *